(12) United States Patent
Hudlicky et al.

(10) Patent No.: US 8,853,401 B2
(45) Date of Patent: Oct. 7, 2014

(54) PROCESSES FOR THE PREPARATION OF MORPHINANE AND MORPHINONE COMPOUNDS

(75) Inventors: Tomas Hudlicky, St. Catharines (CA); Robert Carroll, Stevenage (GB); Hannes Leisch, Attersee (AT); Ales Machara, Brevnov (CZ); Lukas Werner, Kadan (CZ); David R. Adams, Thorold (CA)

(73) Assignee: Brock University, Ontario (CA)

( * ) Notice: Subject to any disclaimer, the term of this patent is extended or adjusted under 35 U.S.C. 154(b) by 298 days.

(21) Appl. No.: 13/264,182

(22) PCT Filed: Apr. 22, 2010

(86) PCT No.: PCT/CA2010/000587
§ 371 (c)(1),
(2), (4) Date: Oct. 13, 2011

(87) PCT Pub. No.: WO2010/121369
PCT Pub. Date: Oct. 28, 2010

(65) Prior Publication Data
US 2012/0046465 A1    Feb. 23, 2012

Related U.S. Application Data

(60) Provisional application No. 61/172,521, filed on Apr. 24, 2009.

(51) Int. Cl.
*C07D 489/02*    (2006.01)
*C07D 489/12*    (2006.01)

(52) U.S. Cl.
USPC ................................. 546/44; 546/39; 546/46

(58) Field of Classification Search
USPC .............................................. 546/44, 46, 39
See application file for complete search history.

(56) References Cited

U.S. PATENT DOCUMENTS

| | | | |
|---|---|---|---|
| 5,849,915 A | 12/1998 | Kim et al. | |
| 7,655,671 B2 | 2/2010 | Schmidhammer et al. | |
| 7,674,904 B2 | 3/2010 | Doshan et al. | |

FOREIGN PATENT DOCUMENTS

| | | |
|---|---|---|
| CA | 2671518 | 6/2008 |
| JP | 10-059849 A | 3/1998 |
| JP | 2006-500326 A | 1/2006 |
| JP | 2008-542287 A | 11/2008 |
| WO | 01/13909 A2 | 3/2001 |
| WO | 20081070658 A1 | 6/2008 |
| WO | 2009/003270 A1 | 1/2009 |
| WO | 2009/004491 | 1/2009 |

OTHER PUBLICATIONS

Lopez, D., et al. "The [4+2]] addition of singlet oxygen to thebaine: new access to highly functionalized morphine derivatives via opioid endoperoxides." J Org Chem. Jul. 28, 2000;65(15):4671-8.
European Search Report of Application No. 10766555.6 (PCT/CA2010/000587). Issued: Jul. 3, 2012.
Manoharan, T.S., et al. "Stereoselectivity in Quaternization of Thebaine: 372 MHz PMR Spectroscopic Studies." Indian J Chem., Feb. 1987;26B:140-142.
Manoharan, T.S., et al. "A Convenient Method for Replacing the N-Methyl Group of Morphine, Codeine, and Thebaine by Other Alkyl Groups." Synthesis, Oct. 1983; 809-812.
Bognar, R., et al. "Selective Quaternization in the Morphine Series." Tetrahydron Letters, 1964;39:2867-2871.
Lopez, D., et al. "Photoxidation of Thebaine. A Route to 14-Hydroxymorphinones and Hydrodibenzofuran Analogs of Methadone." Tetrahedron Letters, 1994;35(31):5727-5730.
Third Party's Observation dated Aug. 3, 2012 EP Patent Application No. 10766555.6.
Linders, J.T.M. "Synthesis and Diels-Alder Reactions of Novel Morphinandienes." Ph.D. dissertation. Delft University of Technology. 1989. pp. 1, 2, 50 and 51.
NIDA Research Monograph Series 96. "Drugs of Abuse: Chemistry, Pharmacology, Immunology and AIDS." Phuong Thi Kim, Ph.D. & Kenner Rice, Ph.D., eds. U.S. Dept. of Health & Human Services. 1990. pp. 1, 2, 26 and 27.
Japanese Notice of Reasons for Rejection (Translation), dated Jun. 4, 2014, issued in corresponding Japanese Patent Application No. 2012-506298.

*Primary Examiner* — Charanjit Aulakh
(74) *Attorney, Agent, or Firm* — Patrick J. Hagan; Dann, Dorfman, Herrell & Skillman, P.C.

(57) ABSTRACT

The present application describes processes for the synthesis of morphinane and morphinone compounds, useful as pharmaceutical agents. Also included are novel intermediates useful in the preparation of these compounds. The process comprises quaternization of oripavine to provide a mixture of the R- and S-isomeric (at the nitrogen) quaternary salts. The R-isomer is readily isolated and converted to various N-(R)-morphinane and N-(S)-morphinone compounds. The R-isomer, S-isomer or a mixture of R- and S-isomers may be demethylated and converted to various morphinane and morphinone compounds.

27 Claims, 1 Drawing Sheet

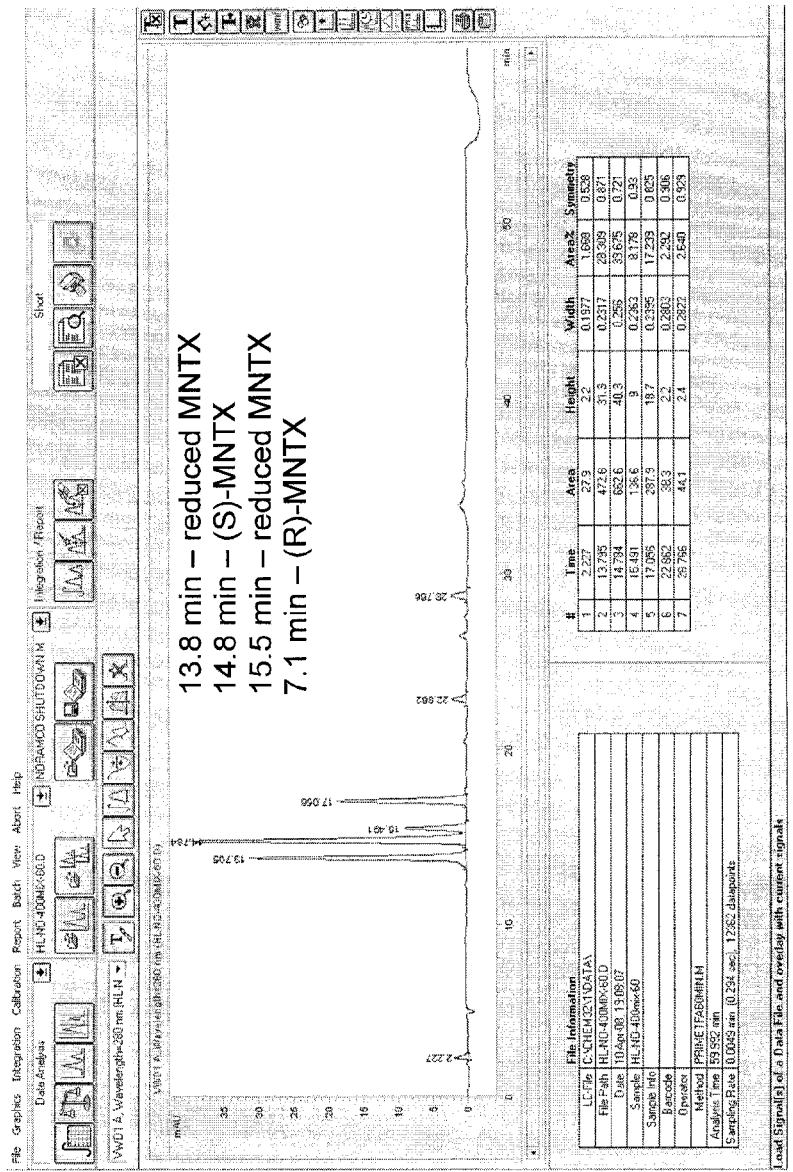

PROCESSES FOR THE PREPARATION OF MORPHINANE AND MORPHINONE COMPOUNDS

This application is a §371 national phase entry of PCT/CA2010/000587 filed Apr. 22, 2010, which claims priority under 35 U.S.C. §119(e) to U.S. Provisional Application 61/172,521, filed Apr. 24, 2009, the entire contents being incorporated herein by reference as though set forth in full.

FIELD OF THE APPLICATION

The present application is directed to processes and intermediates for the preparation of various opioid analgesics, including morphinane and morphinone compounds such as naltrexone, R-methylnaltrexone, buprenorphine, nalbuphone and nalbuphine.

BACKGROUND OF THE APPLICATION

Opioid analgesics are often the treatment of choice for patients with severe pain. Besides its beneficial analgesia, opioids induce undesired side effects such as addiction, constipation, nausea and respiratory depression. Commonly administered drugs are the naturally occurring opiates isolated from opium or poppy straw, morphine and codeine, as well as semi-synthetic opioids derived from thebaine such as oxycodone and buprenorphine. The intense biological response is caused by their agonistic action to specific opioid receptors in the human body. In contrast, naltrexone, which is used for rapid detoxification of opioid dependent patients and methylnaltrexone are examples of opioid antagonists.

Goldberg and coworkers as well as more recently Cantrell and coworkers reported the syntheses of methylnaltrexone from naltrexone with appropriate methylating reagents such as methyl iodide or methyl bromide. [see, Goldberg et al., U.S. Pat. No. 4,176,186 and Cantrell et al., WO2004/043964]. Although quaternized morphine alkaloids occur as two diastereomers (the quaternized nitrogen represents an additional chiral center), both groups remained silent about the possible diastereomeric salts and reported a single isomer. In 2006 the first two "diastereoselective" syntheses of (R)- and (S)-methylnaltrexone were reported. The structure of (R)-methylnaltrexone (1) and (S)-methylnaltrexone (2) are shown in Scheme 1.

SCHEME 1

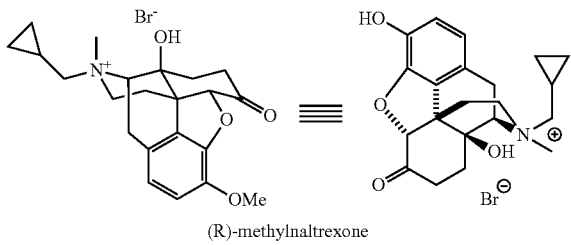

(R)-methylnaltrexone

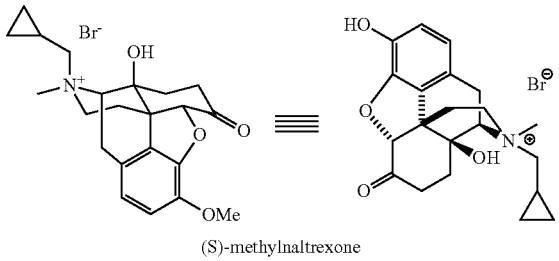

(S)-methylnaltrexone

The reaction of naltrexone with methylbromide yielded predominantly (R)-methylnaltrexone [see, Doshan, H. D.; Perez, J. WO2006/127899], presumably the same compound as reported by Cantrell and Goldberg. Wang et al., [WO 2008/109156] have developed a further improved method by reacting naltrexone in an anhydrous aprotic dipolar solvent in the presence of 0.01-0.25 equivalents of HBr (relative to naltrexone) to suppress methylation of the C-3-hydroxide. In the same application, they achieved further improvement by first protecting the C-3-hydroxide with an acetyl group, quaternizing the acetyl-naltrexone with methyl bromide in N-methyl-2-pyrrolidone (NMP), and then removing the C-3-actyl group to give crude (R)-methylnaltrexone bromide (MNTX) in 83-87% molar yield.

Dlubala reported the conversion of naltrexone to methylnaltrexone bromide by first protecting the 3-O position with a benzyl group, reacting the benzyl-protected naltrexone with dimethylsulfate, followed by conversion of the resulting methylnaltrexone methylsulfate salt to the zwitterion, and then removal of the 3-O-benzyl protecting group and simultaneous precipitation of methylnaltrexone bromide by the addition of aqueous HBr, yielding also predominantly the (R)-methylnaltrexone [see Dlubala, WO 2008/034973, US 2008/0214817]. The addition of cyclopropylmethylenebromide to oxymorphone gave the (S)-isomer [see, Wagoner, H.; et al., WO2006/127898]. Not surprisingly, the (S)-isomer of methylnaltrexone exhibited different activities than those reported previously in the literature. These findings are in accordance with Bianchetti and coworkers, who studied the in vivo as well in vitro activity of three pairs of diastereoisomers of quaternary opioid antagonists derived from levallorphan, nalorphine, and naloxone. [Bianchetti, A. et al., Life Sciences 1983, 33(Suppl.1), 415-418]. Only the diastereomers prepared by methylation of the alkylated morphine derivative showed antagonistic activities.

The prior art methods for making methylnaltrexone of Goldberg et al., Cantrell et al., Doshan and Perez, Wang et al, and Dlubala all start from naltrexone. There are several possible routes to naltrexone (see Scheme 2) from biologically available raw materials (morphine, codeine, thebaine and oripavine), and all possible routes require a minimum of six chemical transformations, not including purifications of intermediates or the final product. Furthermore, when purifications of intermediates and/or the final product are included to meet the quality requirements of a drug substance, the molar yield of the final product relative to the biologically available raw material in each case falls below 30%. Cultivation of the poppies, which produce the biological raw materials, is tightly controlled, limiting their supply. The relatively high raw material costs and the manufacturing costs for each of the chemical conversions contribute to the cost of the final product.

SCHEME 2

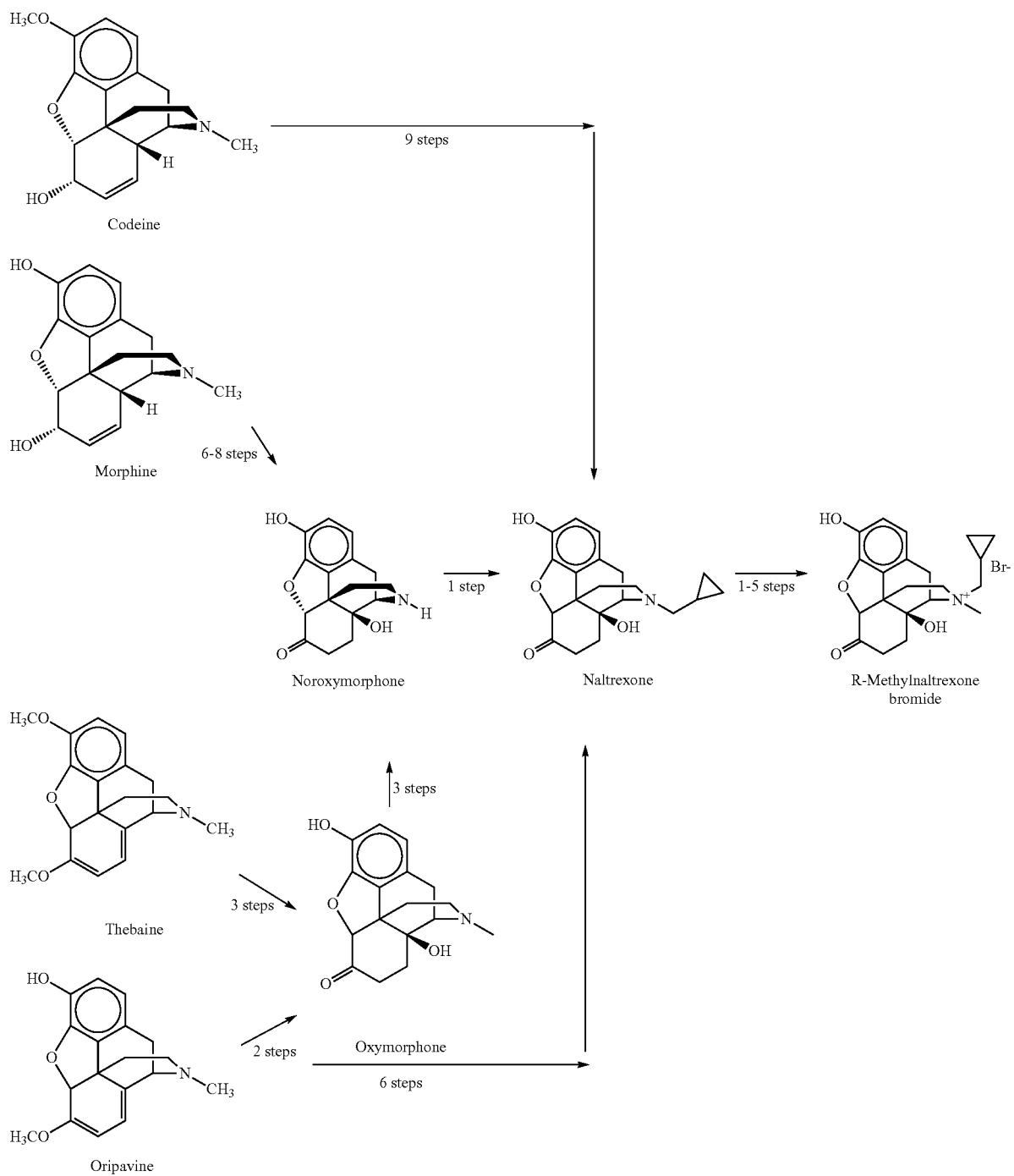

A common feature of each of these routes is that at some point, the N-17 methyl group, which is common to each of the biological raw materials, is removed, a cyclopropylmethylene group is added, and a methyl group is added back in the final step. As noted earlier, quaternization of the nitrogen with a cyclopropylmethyl halide (at oxymorphone for example) gives the undesired S configuration at the nitrogen.

Even for the conversion of naltrexone to methylnaltrexone bromide, the number of chemical transformation steps ranges from one (Cantrell et al., Scheme 3), to four (Doshan and Perez; Scheme 4) to five (Dlubala, Scheme 5). In a very recent application, Wang et al., [WO 2008/109156] pointed out that the earlier one step Cantrell method gave a 60% molar yield of approximately 90% pure methylnaltrexone bromide which required a three step purification to give pure methylnaltrexone bromide. Wang et al developed a one-pot procedure, which comprises three chemical transformations (Scheme 6) and delivers methylnaltrexone in good yield (83-87% on a crude basis and 71% after purification).

SCHEME 3
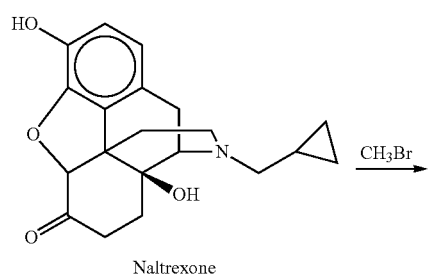
SCHEME 4
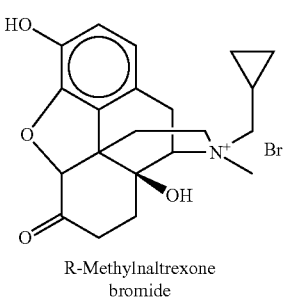
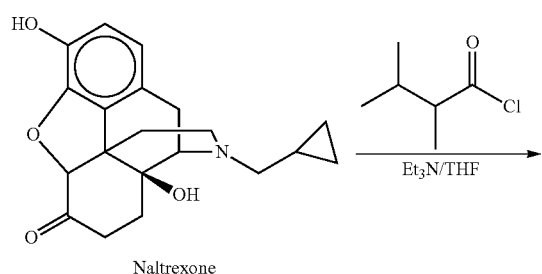
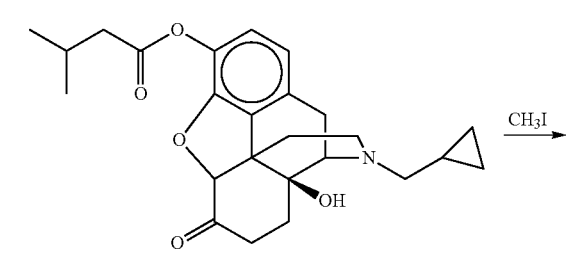
-continued
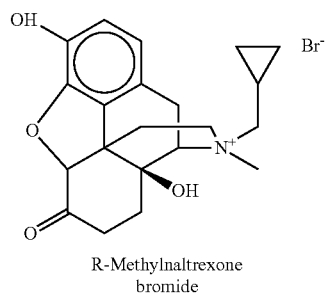
SCHEME 5
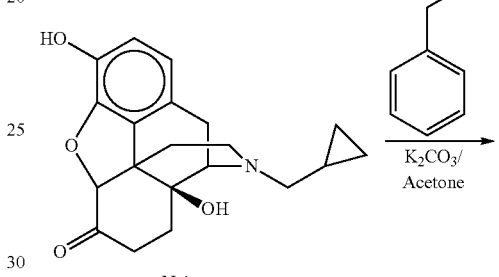
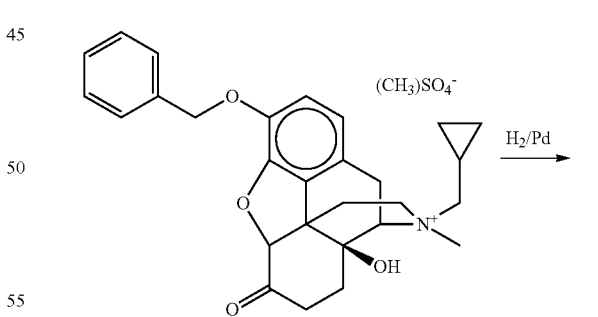
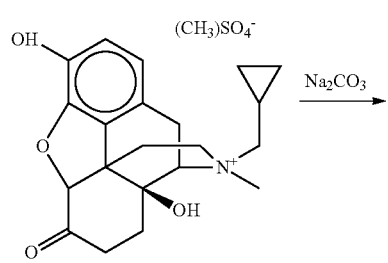

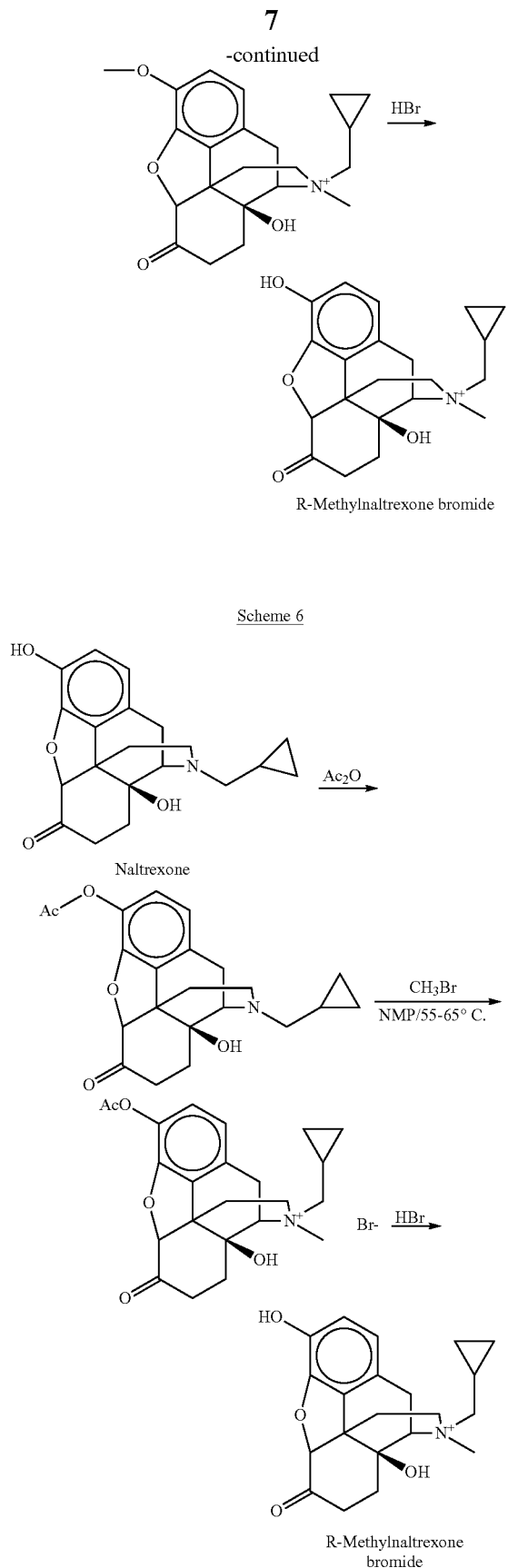

Scheme 6

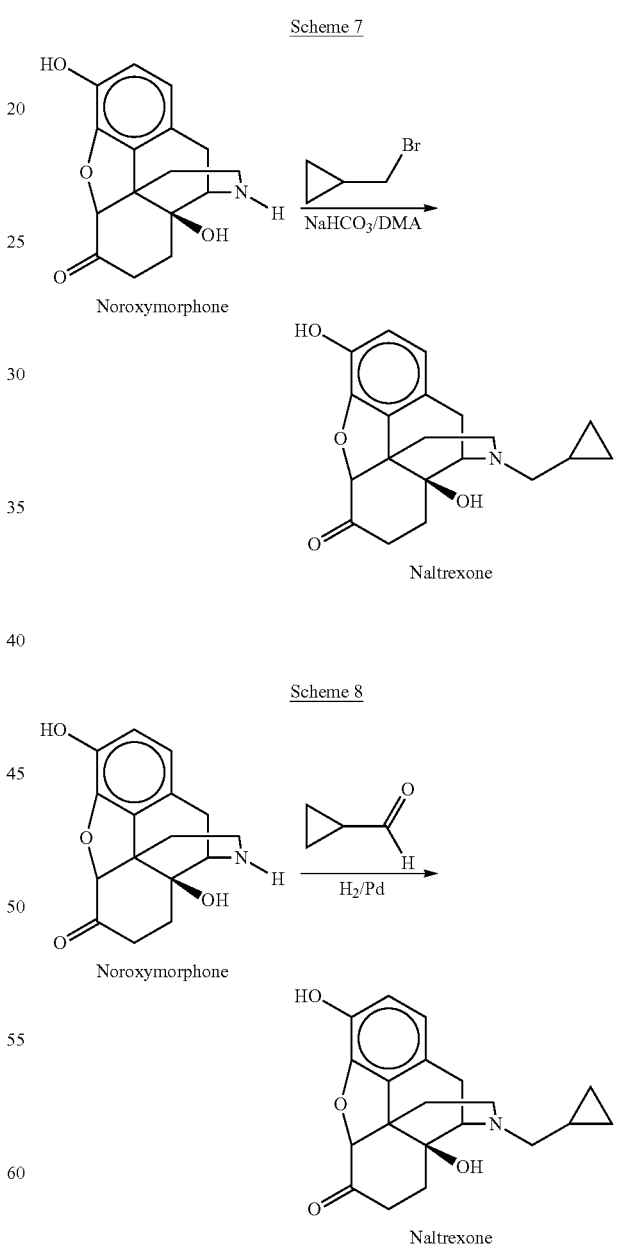

Scheme 7

Scheme 8 most efficient process to convert a biological raw material to methylnaltrexone via naltrexone requires a minimum of nine chemical transformations.

Representative examples of naltrexone syntheses are shown in Schemes 7-8. Scheme 7 shows a common commercial route for the manufacture of naltrexone is the alkylation of noroxymorphone in the presence of cyclopropylmethyl bromide and sodium hydrogen carbonate in dimethylacetamide at 65-69° C. for 6 hours to give naltrexone in 88.6% yield [Dlubala; US 2008/0214817 A1]. Naltrexone may also be manufactured from noroxymorphone by reductive alkylation with cyclopropylcarboxaldehyde [Goodwin et al., WO 2006/035195; Scheme 8]. The yield of naltrexone isolated as the hydrochloride salt ranged from 74-83%.

Although the shortest route from a biological raw material requires a minimum of seven chemical transformations, the Noroxymorphone may in turn be prepared from morphine in 6 steps [Wallace, U.S. Pat. No. 5,112,975] or from thebaine via oxymorphone in 6 steps by the procedure described in Kavka, [U.S. Pat. No. 4,639,520]. Oxymorphone may also be prepared from oripavine using the procedure described by Wang et al, 2008118654/WO-A1, Dung et al., WO 2008072018 or Huang, WO 2008048711 and WO 2008048957.

Huang et al, [U.S. Pat. Nos. 5,869,669, 6,008,354 and 6013796] describe the synthesis of naltrexone from morphine and codeine in seven to nine chemical steps. In a subsequent application, Huang, [US 20080125592. assigned to Penick] describe the synthesis of naltrexone from oripavine in six chemical steps, combined into three unit operations.

In addition to the low overall conversion of biologically available raw materials and the number of chemical transformations, there remains the problem of the separation of the last traces of the S-isomer from the desired R-isomer of methylnaltrexone bromide to give a product containing levels not more than those specified by the ICH Guidelines for related substances (NMT 0.15%) in a drug substance. The preparations described by Doshan outlined in Scheme 6 gives a crude product containing 94.4% R-MNTX and 4.7% S-MNTX. After the first recrystallization from methanol, the product contained 98.0% R-MNTX and 1.5% S-MNTX. After a second recrystallization, the product contained 98.3% R-MNTX and 1.2% S-MNTX. On this basis, multiple recrystallizations with concomitant loss of R-MNTX would be necessary to achieve a product containing less than 0.15% S-MNTX.

The procedure of Wang et al. delivers crude methylnaltrexone containing 1.25-1.47% of the S-methylnaltrexone diastereomer, and 0.49-0.60% unreacted naltrexone and methylnaltrexone after purification containing 0.30-0.40% S-methylnaltrexone diastereomer, and 0.08-0.15% unreacted naltrexone.

Most preparations of buprenorphine in the literature involve a [4+2] cycloaddition reaction between thebaine or oripavine, or a protected derivative thereof, and methyl vinyl ketone, followed by reduction. A Grignard reaction is typically used to install the appropriate alkyl group at the C-7 pendant group and the installation of the N-cyclopropylmethylene group is typically performed later in the synthesis using a demethylation-realkylation reaction sequence. Representative examples of such preparations of buprenorphine are Zhong et al. [U.S. Pat. No. 7,119,100], Mannino et al. [US 2008/0312441], Bentley et al. [GB 1136214, U.S. Pat. No. 3,433,791], Huang et al. [US2008/0125592] and Zhang et al [Yiyao Gongye, Vol 2, 6-8, 1983].

SUMMARY OF THE APPLICATION

A new process has been developed for the synthesis of morphinane and morphinone compounds, including, but not limited to, naltrexone, R-methylnaltrexone, buprenorphine, nalbuphone and nalbuphine. This process involves the N-substitution of oripavine or thebaine to provide a mixture of the corresponding (R)- and (S)-N-substituted derivatives. The desirable R-isomer is isolated in substantially pure form using known methods such as precipitation, recrystallization or chromatography and is converted to, for example, R-methylnaltrexone or R-methylbuphenone. The remaining side products, including the S-isomer and mixtures of the R- and S-isomers are demethylated and the resulting N-substituted nororipavine, or analogs thereof, are converted to morphinane and morphinone compounds, including, but not limited to, naltrexone, R-methylnaltrexone, buprenorphine, nalbuphone and nalbuphine. Of course this latter series of reactions could also be performed using the R-isomer as the starting material. The preparation of R-methylnaltrexone from the R-isomer advantageously does not suffer from the problems associated with stereoselective methylation of naltrexone. The N-demethylation route represents a way to advantageously utilize the side products from the initial N-substitution reaction, reducing waste, and increasing the efficiency of the overall process in the synthesis of morphinane and morphinone compounds.

Accordingly, the application includes a process for preparing intermediates useful in the synthesis of morphinane and morphinone compounds comprising:

(a) reacting a compound of the formula (II) with a compound of the formula (III) under conditions to form compounds of the formulae R-(Ia) and S-(Ib):

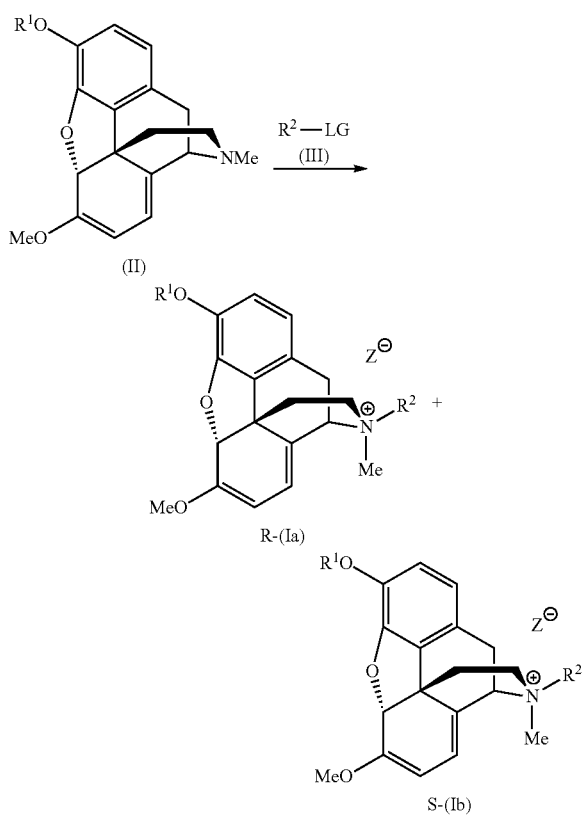

wherein $R^1$ is selected from hydrogen, $C_{1-6}$alkyl, $C(O)C_{1-6}$alkyl and PG;

$R^2$ is selected from $R^3$, $C(O)R^3$, $S(O)R^3$ and $SO_2R^3$;

$R^3$ is selected from $C_{1-6}$alkyl, $C_{1-6}$alkyleneC$_{3-8}$cycloalkyl, $C_{1-6}$alkyleneC$_{6-10}$aryl, $C_{1-6}$alkyleneC$_{1-8}$heterocyclyl and $C_{1-6}$alkyleneC$_{1-10}$heteroaryl;

LG is a leaving group;

PG is a protecting group; and each alkyl, alkylene and aryl is optionally fluoro-substituted and/or deuterated; and (b) optionally, isolating the compound of the formula R-(Ia); and (c) optionally, treating the compound of the formula S-(Ib), the compound of the formula R-(Ia) or a mixture of the compounds of the formulae R-(Ia) and S-(Ib) under N-demethylation conditions to form a compound of the formula (IV):

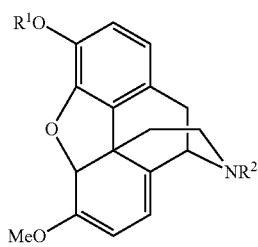

(IV)

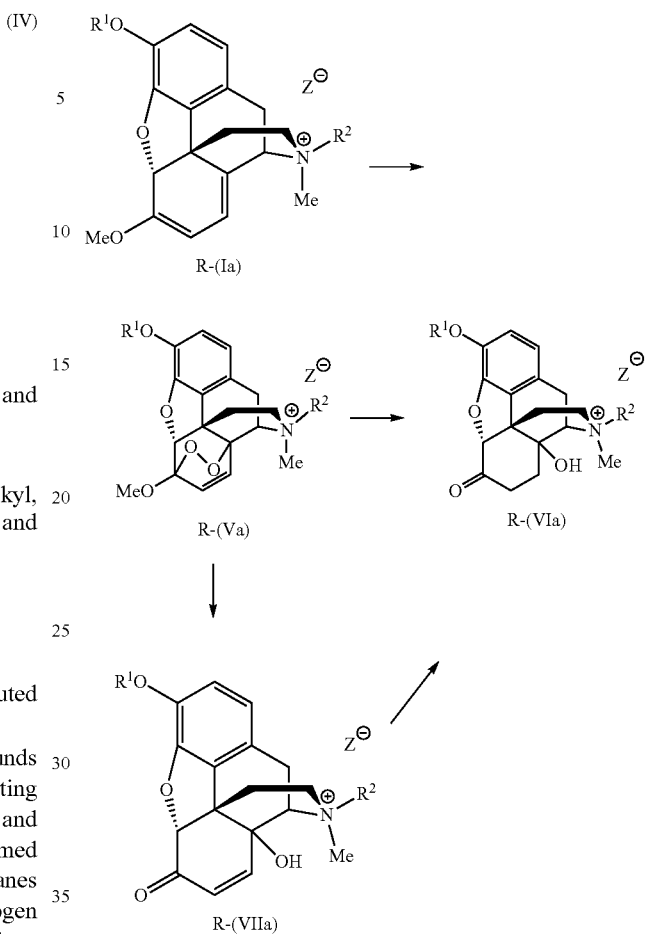

wherein $R^1$ is selected from hydrogen, $C_{1-6}$alkyl, $C(O)C_{1-6}$alkyl and PG;

$R^2$ is selected from $R^3$, $C(O)R^3$, $S(O)R^3$ and $SO_2R^3$;

$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl;

LG is a leaving group;

PG is a protecting group;

Z is a suitable counter anion; and each alkyl, alkylene and aryl is optionally fluoro-substituted and/or deuterated.

The above process provides intermediates, i.e. compounds of formulae R-(Ia), S-(Ib) and (IV), that are useful as starting materials in the preparation of a number of morphinones and morphinanes. Advantageously, this process is performed early in the preparation of the morphinones and morphinanes and avoids the step of quaternization of the N-17 nitrogen using a larger alkylating agent, such as cycloalkylmethylate, which generally provides the undesired S configuration at this nitrogen as the major product. In the process of the present application, the quaternization step, if needed, is done at a later stage and is done with a smaller methylating reagent, which provides the desired R configuration as the major product.

In one embodiment of the present application, the compounds of formula R-(Ia) or S-(Ib), or mixtures thereof are used in the preparation of R-methylnaltrexone, S-methylnaltrexone or mixtures thereof, or analogs thereof. In this embodiment, the compounds of the formula R-(Ia) and/or S-(Ib) are reacted with a source of singlet oxygen to form a novel endoperoxide intermediate or a peracid to form 14-hydroxymorphinone derivatives that are both reduced to R-methylnaltrexone and/or S-methylnaltrexone or analogs thereof.

Accordingly, the present application also includes a process of preparing R-methylnaltrexone, or analogs thereof of the formula (VIa), comprising:

(a) reacting a compound of the formula R-(Ia) with a source of singlet oxygen under conditions to form a compound of the formula R-(Va); and (b) reducing the compound of the formula R-(Va) under conditions to form the compound of the formula R-(VIa) or reducing the compound of the formula R-(Va) under conditions to form the compound of the formula R-(VIIa) followed by reducing the compound of the formula R-(VIIa) under conditions to form the compound of the formula R-(VIa):

wherein $R^1$ is selected from hydrogen, $C_{1-6}$alkyl, $C(O)C_{1-6}$alkyl and PG;

$R^2$ is selected from $R^3$, $C(O)R^3$, $S(O)R^3$ and $SO_2R^3$;

$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl, PG is a protecting group;

Z is a suitable counter anion; and each alkyl, alkylene and aryl is optionally fluoro-substituted and/or deuterated.

The present application also includes a process of preparing S-methylnaltrexone, or analogs thereof of the formula S-(VIb), comprising:

(a) reacting a compound of the formula S-(Ib) with a source of singlet oxygen under conditions to form a compound of the formula S-(Vb); and (b) reducing the compound of the formula S-(Vb) under conditions to form the compound of the formula S-(VIb) or reducing the compound of the formula S-(Vb) under conditions to form the compound of the formula S-(VIIb) followed by reducing the compound of the formula S-(VIIb) under conditions to form the compound of the formula S-(VIb):

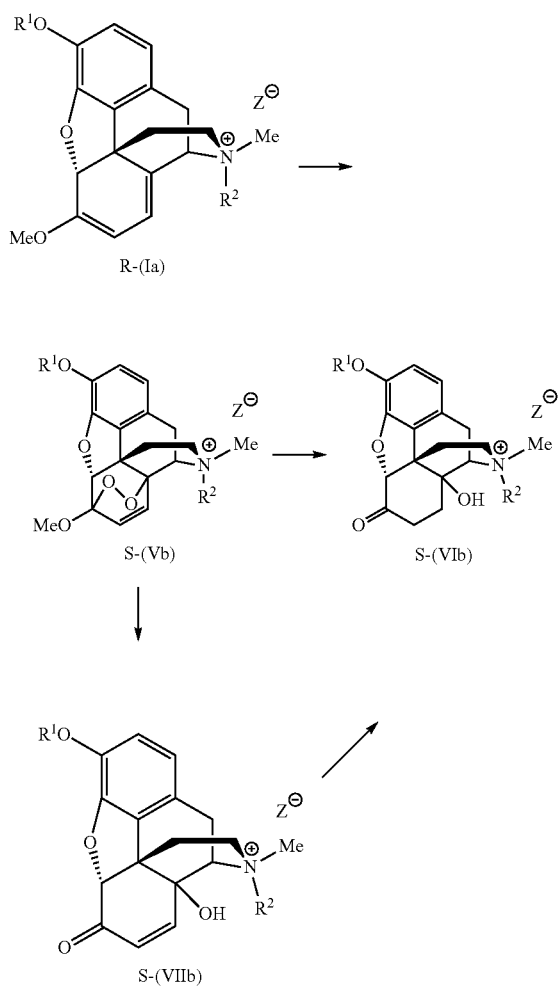

R-(Ia)

S-(Vb)    S-(VIb)

S-(VIIb)

wherein

R$^1$ is selected from hydrogen, C$_{1-6}$alkyl, C(O)C$_{1-6}$alkyl and PG;

R$^2$ is selected from R$^3$, C(O)R$^3$, S(O)R$^3$ and SO$_2$R$^3$;

R$^3$ is selected from C$_{1-6}$alkyl, C$_{1-6}$alkyleneC$_{3-8}$cycloalkyl, C$_{1-6}$alkyleneC$_{6-10}$aryl, C$_{1-6}$alkyleneC$_{1-8}$heterocyclyl and C$_{1-6}$alkyleneC$_{1-10}$heteroaryl;

PG is a protecting group;

Z is a suitable counter anion; and each alkyl, alkylene and aryl is optionally fluoro-substituted and/or deuterated, The present application also includes a process of preparing R-methylnaltrexone, or analogs thereof of the formula R-(VIa), comprising:

(a) reacting a compound of the formula R-(Ia) with a per-acid under conditions to form a compound of formula R-(VIIa); and (b) reducing the compound of the formula R-(VIIa) under conditions to form a compound of the formula R-(VIa):

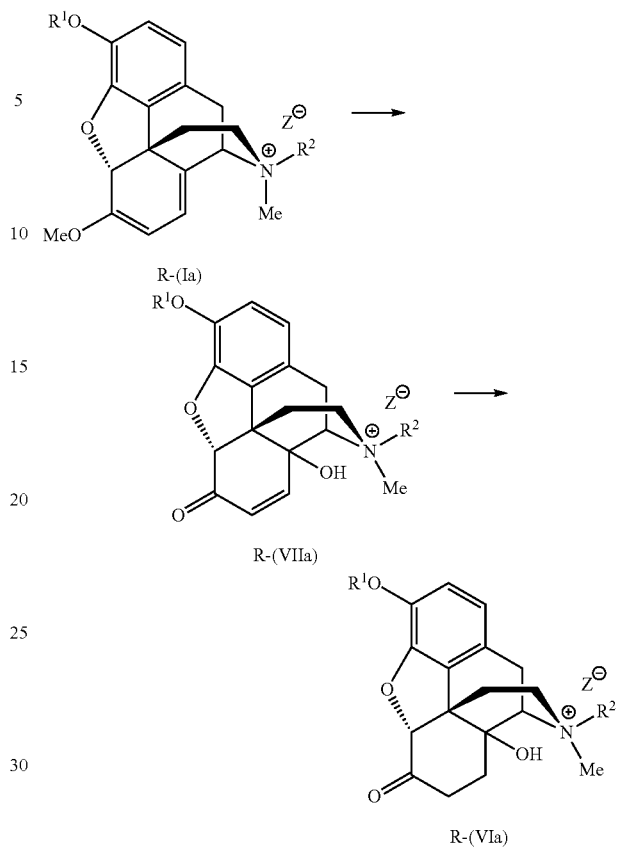

R-(Ia)

R-(VIIa)

R-(VIa)

wherein

R$^1$ is selected from hydrogen, C$_{1-6}$alkyl, C(O)C$_{1-6}$alkyl and PG;

R$^2$ is selected from R$^3$, C(O)R$^3$, S(O)R$^3$ and SO$_2$R$^3$;

R$^3$ is selected from C$_{1-6}$alkyl, C$_{1-6}$alkyleneC$_{3-8}$cycloalkyl, C$_{1-6}$alkyleneC$_{6-10}$aryl, C$_{1-6}$alkyleneC$_{1-8}$heterocyclyl and C$_{1-6}$alkyleneC$_{1-10}$heteroaryl;

PG is a protecting group;

Z is a suitable counter anion; and each alkyl, alkylene and aryl is optionally fluoro-substituted and/or deuterated.

The present application also includes a process of preparing S-methylnaltrexone, or analogs thereof of the formula S-(VIb), comprising:

(a) reacting a compound of the formula S-(Ib) with a per-acid under conditions to form a compound of formula S-(VIIb); and (b) reducing the compound of the formula S-(VIIb) under conditions to form a compound of the formula S-(VIb):

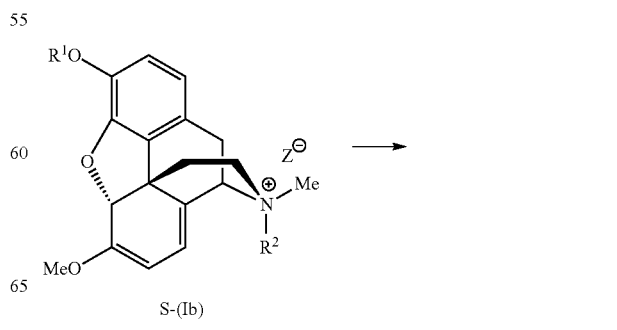

S-(Ib)

-continued

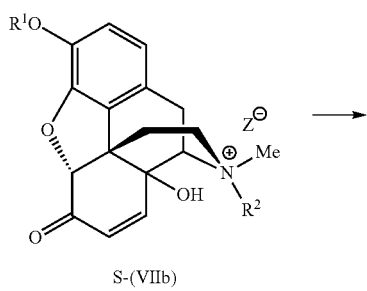

S-(VIIb)

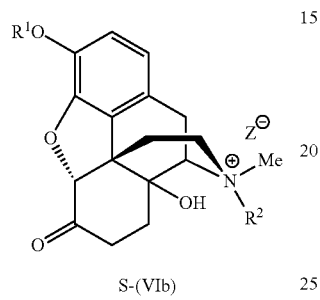

S-(VIb)

wherein

R$^1$ is selected from hydrogen, C$_{1-6}$alkyl, C(O)C$_{1-6}$alkyl and PG;

R$^2$ is selected from R$^3$, C(O)R$^3$, S(O)R$^3$ and SO$_2$R$^3$;

R$^3$ is selected from C$_{1-6}$alkyl, C$_{1-6}$alkyleneC$_{3-8}$cycloalkyl, C$_{1-6}$alkyleneC$_{6-10}$aryl, C$_{1-6}$alkyleneC$_{1-8}$heterocyclyl and C$_{1-6}$alkyleneC$_{1-10}$heteroaryl;

PG is a protecting group;

Z is a suitable counter anion; and each alkyl, alkylene and aryl is optionally fluoro-substituted and/or deuterated.

In a further embodiment of the present application, the compounds of formula (IV) are converted to morphinones and morphinanes, for example, but limited to, naltrexone, R-methylnaltrexone, nalbuphine, nalbuphone and buprenorphine, and analogs thereof. Accordingly, in a further embodiment, the present application includes a process for the synthesis of compounds of formula (VIII) comprising reacting the compounds of formula (IV) with a source of singlet oxygen or a peracid under conditions to form compounds of the formula (IX), which are reduced under conditions to form compounds of the formula (VIII):

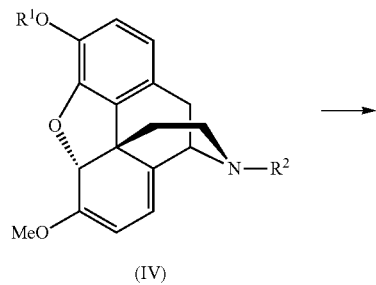

(IV)

-continued

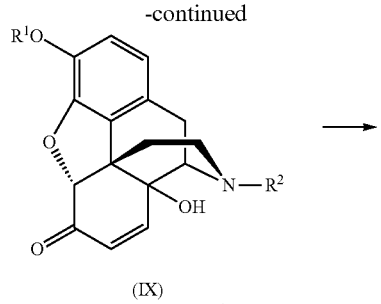

(IX)

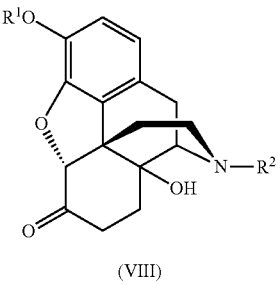

(VIII)

wherein

R$^1$ is selected from hydrogen, C$_{1-6}$alkyl, C(O)C$_{1-6}$alkyl and PG;

R$^2$ is selected from R$^3$, C(O)R$^3$, S(O)R$^3$ and SO$_2$R$^3$;

R$^3$ is selected from C$_{1-6}$alkyl, C$_{1-6}$alkyleneC$_{3-8}$cycloalkyl, C$_{1-6}$alkyleneC$_{6-10}$aryl, C$_{1-6}$alkyleneC$_{1-8}$heterocyclyl and C$_{1-6}$alkyleneC$_{1-10}$heteroaryl;

PG is a protecting group; and each alkyl, alkylene and aryl is optionally fluoro-substituted and/or deuterated.

Methylation of the compounds of formula (VIII) provides methylnaltrexone and analogs thereof, including R-methylnalbuphone, predominantly in the R-configuration.

In another embodiment of the present application, the compounds of formula (IV) are used in the preparation of buprenorphine or analogs thereof. In this embodiment, the compounds of formula (IV) are reacted with methyl vinyl ketone under [4+2] cycloaddition conditions, followed by reduction of the double bond, installation of an alkyl group in the C-7 pendant group using, for example, a Grignard reagent and removal of any protecting groups if needed, to provide buprenorphine or analogs thereof.

Accordingly, the application includes a process for preparing a compound of the formula (X), which includes buprenorphine and analogs thereof, comprising reacting a compound of the formula (IV) with methyl vinyl ketone under cycloaddition reaction conditions, followed by reduction under conditions to form a compound of the formula (XI) which is then reacted with a reagent of the formula (XII) under conditions to form a compound of the formula (X):

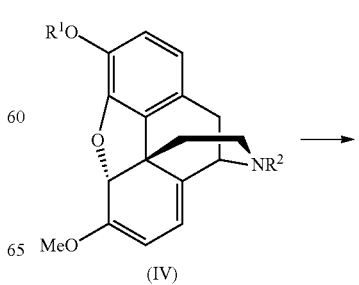

(IV)

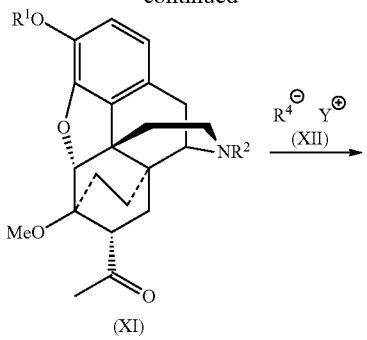

(XI)

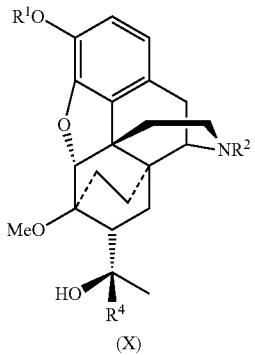

(X)

$R^1$ is selected from hydrogen, $C_{1-6}$alkyl and $C(O)C_{1-6}$alkyl and PG;

$R^2$ is selected from $R^3$, $C(O)R^3$, $S(O)R^3$ and $SO_2R^3$;

$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl;

$R^4$ is selected from $C_{1-6}$alkyl, $C_{3-8}$cycloalkyl and $C_{6-10}$aryl;

Y is a suitable counter cation; and each alkyl, alkylene and aryl is optionally fluoro-substituted and/or deuterated.

In another embodiment of the application there is included a compound of the formula R-(Va) or S-(Vb), or a mixture thereof:

R-(Va)

S-(Vb)

wherein $R^1$ is selected from hydrogen, $C_{1-6}$alkyl, $C(O)C_{1-6}$alkyl and PG;

$R^2$ is selected from $R^3$, $C(O)R^3$, $S(O)R^3$ and $SO_2R^3$;

$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl;

PG is a protecting group;

Z is a suitable counter anion; and each alkyl, alkylene and aryl is optionally fluoro-substituted and/or deuterated.

In an further embodiment of the present application, there is included a process to enrich a ratio of the R isomer of the formula R-(Ia) relative to S-isomer of the formula S-(Ib) as defined above comprising heating a mixture comprising the R-isomer of the formula (I) and the S-isomer of the formula (I) at about 100° C. to about 130° C. to selectively degrade the S-isomer and cooling to provide a cooled mixture and passing the cooled mixture through an alumina column to selectively absorb degradation products of the S-isomer and collecting the column eluent which comprises a mixture enriched in the R-isomer.

The present application also includes a method for separating a mixture of R- and S-isomer of methylnaltrexone comprising subjecting the mixture to HPLC or SMB chromatography.

The present application also includes a method of separating a mixture of R- and S-isomer of methylnaltrexone chloride comprising converting the methylnaltrexone chloride to a zwitterion and separating the mixture of R- and S-zwitterions by HPLC or SMB chromatography and converting the separated zwitterions to a bromide salt by addition of hydrobromic acid.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The application will now be described in greater detail with reference to the drawing in which:

FIG. 1 shows an example of a HPLC chromatogram of a mixture of (R,S)-methylnaltrexone and impurities ((R,S)-reduced methylnaltrexone).

DETAILED DESCRIPTION OF THE APPLICATION (i) Definitions

The following definitions, unless otherwise stated, apply to all aspects and embodiments of the present application.

As used herein, the term "alkyl" whether used alone or as part of a substituent group, includes straight and branched chains. For example, alkyl groups include methyl, ethyl, propyl, isopropyl, butyl, isobutyl, sec-butyl, t-butyl, pentyl and the like. Unless otherwise noted, "$C_{1-6}$" when used with alkyl means a straight or branched carbon chain composition of 1, 2, 3, 4, 5 or 6 carbon atoms.

The term "cycloalkyl" as used herein means a monocyclic or polycyclic saturated carbocyclic rings and includes, for example, cyclopropyl, cyclobutyl, cyclopentyl, bicyclo[2.2.2]octane, and the like.

The term "halo" as used herein means halogen and includes chloro, fluoro, bromo and iodo. The term "halide" as used herein means a halogen anion, including $Cl^-$, $Br^-$, $F^-$ and $I^-$.

The term "fluoro-substituted" as used herein means that one or more, including all, of the hydrogens on a group are replaced with fluorine. Examples of a fluoro-substituted alkyl group are $CF_3$, $CF_2CF_3$, $CH_2CF_3$ and the like. Examples of fluoro-substituted aryl groups are $C_6F_5$, $C_6H_4F$ and the like.

The term "deuterated" as used herein means that one or more, including all, of the hydrogens on a group are replaced with deuterium (I.e. [$^2H$]).

The term "aryl" as used herein refers to a cyclic or polycyclic carbocyclic ring systems containing at least one aromatic ring. In an embodiment, the aryl group is phenyl or naphthyl.

The term "heteroaryl" as used herein refers to aromatic cyclic or polycyclic ring systems having at least one heteroatom chosen from N, O, S, and P and at least one aromatic ring. For example, the heteroaryl groups include, but are not limited to, furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, and quinazolinyl, among others.

The term "heterocyclyl" includes non-aromatic rings or ring systems that contain at least one ring having at least one heteroatom (such as nitrogen, oxygen, sulfur or phosphorus). For example, the heterocyclyl groups include all of the fully saturated and partially unsaturated derivatives of the above mentioned heteroaryl groups. Examples of heterocyclic groups include, without limitation, pyrrolidinyl, tetrahydrofuranyl, morpholinyl, thiomorpholinyl, piperidinyl, piperazinyl, thiazolidinyl, isothiazolidinyl, and imidazolidinyl.

As would be understood by a person skilled in the art, when a heteroatom is part of a claimed grouping, the heteroatom may need to be substituted to fulfill the valency requirements of that atom. Typically such substituents will be a hydrogen atom, or a $C_{1-6}$alkyl group.

The suffix "ene" added on to any of the above groups means that the group is bivalent, i.e. inserted between two other groups.

The term "ring system" as used herein refers to ring structures that include monocycles, fused bicyclic and polycyclic rings, bridged rings and metalocenes.

The term "polycyclic" as used herein means cyclic groups that contain more than one ring linked together and includes, for example, groups that contain two (bicyclic), three (tricyclic) or four (quadracyclic) rings. The rings may be linked through a single bond, a single atom (spirocyclic) or through two atoms (fused and bridged).

The term "joined together" as used herein means that two substituents are linked together via a linker grouping to form a ring system. The linker grouping comprises at least one atom but may also comprise several atoms, for example up to 20 atoms, which optionally includes monocyclic and polycyclic ring systems.

The terms "protective group" or "protecting group" or "Pg" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protection group is typically removed under conditions that do not destroy or decompose the molecule. Many conventional protecting groups are known in the art for example as described in "Protective Groups in Organic Chemistry" McOmie, J. F. W. Ed., Plenum Press, 1973 and in Greene, T. W. and Wuts, P. G. M., "Protective Groups in Organic Synthesis", John Wiley & Sons, 3$^{rd}$ Edition, 1999. These include but are not limited to t-butyloxycarbonyl (t-Boc), tosylate (Ts), mesylate (Ms), brosylate, t-butyldimethylsilyl (TBDMS), tert-butyldiphenylsilyl (TBDPS), triflate (Tf), benzyl (Bn), allyl, fluorenylmethyloxycarbonyl (Fmoc), $C_{1-16}$acyl, acetal and counterions and the like. When the protecting group is a counterion, it may be a cation or anion depending on the group being protected. For example, protection of a hydroxy group as its anion requires the use of a suitable cation, such as an alkali metal cation (e.g. $Na^+$, $K^+$, and $Li^+$).

As used herein, unless otherwise noted, the term "antisolvent" refers to a solvent which does not dissolve a specific substance and is added to a solution of said substance, directly or by vapor diffusion, to cause precipitation of said substance.

The term "peracid" as used herein refers to a compound comprising the moiety "OOH" that acts as an oxidizing agent. The term "peracid" also includes mixtures of compounds wherein at least one compound comprises the moiety "OOH" and the mixture acts as an oxidizing agent.

The term "major isomer" as used herein refers to a stereochemical isomer that is the most abundant isomer in a mixture of isomers of the same compound. Conversely, the term "minor isomer" as used herein refers to a stereochemical isomer that is not the most abundant isomer in a mixture of isomers of the same compound In the processes of the application, it is typical for the compounds, including starting materials and products to be present as a mixture of isomers. For example, when it is shown that the R- or S-isomer is a product or starting material of a reaction, this means that that isomer is present in greater than 80%, 85%, 90%, 95%, 98% or 99% by weight based on the total amount of R- and S-isomers.

All of the processes described herein can be performed as batch or continuous processes. When continuous processes are used a person skilled in the art would appreciate that shorter reaction times and higher reaction temperatures can be used. For example, reaction temperatures for continuous processes can be 25° C., 50° C., 100° C., 150° C., or 200° C. higher than the corresponding reaction temperature for batch processes.

The term "suitable" as used herein means that the selection of the particular compound, group, atom or conditions would depend on the specific synthetic manipulation to be performed, and the identity of the molecule(s) to be transformed, but the selection would be well within the skill of a person trained in the art. All process steps described herein are to be conducted under conditions sufficient to provide the product shown. Unless otherwise indicated, a person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

The products of the processes of the application may be isolated according to known methods, for example, the compounds may be isolated by evaporation of the solvent, by filtration, centrifugation, chromatography or other suitable method.

One skilled in the art will recognize that where a reaction step of the present application is carried out in a variety of solvents or solvent systems, said reaction step may also be carried out in a mixture of the suitable solvents or solvent systems.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(ii) Processes of the Application (a) Preparation of Intermediates

The application includes a process for preparing intermediates useful in the synthesis of morphinane and morphinone compounds comprising:

(a) reacting a compound of the formula (II) with a compound of the formula (III) under conditions to form compounds of the formulae R-(Ia) and S-(Ib):

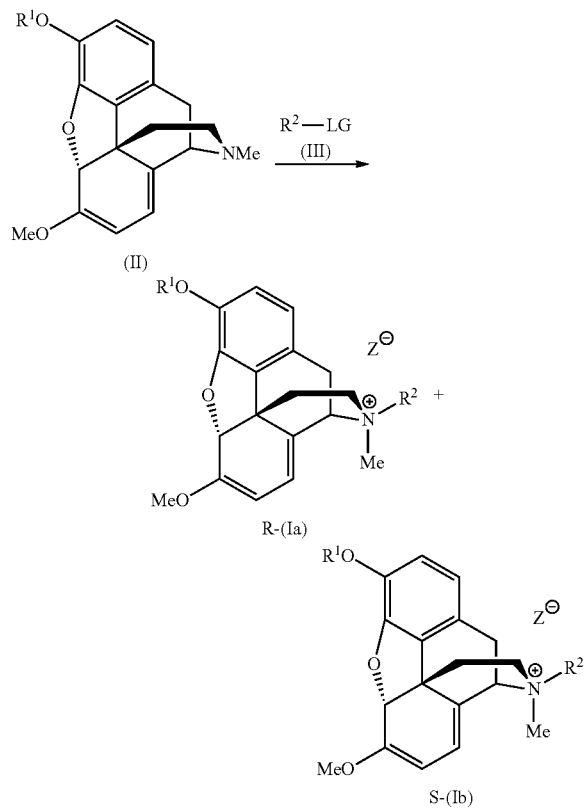

wherein
$R^1$ is selected from hydrogen, $C_{1-6}$alkyl, $C(O)C_{1-6}$alkyl and PG;
$R^2$ is selected from $R^3$, $C(O)R^3$, $S(O)R^3$ and $SO_2R^3$;
$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl;
LG is a leaving group;
PG is a protecting group;
Z is a suitable counter anion; and
each alkyl, alkylene and aryl is optionally fluoro-substituted and/or deuterated; and (b) optionally, isolating the compound of the formula R-(Ia); and (c) optionally, treating the compound of the formula S-(Ib), the compound of the formula R-(Ia) or a mixture of the compounds of the formulae R-(Ia) and S-(Ib) under N-demethylation conditions to form a compound of the formula (IV):

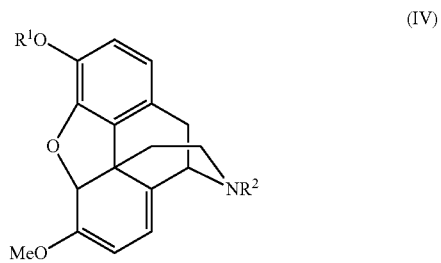

wherein
$R^1$ is selected from hydrogen, $C_{1-6}$alkyl, $C(O)C_{1-6}$alkyl and PG;
$R^2$ is selected from $R^3$, $C(O)R^3$, $S(O)R^3$ and $SO_2R^3$;
$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl;
LG is a leaving group;
PG is a protecting group; and
each alkyl, alkylene and aryl is optionally fluoro-substituted and/or deuterated.

In an embodiment of the application, the conditions to form the compounds of the formulae R-(Ia) and S-(Ib) comprise treating the compound of formula II in a suitable solvent at a temperature of about 40° C. to about 200° C., or about 60° C. to about 100° C., with addition of excess amounts (for example about 2 to about 20, suitably about 10 to about 15, molar equivalents, relative to the amount of the compound of formula (II)) of the compound of formula (III). In a further embodiment, the compound of formula (II) is reacted with excess amounts of a compound of formula (III) in suitable solvent at a temperature of about 40° C. to about 200° C., or about 60° C. to about 100° C., the reaction mixture is then cooled and treated with a suitable base, for example an alkali metal carbonate, followed by treatment with further amount of a compound of formula (III) and heating to a temperature of about 40° C. to about 200° C., or about 60° C. to about 100° C., to provide a final reaction mixture. In this latter embodiment, the final reaction mixture is cooled and is filtered to provide a product that comprises R-(Ia) the major isomer. The filtrate is then treated to precipitate, for example by addition of a non-polar solvent, such as toluene, ether, or equivalent, further product which comprises the S-isomer (Ib) as the major isomer.

Examples of suitable solvents for reacting the compound of the formula (II) with the compound of the formula (III) include, but are not limited to, chloroform, dichloromethane (DCM), N-methylpyrrolidone (NMP), acetonitrile, dimethylformamide (DMF), dimethylpropylidene urea (DMPU), dimethylacetamide, morpholine, hexamethylphosphoramide (HMPA), alcohols (for e.g., methanol, ethanol, 1-octanol), nitromethane, acetone, dioxane, 3-butanone, toluene, dimethyl sulfoxide (DMSO), naphthalene, dimethylbenzamide, ionic liquids (for e.g., ethylammonium nitrate, 1-butyl-3-methylimidazolium (BMIM) salt), fluorous phase, and any aliphatic, heteroaliphatic, heterocyclic (ring size 3-10 atoms), or carbocyclic (ring size 3-10 atoms) solvent, or mixtures thereof. In an embodiment, solvents include chloroform, N-methyl saturated heterocycles, (for e.g. NMP) and DMF. These latter solvents favor the precipitation of the more desirable R-isomer (compound of the formula R-(Ia)).

In a further embodiment, the reaction of the compound of the formula (II) with the compound of the formula (III) is performed at a temperature of about 40° C. to about 200° C., or about 60° C. to about 100° C., for about 1 minute to about 48 hours, about 10 minutes to 40 hours, about 1 hour to about 35 hours, about 2 hours to about 30 hours, about 10 hours to about 20 hours, or about 10 hours to about 15 hours. In a further embodiment the compound of the formula (III) is added to the compound of the formula (II) over a set period of time, in two or more portions or continuously.

In an embodiment of the application the R-(Ia) isomer is isolated using any known means, such as, but not limited to recrystallization, chromatography, differential precipitation and/or derivatization with another chiral molecule. In an embodiment, the use of DMF as the reaction solvent results in precipitation of the R-(Ia) isomer from the reaction mixture. In a further embodiment, the R-(Ia) isomer is obtained from a mixture of R- and S-isomers by recrystallization using DMF as the recrystallization solvent.

In an embodiment of the application, the N-demethylation conditions to form the compound of formula (IV) comprise treating the compound of the formula R-(Ia), the compound of the formula S-(Ib) or a mixture of the compound of the formula R-(Ia) and S-(Ib) with a suitable nucleophile under conditions to form the compound of the formula (IV). In an embodiment of the application, suitable nucleophiles include, but are not limited to, salts of halides, $RS^-$, $RSe^-$, $R_2N^-$, $R_3N$, $R_2P^-$, $RC(O)O^-$ or $RC(O)S^-$ or is $R_3N$, wherein R is any suitable aliphatic, heteroalkyl, cycloalkyl, heterocyclyl, aryl or heteroaryl group, or inorganic sulfur, selenium, phosphorous or nitrogen anionic salts or its neutral forms. In a further embodiment the nucleophile is a thiolate nucleophile such as salts of $C_{1-20}alkylS^-$ or $C_{6-18}arylS^-$ or an inorganic thiolate salt (e.g. $S_2^-$). In a still further embodiment the nucleophile is salt of $C_{6-15}alkylS^-$ or an inorganic thiolate salt (e.g. $S_2^-$). The salt is formed with any suitable cation, for example alkali metal cations or organic cations (such as tetraalkylammonium cations). In a further embodiment the thiolate salt is prepared by reacting the corresponding thiol with a strong base, such as sodium methoxide, sodium, lithium or potassium hydride and sodium, lithium or potassium carbonate.

In an embodiment of the application the N-demethylation conditions to form the compound of formula (IV) further comprise a suitable solvent at a temperature of about 40° C. to about 150° C., or about 60° C. to about 100° C. In an embodiment, the suitable solvent is dimethylsulfoxide (DMSO). In another embodiment, higher reaction temperatures are used, for example up to about 250° C. or 200° C., in continuous processes with shorter contact times.

In another embodiment of the present application, $R^1$ in the compounds of formulae R-(Ia), S-(Ib), (II) and (IV) is selected from hydrogen, methyl and $-C(O)-C_{1-4}alkyl$.

In another embodiment of the present application, $R^2$ in the compounds of formulae R-(Ia), S-(Ib), (III) and (IV) is $R^3$. In a further embodiment, $R^3$ is selected from $C_{1-4}alkyl$, $C_{1-4}alkyleneC_{3-6}cycloalkyl$, $C_{1-4}alkyleneC_{6-10}aryl$, $C_{1-4}alkyleneC_{3-6}heterocyclyl$ and $C_{1-6}alkyleneC_{6-10}heteroaryl$. In a further embodiment, $R^3$ is $C_{1-4}alkyleneC_{3-6}cycloalkyl$. In another embodiment, $R^3$ is $CH_2cyclopropyl$ or $CH_2cyclobutyl$.

In a further embodiment of the present application, Z in the compounds of formulae R-(Ia) and S-(Ib) is halogen, mesylate, tosylate or brosylate and the like. In a further embodiment Z is chlorine or bromine. In another embodiment Z is bromine.

In a further embodiment, LG is the compound of formula (III) is any suitable leaving group, for example, but not limited to halogen, such as bromine or chlorine, or mesylate, tosylate or brosylate and the like. Typically, the anionic LG becomes the counter anion Z.

(b) Conversion of Intermediated R-(Ia) and/or S-(Ib) to R-methylnaltrexone and/or S-methylnaltrexone and Analogs Thereof.

In an embodiment of the present application, the compounds of the formula R-(Ia) and/or S-(Ib) are converted to R-methylnaltrexone and/or S-methylnaltrexone and analogs thereof.

Accordingly, the present application also includes a process of preparing R-methylnaltrexone, or analogs thereof of the formula R-(VIa), comprising:

(a) reacting a compound of the formula R-(Ia) with a source of singlet oxygen under conditions to form a compound of the formula R-(Va); and (b) reducing the compound of the formula R-(Va) under conditions to form the compound of the formula R-(VIa) or reducing the compound of the formula R-(Va) under conditions to form the compound of the formula R-(VIIa) followed by reducing the compound of the formula R-(VIIa) under conditions to form the compound of the formula R-(VIa):

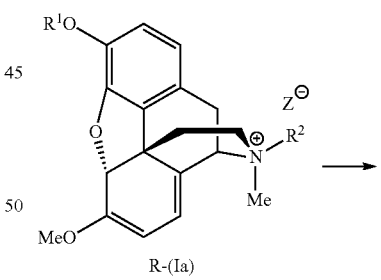

R-(Ia)

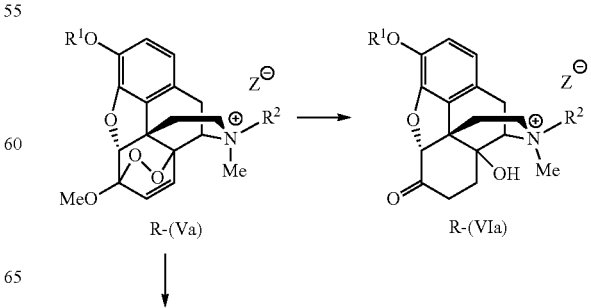

R-(Va)    R-(VIa)

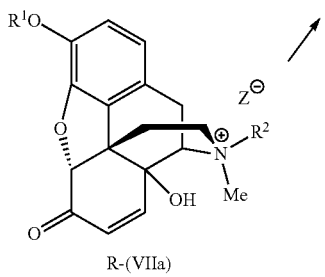

R-(VIIa)

wherein $R^1$ is selected from hydrogen, $C_{1-6}$alkyl, $C(O)C_{1-6}$alkyl and PG;

$R^2$ is selected from $R^3$, $C(O)R^3$, $S(O)R^3$ and $SO_2R^3$;

$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl;

PG is a protecting group;

Z is a suitable counter anion; and each alkyl, alkylene and aryl is optionally fluoro-substituted and/or deuterated, The present application also includes a process of preparing S-methylnaltrexone, or analogs thereof of the formula S-(VIb), comprising:

(a) reacting a compound of the formula S-(Ib) with a source of singlet oxygen under conditions to form a compound of the formula S-(Vb); and (b) reducing the compound of the formula S-(Vb) under conditions to form the compound of the formula S-(VIb) or reducing the compound of the formula S-(Vb) under conditions to form the compound of the formula S-(VIIb) followed by reducing the compound of the formula S-(VIIb) under conditions to form the compound of the formula S-(VIb):

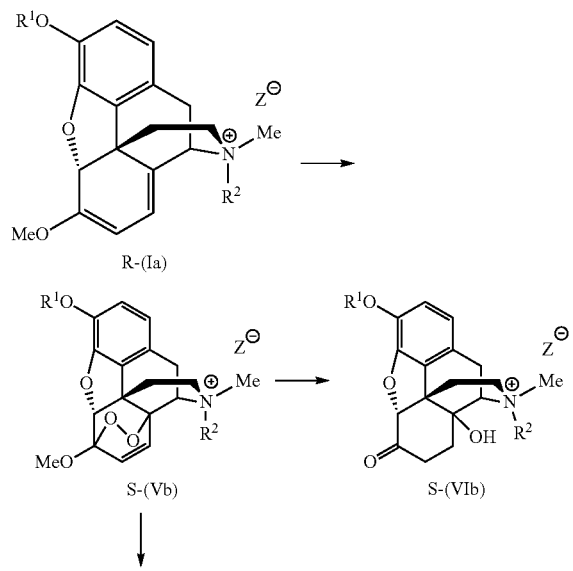

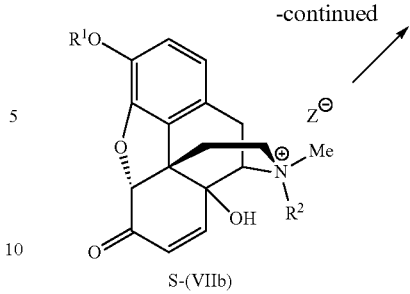

S-(VIIb)

wherein $R^1$ is selected from hydrogen, $C_{1-6}$alkyl, $C(O)C_{1-6}$alkyl and PG;

$R^2$ is selected from $R^3$, $C(O)R^3$, $S(O)R^3$ and $SO_2R^3$;

$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl;

PG is a protecting group;

Z is a suitable counter anion; and each alkyl, alkylene and aryl is optionally fluoro-substituted and/or deuterated.

In an embodiment, the source of singlet oxygen for the conversion of the compound of formula R-(Ia) or S-(Ia) to the compound of formula R-(VIa) or S-(VIb), respectively, is that provided using well-known photooxidation procedures (see, for example, CRC Handbook of Organic Photochemistry and Photobiology, Ed. William Horspool and Francesco Lenci, CRC Press, 2004). For example, using tetraphenylporphyrin (TPP), Rose Bengal, methylene blue or a porphyrin, or polymer-supported versions thereof, and oxygen gas in the presence of irradiation. Suitable solvents and reaction temperatures and reactant ratios are selected using known methods by a person skilled in the art. Accordingly, compounds of formula R-(Ia) or S-(Ia) are dissolved in a suitable solvent or mixture of solvents and photo-oxygenated, for example, by adding a photosensitizer and bubbling oxygen through the reaction mixture for several hours, while irradiating the mixture (e.g., with a lamp having a power output of about 10 W to about 5000 W, depending on the sensitizer, suitably having a power output of 500 W) to provide the endoperoxides (Va) or (Vb), respectively. Examples of solvents useful in the photo-oxygenation reaction include, but are not limited to, alcohols (e.g., methanol (MeOH), ethanol (EtOH), isopropanol, butanol (BuOH), 1-octanol), chloroform, dichloromethane (DCM), N-methyl-2-pyrrolidone (NMP), acetonitrile, dimethylformamide (DMF), morpholine, hexamethylphosphoramide (HMPA), nitromethane, acetone, dioxane, 3-butanone, toluene, dimethyl sulfoxide (DMSO), naphthalene, dimethylbenzamide, ionic liquids (e.g., ethylammonium nitrate, 3-methylimidazolium (BMIM) salt), fluorous phase, or any aliphatic, heteroaliphatic, heterocyclic (ring size 3-10 atoms), or carbocyclic (ring size 3-10 atoms) solvents, or mixtures thereof. In one embodiment, a mixture of a chlorinated solvent (e.g., chloroform, DCM) and an alcohol (e.g., MeOH, EtOH, isopropanol, BuOH, 1-octanol) is used. In a further embodiment, a mixture of DCM and MeOH is used. In an embodiment, the photo-oxygenation reaction is run at a temperature of about −40° C. to about 80° C., in a particular embodiment about 5° C. to about 15° C. In a further embodiment, alternative sources of singlet oxygen are used, for example that described in Nardello, Veronique et al. *Lanthanum(III)-catalyzed disproportionation of hydrogen peroxide: a heterogeneous generator of singlet molecular oxygen—$^1O_2$ (1D g)—in near-neutral aqueous and organic media for per-*

*oxidation of electron-rich substrates*. Chemistry-A European Journal (2003), 9(2), 435-441.

In an embodiment, the endoperoxide of formula R-(Va) or S-(Vb) is isolated by first precipitating the crude endoperoxide material by addition of a nonpolar solvent, such as diethyl ether or hexane. The precipitate is isolated by either filtration or centrifugation.

In a further embodiment, the conditions to form the compound of the formula R-(VIa) or S-(VIb) from the compound of the formula R-(Va) or S-(Vb), respectively, comprise any of the known methods for the hydrogenation of compounds, including for example, transfer hydrogenation, or the use of hydrogen gas in the presence of a catalyst, such as Pd/C or any of the well known transition metal hydrogenation catalysts or by the use of diimide. Suitable solvents and reaction temperatures and reactant ratios are selected using known methods by a person skilled in the art. In a specific embodiment embodiment, the conditions to form the compound of the formula R-(VIa) or S-(VIb) from the compound of the formula R-(Va) or S-(Vb), respectively, comprise dissolving the compound of the formula R-(Va) or S-(Vb) in a solvent or mixture of solvents with or without acid in the presence of a suitable hydrogenation catalyst. Examples of suitable acids include, for example, HCl, HBr, HI, $H_2SO_4$ and any other mineral acid, or any organic acids such as formic acid or acetic acid, or a mixture thereof. Examples of suitable hydrogenation catalysts include, for example, Pd, Pd(II), Pt, Rh and Ir and their derivatives. In a further embodiment, the reaction mixture is treated with hydrogen (for example at 1 atm or any other suitable pressures) at a temperature of about 0° C. to about 100° C. until complete consumption of the starting material has occurred. Examples of solvents useful in the hydrogenation reaction include, for example, alcohols, such as MeOH, EtOH, isopropanol, BuOH and 1-octanol, water, aqueous solutions of mineral acids and aqueous organic acids, such as formic acid and acetic acid, and mixtures thereof. In an embodiment, when the reaction is complete, the reaction mixture is filtered through a filter agent, such as Celite or silica, and the filtrate is concentrated to provide a crude product. In another embodiment, the crude product is purified by flash column chromatography or crystallization to provide the compound of formula R-(VIa) or S-(VIb).

In a further embodiment, the conditions to form the compound of the formula R-(VIIa) or S-(VIIb) from the compound of the formula R-(Va) or S-(Vb), respectively, comprise any of the known methods for the hydrogenation of compounds, including for example, transfer hydrogenation, or the use of hydrogen gas in the presence of a catalyst, such as Pd/C or any of the well known transition metal hydrogenation catalysts or by the use of diimide. Suitable solvents and reaction temperatures and reactant ratios are selected using known methods by a person skilled in the art. In a specific embodiment, the conditions to form the compound of the formula R-(VIIa) or S-(VIIb) from the compound of the formula R-(Va) or S-(Vb), respectively, comprise dissolving the compound of the formula R-(Va) or S-(Vb) in a solvent or mixture of solvents, with or without acid, in the presence of a suitable hydrogenation catalyst and a catalyst poison. Examples of suitable acids include HCl, HBr, HI, $H_2SO_4$ and any other mineral acid, or any organic acids such as formic acid or acetic acid. Examples of suitable hydrogenation catalysts include Pd, Pd(II), Pt, Rh and Ir and their derivatives. Examples of suitable catalyst poisons are known in the art and include, for example, sulfur compounds (such as elemental sulfur and thiourea), barium sulfate, lead salts (such as lead acetate or lead oxide) and quinoline. In a further embodiment, the reaction mixture is treated with hydrogen (for example at 1 atm or any other suitable pressures) at a temperature of about 0° C. to about 100° C. until complete consumption of the starting material has occurred. Examples of solvents useful in the hydrogenation reaction include, for example, alcohols, such as MeOH, EtOH, isopropanol, BuOH and 1-octanol, water, aqueous solutions of mineral acids and aqueous organic acids, such as formic acid and acetic acid, and mixtures thereof. In an embodiment, when the reaction is complete, the reaction mixture is filtered through a filter agent, such as Celite or silica, and the filtrate is concentrated to provide a crude product. In another embodiment, the crude product is purified by flash column chromatography or crystallization to provide the compound of formula R-(VIIa) or S-(VIIb).

In another embodiment, the conditions to form the compound of the formula R-(VIa) or S-(VIb) from the compound of the formula R-(VIIa) or S-(VIIb), respectively, comprise any of the known methods for the hydrogenation of compounds, including for example, transfer hydrogenation, or the use of hydrogen gas in the presence of a catalyst, such as Pd/C or any of the well known transition metal hydrogenation catalysts or by the use of diimide. Suitable solvents and reaction temperatures and reactant ratios are selected using known methods by a person skilled in the art. In a specific embodiment, the conditions to form the compound of the formula R-(VIa) or S-(VIb) from the compound of the formula R-(VIIa) or S-(VIIb), respectively, comprise dissolving the compound of the formula R-(VIa) or S-(VIb) in a solvent or mixture of solvents with or without acid in the presence of a suitable hydrogenation catalyst. Examples of suitable acids include, for example, HCl, HBr, $H_1$, $H_2SO_4$ and any other mineral acid, or any organic acids such as formic acid or acetic acid, or a mixture thereof. Examples of suitable hydrogenation catalysts include, for example, Pd, Pd(II), Pt, Rh and Ir and their derivatives. In a further embodiment, the reaction mixture is treated with hydrogen (for example at 1 atm or any other suitable pressures) at a temperature of about 0° C. to about 100° C. until complete consumption of the starting material has occurred. Examples of solvents useful in the hydrogenation reaction include, for example, alcohols, such as MeOH, EtOH, isopropanol, BuOH and 1-octanol, water, aqueous solutions of mineral acids and aqueous organic acids, such as formic acid and acetic acid, and mixtures thereof. In an embodiment, when the reaction is complete, the reaction mixture is filtered through a filter agent, such as Celite or silica, and the filtrate is concentrated to provide a crude product. In another embodiment, the crude product is purified by flash column chromatography or crystallization to provide the compound of formula R-(VIa) or S-(VIb).

It is an embodiment that the compound of formula R-(Ia) or S-(Ib) is converted to the compound of the formula R-(VIa) or S-(VIb), respectively, without isolation of the compound of formula R-(Va) or S-(Vb), respectively. Therefore crude compound of formula R-(Va) or S-(Vb) is reduced to compound of formula R-(VIa) or S-(VIb), respectively.

In a further alternate embodiment, the present application also includes a process of preparing R-methylnaltrexone, or analogs thereof of the formula (VIa), comprising:

(a) reacting a compound of the formula R-(Ia) with a peracid under conditions to form a compound of formula R-(VIIa); and (b) reducing the compound of the formula R-(VIIa) under conditions to form a compound of the formula R-(VIa):

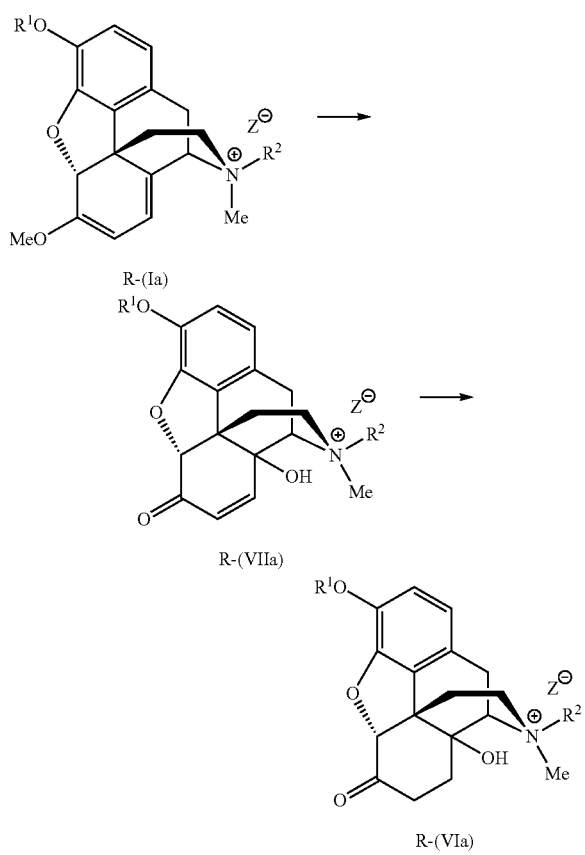

R-(Ia)

R-(VIIa)

R-(VIa)

wherein
R$^1$ is selected from hydrogen, C$_{1-6}$alkyl, C(O)C$_{1-6}$alkyl and PG;
R$^2$ is selected from R$^3$, C(O)R$^3$, S(O)R$^3$ and SO$_2$R$^3$;
R$^3$ is selected from C$_{1-6}$alkyl, C$_{1-6}$alkyleneC$_{3-8}$cycloalkyl, C$_{1-6}$alkyleneC$_{6-10}$aryl, C$_{1-6}$alkyleneC$_{1-8}$heterocyclyl and C$_{1-6}$alkyleneC$_{1-10}$heteroaryl;
PG is a protecting group;
Z is a suitable counter anion; and
each alkyl, alkylene and aryl is optionally fluoro-substituted and/or deuterated.

The present application also includes a process of preparing S-methylnaltrexone, or analogs thereof of the formula (VIb), comprising:
(a) reacting a compound of the formula S-(Ib) with a peracid under conditions to form a compound of formula S-(VIIb); and
(b) reducing the compound of the formula S-(VIIb) under conditions to form a compound of the formula S-(VIb):

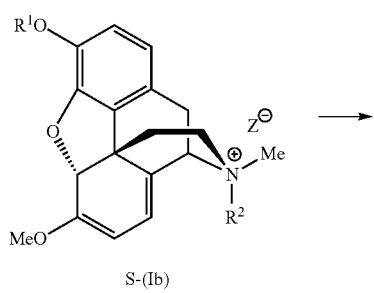

S-(Ib)

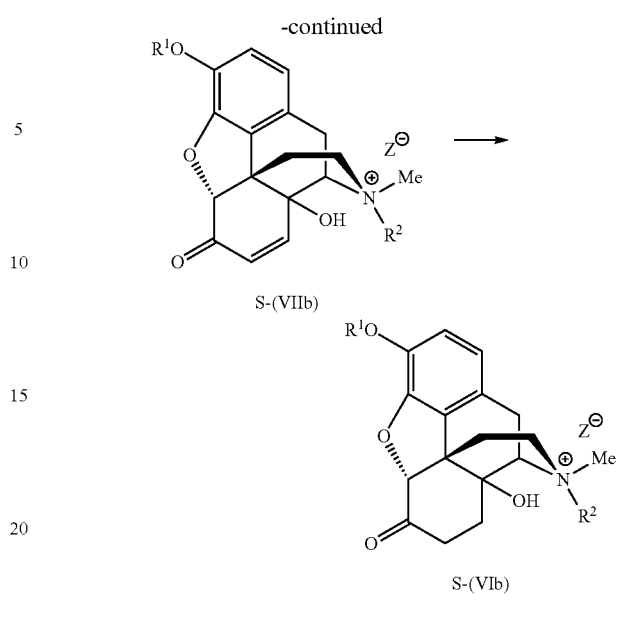

S-(VIIb)

S-(VIb)

wherein
R$^1$ is selected from hydrogen, C$_{1-6}$alkyl, C(O)C$_{1-6}$alkyl and PG;
R$^2$ is selected from R$^3$, C(O)R$^3$, S(O)R$^3$ and SO$_2$R$^3$;
R$^3$ is selected from C$_{1-6}$alkyl, C$_{1-6}$alkyleneC$_{3-8}$cycloalkyl, C$_{1-6}$alkyleneC$_{6-10}$aryl, C$_{1-6}$alkyleneC$_{1-8}$heterocyclyl and C$_{1-6}$alkyleneC$_{1-10}$heteroaryl;
PG is a protecting group;
Z is a suitable counter anion; and
each alkyl, alkylene and aryl is optionally fluoro-substituted and/or deuterated.

In this alternative embodiment of the application, the conditions for the formation of the compound of formula R-(VIIa) or S-(VIIb) from the compound of the formula R-(Ia) or S-(Ib), respectively, comprise dissolving the compound of the formula R-(Ia) or S-(Ib) in a suitable solvent or mixture of solvents and adding a peracid. In an embodiment the conditions for the formation of the compound of formula R-(VIIa) or S-(VIIb) from the compound of the formula R-(Ia) or S-(Ib), respectively further comprise a temperature of about −20° C. to about 50° C., or about −10° C. to about 20° C., and a time of about 10 minutes to about 10 hours, or about 1 hour to 3 hours. Examples of suitable peracids include performic acid, peracetic acid and m-chloroperbenzoic acid, hydrogen peroxide and Oxone™.

In this alternative embodiment, the conditions for the conversion of the compounds of formula R-(VIIa) or S-(VIIb) to a compound of formula R-(VIa) or S-(VIIb), respectively, are the same as those described herein above for the same conversion.

In another embodiment of the present application, R$^1$ in the compounds of formulae R-(Ia), S-(Ib), R-(Va), S-(Vb), R-(VIa), S-(VIb), R-(VIIa) and S-(VIIb) is selected from hydrogen, methyl and —C(O)—C$_{1-4}$alkyl.

In another embodiment of the present application, R$^2$ in the compounds of formulae R-(Ia), S-(Ib), R-(Va), S-(Vb), R-(VIa), S-(VIb), R-(VIIa) and S-(VIIb) is R$^3$. In a further embodiment, R$^3$ is selected from C$_{1-4}$alkyl, C$_{1-4}$-alkyleneC$_{3-6}$ cycloalkyl, C$_{1-4}$alkyleneC$_{6-10}$aryl, C$_{1-4}$alkyleneC$_{3-6}$ heterocyclyl and C$_{1-6}$alkyleneC$_{6-10}$heteroaryl. In a further embodiment, R$^3$ is C$_{1-4}$alkyleneC$_{3-6}$cycloalkyl. In another embodiment, R$^3$ is CH$_2$cyclopropyl or CH$_2$cyclobutyl.

In a further embodiment of the present application, Z in the compounds of formulae R-(Ia), S-(Ib), R-(Va), S-(Vb), R-(VIa), S-(VIb), R-(VIIa) and S-(VIIb) is halogen, mesylate, tosylate or brosylate and the like. In a further embodiment Z is chlorine or bromine. In another embodiment Z is bromine.

In the above processes for the preparation of compounds of formula R-(VIa) or S-(VIb) it is possible for the reactants and products [i.e. compounds of formula R-(Ia), S-(Ib), R-(Va), S-(Vb), R-(VIa), S-(VIb), R-(VIIa) and S-(VIIb)] to comprise a certain amount, for example, less than 20%, less than 15%, less than 10%, less than 5% or less than 1%, of alternate isomers. It is also possible for the reactants and products to comprise a racemic mixture of isomers [i.e. compounds of formula R-(Ia), S-(Ib), R-(Va), S-(Vb), R-(VIa), S-(VIb), R-(VIIa) and S-(VIIb)].

(c) Conversion of Intermediate (IV) to Morphinane and Morphinone Compounds

In a further embodiment of the present application, the compounds of formula (IV) are converted to morphinones and morphinanes, for example, but limited to, naltrexone, R-methylnaltexone, nalbuphine, nalbuphone and buprenorphine, and analogs thereof. Accordingly, in a further embodiment, the present application includes a process for the synthesis of compounds of formula (VIII) comprising reacting the compounds of formula (IV) with a source of singlet oxygen or a peracid under conditions to form compounds of the formula (IX), which are reduced under conditions to form compounds of the formula (VIII):

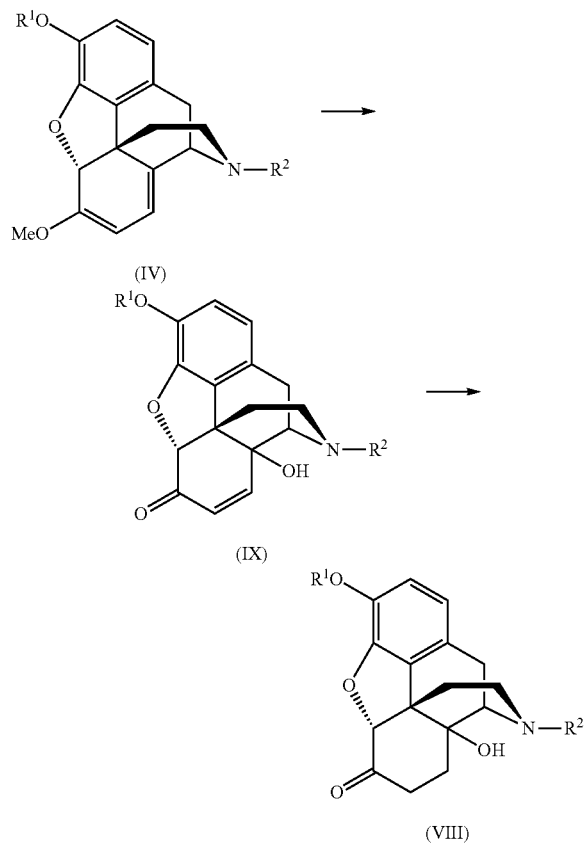

wherein
$R^1$ is selected from hydrogen, $C_{1-6}$alkyl, $C(O)C_{1-6}$alkyl and PG;
$R^2$ is selected from $R^3$, $C(O)R^3$, $S(O)R^3$ and $SO_2R^3$;
$R^3$ is selected from $C_{1-6}$alkyl, $C_{1-6}$alkyleneC_{3-8}cycloalkyl, $C_{1-6}$alkyleneC_{6-10}aryl, $C_{1-6}$alkyleneC_{1-8}heterocyclyl and $C_{1-6}$alkyleneC_{1-10}heteroaryl;
PG is a protecting group; and
each alkyl, alkylene and aryl is optionally fluoro-substituted and/or deuterated.

In an embodiment of the application, the conditions for the formation of the compound of formula (IX) from the compound of the formula (IV) comprise dissolving the compound of the formula (IV) in a suitable solvent or mixture of solvents and adding a peracid. In an embodiment the conditions for the formation of the compound of formula (IX) from the compound of the formula (IV) further comprise at a temperature of about −20° C. to about 50° C., or about −10° C. to about 20° C., and a time of about 10 minutes to about 10 hours, or about 1 hour to 3 hours. Examples of suitable peracids include, but are not limited to, performic acid, peracetic acid and m-chloroperbenzoic acid, hydrogen peroxide and Oxone™.

In an embodiment, the source of singlet oxygen for the conversion of the compound of formula (IV) to the compound of formula (IX) is that provided using well-known photooxidation procedures (see, for example, CRC Handbook of Organic Photochemistry and Photobiology, Ed. William Horspool and Francesco Lenci, CRC Press, 2004). For example, using tetraphenylporphyrin (TPP), Rose Bengal, methylene blue or a porphyrin, or polymer-supported versions thereof, and oxygen gas in the presence of irradiation. Suitable solvents and reaction temperatures and reactant ratios are selected using known methods by a person skilled in the art. Accordingly, compounds of formula (IV) are dissolved in a suitable solvent or mixture of solvents and photo-oxygenated, for example, by adding a photosensitizer and bubbling oxygen through the reaction mixture for several hours, while irradiating the mixture (e.g., with a lamp having a power output of about 10 W to about 5000 W, depending on the sensitizer, suitably having a power output of 500 W) to form compounds of the formula (IX). Examples of solvents useful in the photo-oxygenation reaction include, but are not limited to, alcohols (e.g., methanol (MeOH), ethanol (EtOH), isopropanol, butanol (BuOH), 1-octanol), chloroform, dichloromethane (DCM), N-methyl-2-pyrrolidone (NMP), acetonitrile, dimethylformamide (DMF), morpholine, hexamethylphosphoramide (HMPA), nitromethane, acetone, dioxane, 3-butanone, toluene, dimethyl sulfoxide (DMSO), naphthalene, dimethylbenzamide, ionic liquids (e.g., ethylammonium nitrate, 3-methylimidazolium (BMIM) salt), fluorous phase, or any aliphatic, heteroaliphatic, heterocyclic (ring size 3-10 atoms), or carbocyclic (ring size 3-10 atoms) solvents, or mixtures thereof. In one embodiment, a mixture of a chlorinated solvent (e.g., chloroform, DCM) and an alcohol (e.g., MeOH, EtOH, isopropanol, BuOH, 1-octanol) is used. In a further embodiment, a mixture of DCM and MeOH is used. In an embodiment, the photo-oxygenation reaction is run at a temperature of about −40° C. to about 80° C., in a particular embodiment about 5° C. to about 15° C. In a further embodiment, alternative sources of singlet oxygen are used, for example that described in Nardello, Veronique et al. *Lanthanum(III)-catalyzed disproportionation of hydrogen peroxide: a heterogeneous generator of singlet molecular oxygen*—$^1O_2$ (1D g)—*in near-neutral aqueous and organic media for peroxidation of electron-rich substrates.* Chemistry—A European Journal (2003), 9(2), 435-441.

It is an embodiment that the compound of the formula (IX) is not isolated but is treated directly, with or without removal of the reaction solvent, under conditions to form the compound of the formula (VIII). In another embodiment, the conditions to form the compound of the formula (VIII) from the compound of the formula (IX) comprise any of the known methods for the hydrogenation of compounds, including for example, transfer hydrogenation, or the use of hydrogen gas in the presence of a catalyst, such as Pd/C or any of the well known transition metal hydrogenation catalysts or by the use of diimide. Suitable solvents and reaction temperatures and reactant ratios are selected using known methods by a person skilled in the art. In a specific embodiment, the conditions to form the compound of the formula (VIII) from the compound of the formula (IX) comprise dissolving the compound of the formula (IX) in a solvent or mixture of solvents with or without acid in the presence of a suitable hydrogenation catalyst. Examples of suitable acids include, for example, HCl, HBr, HI, $H_2SO_4$ and any other mineral acid, or any organic acids such as formic acid or acetic acid, or a mixture thereof. Examples of suitable hydrogenation catalysts include, for example, Pd, Pd(II), Pt, Rh and Ir and their derivatives. In a further embodiment, the reaction mixture is treated with hydrogen (for example at 1 atm or any other suitable pressures) at a temperature of about 0° C. to about 100° C. until complete consumption of the starting material has occurred. Examples of solvents useful in the hydrogenation reaction include, for example, alcohols, such as MeOH, EtOH, isopropanol, BuOH and 1-octanol, water, aqueous solutions of mineral acids and aqueous organic acids, such as formic acid and acetic acid, and mixtures thereof. In an embodiment, when the reaction is complete, the reaction mixture is filtered through a filter agent, such as Celite or silica, and the filtrate is concentrated to provide a crude product. In another embodiment, the crude product is purified by flash column chromatography or crystallization to provide the compound of formula (VIII).

In another embodiment of the present application, $R^1$ in the compounds of formulae (IV), (IX) and (VIII) is selected from hydrogen, methyl and —C(O)—$C_{1-4}$alkyl.

In another embodiment of the present application, $R^2$ in the compounds of formulae (IV), (IX) and (VIII) is $R^3$. In a further embodiment, $R^3$ is selected from $C_{1-4}$alkyl, $C_{1-4}$alkylene$C_{3-6}$cycloalkyl, $C_{1-4}$alkylene$C_{6-10}$aryl, $C_{1-4}$-alkylene$C_{3-6}$ heterocyclyl and $C_{1-6}$alkylene$C_{6-10}$heteroaryl. In a further embodiment, $R^3$ is $C_{1-4}$alkylene$C_{3-6}$cycloalkyl. In another embodiment, $R^3$ is $CH_2$cyclopropyl or $CH_2$cyclobutyl.

Compounds of the formula (VIII) are intermediates that can be converted to, for example, R-methyl naltrexone or nalbuphine, or analogs thereof, using known procedures. For example, methylation of the compounds of formula (VIII) provides methylnaltrexone and analogs thereof, including R-methylnalbuphone, predominantly in the R-configuration. Representative examples of such preparations of R-methyl naltrexone are Goldberg et al. [U.S. Pat. No. 4,176,186], Cantrell et al. [WO2004/043964], Doshan, H. D. and Perez, J. [WO2006/127899], Wang et al., [WO 2008/109156], Dlubala et al. [WO 2008/034973, US 2008/0214817], and Weigl, Schaer and Stutz [WO2008/138605]. Representative examples of such preparations of nalbuphine are Kavka [U.S. Pat. No. 5,756,745], Cheng and Bentley [WO 2007/124114] and Bailey and Rezaie [US 2008188574]. Nalbuphone is converted to nalbuphine using known procedures, for example, in the presence of a suitable reducing agent.

In another embodiment of the present application, the compounds of formula (IV) are used in the preparation of buprenorphine or analogs thereof. In this embodiment, the compounds of formula (IV) are reacted with methyl vinyl ketone under [4+2] cycloaddition conditions, followed by reduction of the double bond, installation of an alkyl group in the C-7 pendant group using, for example, a Grignard reagent and removal of any protecting groups if needed, to provide buprenorphine or analogs thereof.

Accordingly, the application includes a process for preparing a compound of the formula (X), which includes buprenorphine and analogs thereof, comprising reacting a compound of the formula (IV) with methyl vinyl ketone under cycloaddition reaction conditions, followed by reduction under conditions to form a compound of the formula (XI) which is then reacted with a reagent of the formula (XII) under conditions to form a compound of the formula (X):

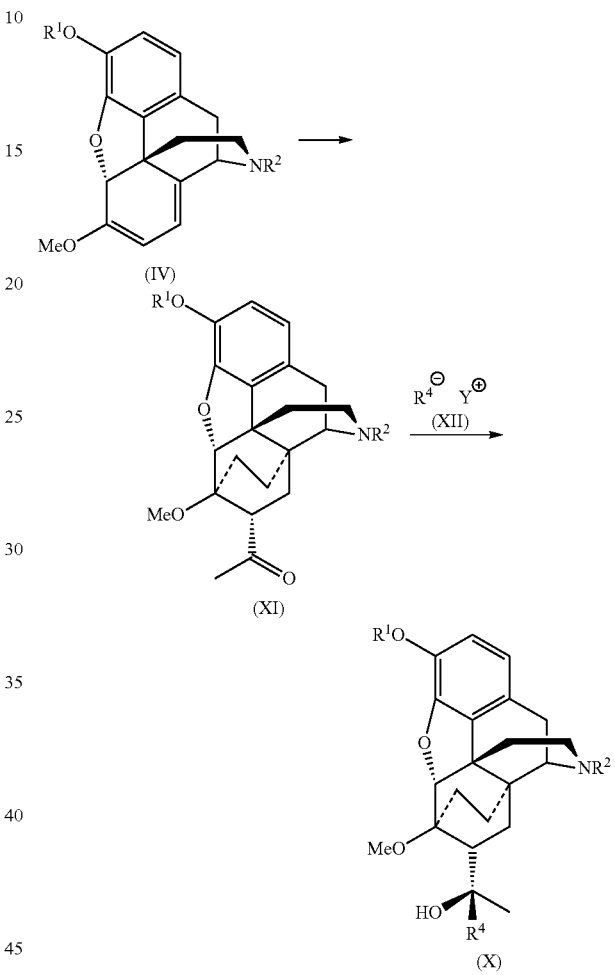

$R^1$ is selected from hydrogen, $C_{1-6}$alkyl and $C(O)C_{1-6}$alkyl and PG;
$R^2$ is selected from $R^3$, $C(O)R^3$, $S(O)R^3$ and $SO_2R^3$;
$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl;
$R^4$ is selected from $C_{1-6}$alkyl, $C_{3-8}$cycloalkyl and $C_{6-10}$aryl;
Y is a suitable counter cation; and
each alkyl, alkylene and aryl is optionally fluoro-substituted and/or deuterated.

In an embodiment of the present application, $R^1$ in the compounds of formulae (IV), (XI) and (X) is selected from hydrogen, methyl and —C(O)—$C_{1-4}$alkyl.

In another embodiment of the present application, $R^2$ in the compounds of formulae (IV), (XI) and (X) is $R^3$. In a further embodiment, $R^3$ is selected from $C_{1-4}$alkyl, $C_{1-4}$alkylene$C_{3-6}$cycloalkyl, $C_{1-4}$alkylene$C_{6-10}$aryl, $C_{1-4}$-alkylene$C_{3-6}$heterocyclyl and $C_{1-6}$alkylene$C_{6-10}$heteroaryl. In a further embodiment, $R^3$ is $C_{1-4}$alkylene$C_{3-6}$cycloalkyl. In another embodiment, $R^3$ is $CH_2$cyclopropyl or $CH_2$cyclobutyl.

In another embodiment of the application R[4] in the compounds of formulae (XII) and (X) is $C_{1-6}$alkyl.

In another embodiment of the application, Y in the compound of formula (XII) is Li or MgCl.

(e) Other Processes of the Application

In another embodiment, to obtain compounds of formula R-(Ia), S-(Ib), (VIa), (VIb), (VIIa) or (VIIb) wherein Z is Br, like in methylnaltrexone, if needed, the compound of formula R-(Ia), S-(Ib), (VIa), (VIb), (VIIa) or (VIIb) is dissolved in a minimum amount of solvent or solvent mixture, for example, water:MeOH (3:1), and filtered through an ion exchange column to exchange the counter ion to bromide. Alternatively, the counter ion is converted to the bromide by first converting the compound of formula R-(Ia), S-(Ib), (VIa), (VIb), (VIIa) or (VIIb) to the corresponding zwitterion by precipitating with potassium carbonate, and then adding hydrobromic acid to the zwitterions.

In an embodiment, the concentration of the R-isomer in a mixture can be increased relative to the S-isomer by selective thermal degradation of the S-isomer at 125° C., and then passing the mixture through a column, for example an alumina column to selectively absorb the degradation products of the S-isomer, thus producing a solution enriched in the R-isomer. In an further embodiment of the present application, there is included a process to enrich a ratio of the R-isomer of the formula (R-Ia) relative to S-isomer of the formula (S-Ib) as defined above comprising heating a mixture comprising the R-isomer of the formula (Ia) and the S-isomer of the formula (Ib) at about 100° C. to about 130° C. to selectively degrade the S-isomer and cooling to provide a cooled mixture and passing the cooled mixture through an alumina column to selectively absorb degradation products of the S-isomer and collecting the column eluent which comprises a mixture enriched in the R-isomer.

An embodiment of a process of the application will now be described with reference to Scheme 9.

Scheme 9

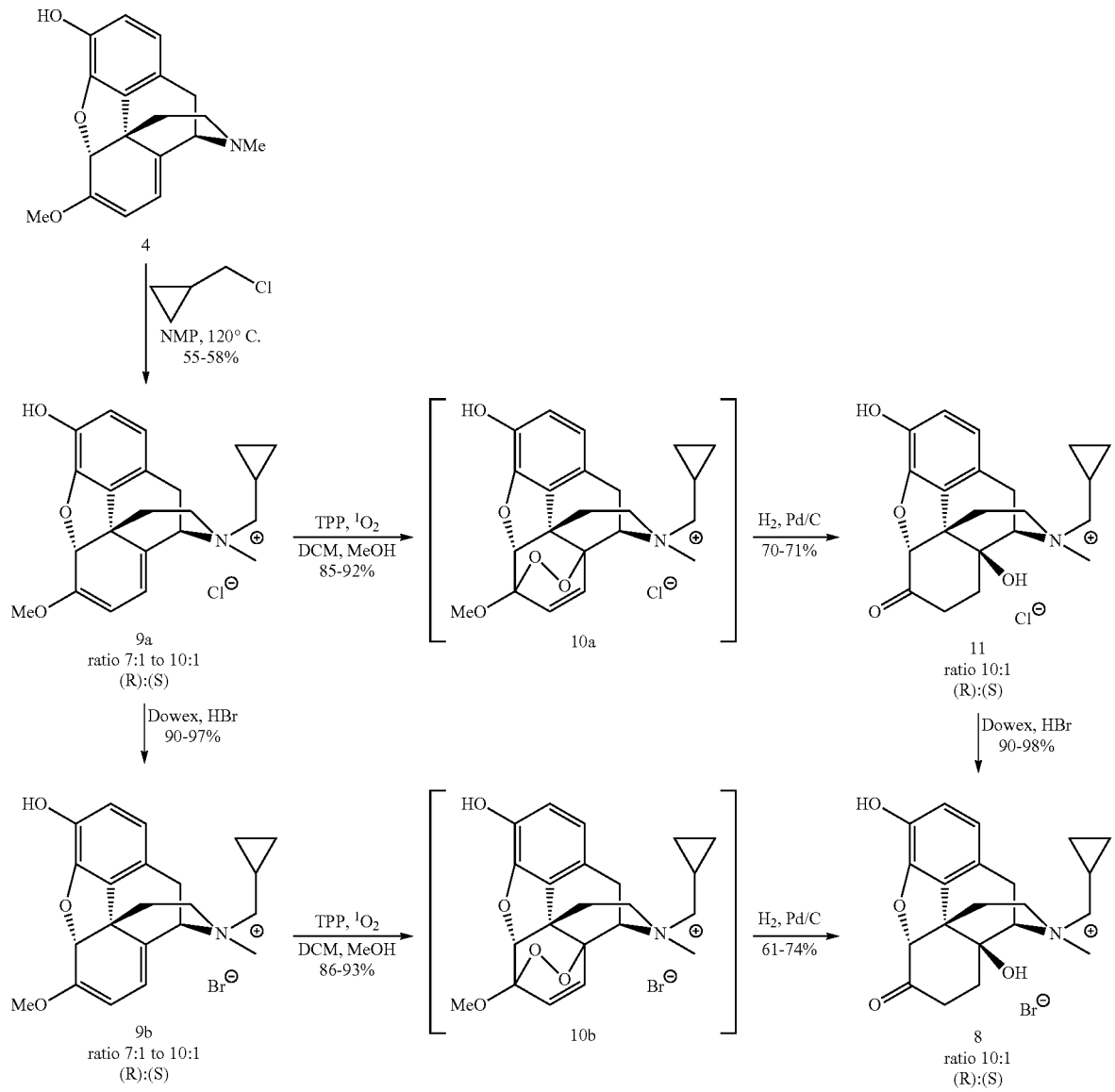

Suitable conditions for the conversion of quaternary ammonium salt 9a to endoperoxide 10a were developed. Hydrogenation of the endoperoxide intermediate furnished a mixture of methylnaltrexone chloride salts 11 in 70-71% yield. Exchange of the counter ion from chloride to bromide was achieved by ion exchange chromatography and furnished a mixture of (R)- to (S)-methylnaltrexone bromide in an approximate ratio of 10:1. Alternatively, the chloride counter ion was converted to the bromide by first converting the methylnaltrexone chloride to the corresponding zwitterion by precipitating with potassium carbonate, and then adding hydrobromic acid to the zwitterion [see Dlubala, WO 2008/034973, US 2008/0214817 for the conversion N-methylnaltrexone methylsulfate to N-methyl naltrexone bromide]. By following the same ion-exchange protocol, the conversion of the oripavine chloride salt 9a to the bromide salt 9b proceeded in excellent yield. Subsequent oxidation with singlet oxygen followed by hydrogenation gave N-methylnaltrexone bromide salt 8 in a similar overall yield compared to the results of the chloride series.

This three-step procedure for the conversion of oripavine 4 to methylnaltrexone 8 was applied successfully to thebaine 3 and 3-O-acetyl oripavine 12 to give the corresponding 3-O-substituted methylnaltrexone bromide derivatives 15 and 16 (Scheme 10).

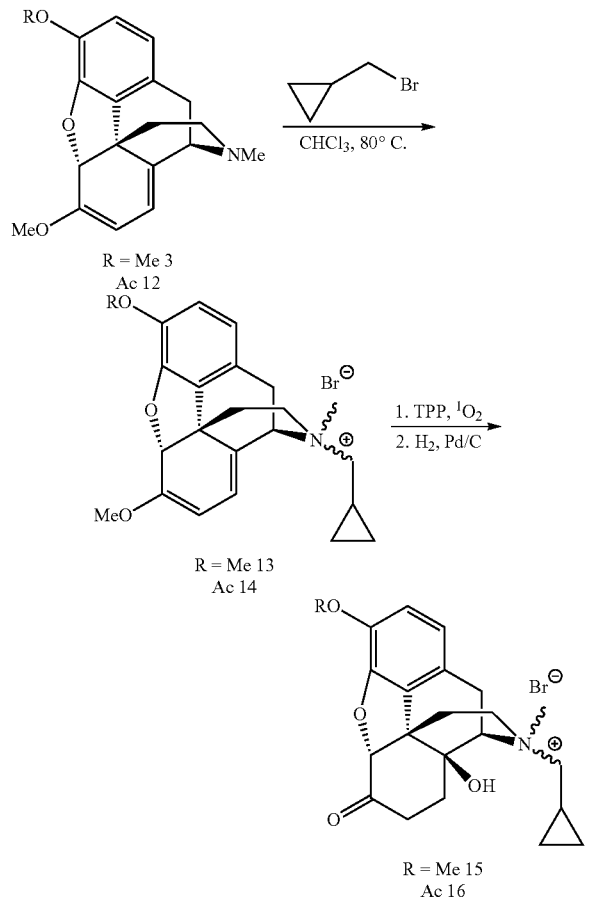

Scheme 10

Accordingly, in an embodiment of the application there is included an efficient high yielding synthesis of methylnaltrexone, and OMe and OAc analogs thereof, from readily available oripavine. Depending on the quaternization conditions applied, either isomer of these analogs of methylnaltrexone is prepared in enriched form.

In a further embodiment, the present application includes a process for preparing compounds of formula (VI), wherein $R^1$ is H and $R^2$ is cyclopropylmethylene as shown in Scheme 9.

Accordingly, oripavine (4) is reacted with an excess of cyclopropyl methylhalide, under conditions to provide N-cyclopropylmethylene-nororipavine methochloride (9a). In an embodiment, the reaction is conducted in an organic solvent at elevated temperature. In an embodiment of the application, the cyclopropylmethylhalide is present in an amount in the range of from about 2 to about 20 molar equivalents [relative to the amount of oripavine (4)] in a further embodiment, the cyclopropyl methylhalide is present in an amount in a range of from about 10 to about 15 molar equivalents, in still a further embodiment, the amount is about 15 molar equivalents. The reaction of oripavine (4) with cyclopropyl methylhalide is carried out neat or in an organic solvent. Examples of organic solvents which are used include, but are not limited to, chloroform, DCM, NMP, acetonitrile, DMF, DMPU, morpholine, HMPA, alcohols (e.g., MeOH, EtOH, 1-octanol), nitromethane, acetone, dioxane, 3-butanone, toluene, DMSO, naphthalene, dimethylbenzamide, ionic liquids (e.g., ethylammonium nitrate, BMIM) salt), fluorous phase, or any aliphatic, heteroaliphatic, heterocyclic (ring size 3-10 atoms), or carbocyclic (ring size 3-10 atoms) solvent, or mixtures thereof. In an embodiment, solvents include chloroform and N-methyl saturated heterocycles, such as NMP.

In an embodiment, the elevated temperature is a temperature of from about 80° C. to about 200° C., in an embodiment the temperature is about 80° C. to about 200° C. In a further embodiment the temperature is about 120° C., to yield the corresponding compound (9a).

In an embodiment the reaction time for the formation of (9a) is optimized to provide the more stable and desirable R-isomer, for example, for about 5 minutes to about 40 hours. In a further embodiment, the reaction time for the formation of (9a) is optimized to increase the proportion of the more stable and desirable R-isomer and is about 10 hours to about 15 hours.

In an embodiment, the concentration of the R-isomer in the mixture is increased relative to the S-isomer by selective thermal degradation of the S-isomer at 125° C., and then passing the mixture through an alumina column to selectively absorb the degradation products of the S-isomer, thus producing a solution enriched in the R-isomer.

The compound (9a) is then dissolved in a suitable solvent or mixture of solvents and photo-oxygenated, for example, by adding a photosensitizer (for example TPP Rose Bengal, methylene blue or a porphyrin, or polymer-supported versions thereof) and bubbling oxygen through the reaction mixture for several hours, while irradiating the mixture (e.g., with a lamp having a power output of about 10 W to about 5000 W, depending on the sensitizer, suitably having a power output of 500 W) to provide the endoperoxide (10a). Examples of solvents useful in this photo-oxygenation reaction include, but are not limited to, alcohols (e.g., MeOH, EtOH, isopropanol, BuOH, 1-octanol), chloroform, DCM, NMP, acetonitrile, DMF, morpholine, HMPA, nitromethane, acetone, dioxane, 3-butanone, toluene, DMSO, naphthalene, dimethylbenzamide, ionic liquids (e.g., ethylammonium nitrate, BMIM salt), fluorous phase, or any aliphatic, heteroaliphatic, heterocyclic (ring size 3-10 atoms), or carbocyclic (ring size 3-10 atoms) solvents, or mixtures thereof. In one embodiment, a mixture of a chlorinated solvent (e.g., chloroform, DCM) and an alcohol (e.g., MeOH, EtOH, isopropanol, BuOH, 1-octanol) is used. In a further embodiment, a mixture of DCM and MeOH is used. In an embodiment, the photo-oxygenation reaction is run at a temperature of about −40° C. to about 80° C., in a particular embodiment about 5° C. to about 15° C. In an alternate embodiment, the compound (9a) is then dissolved in a suitable solvent or mixture of solvents and oxidized, for example, by adding peracids such as performic, peracetic and m-chloroperbenzoic acids or other oxidizing agents such as hydrogen peroxide or Oxone™ to provide endoperoxide (10a).

In an embodiment, the endoperoxide (10a) is isolated by first precipitating the crude endoperoxide material by addition of a nonpolar solvent, such as diethylether or hexane. The precipitate is isolated by either filtration or centrifugation. The crude endoperoxide material is then dissolved in a solvent or mixture of solvents (e.g., water:isopropanol:formic acid) with or without the addition of acid in the presence of a suitable hydrogenation catalyst. Examples of suitable acids include HCl, HBr, HI, $H_2SO_4$ or any other mineral acid, or with any organic acids such as formic acid or acetic acid. Examples of a suitable hydrogenation catalyst include Pd, Pd(II), Pt, Rh and Ir and derivative thereof. The reaction mixture is treated with hydrogen (for example at 1 atm or at other pressures) at a temperature of about 0° C. to about 100° C. until complete consumption of the starting material has occurred. Examples of solvents useful in the hydrogenation reaction include alcohols, such as MeOH, EtOH, isopropanol, BuOH and 1-octanol, water, aqueous solutions of mineral acids and aqueous organic acids, such as formic acid, and acetic acid, and mixtures thereof. In an embodiment, the reaction mixture is then filtered through a filter agent, such as Celite or silica, and the filtrate is concentrated. In another embodiment, the product is purified by flash column chromatography or crystallization to provide the compound (11).

In an embodiment, compound (11) is dissolved in a minimum amount of solvent or solvent mixture, for example, water:MeOH (3:1), and filtered through an ion exchange column to exchange the counter ion from chloride to bromide to provide MNTX, compound (8). Alternatively, the chloride counter ion may be converted to the bromide by first converting compound (11) to the corresponding zwitterion by precipitating with potassium carbonate, and then adding hydrobromic acid to the zwitterion to provide MNTX, compound (8).

Alternatively, in another embodiment, compound (9a) is dissolved in a minimum amount of solvent or solvent mixture, such as water:methanol (3:1) and filtered through an ion-exchange column to exchange the counterion from chloride to bromide to provide compound (9b). Alternatively, the chloride counter ion may be converted to the bromide by first converting compound (9a) to the corresponding zwitterion by precipitating with potassium carbonate, and then adding hydrobromic acid to the zwitterion to provide MNTX, compound (9b).

In another embodiment of the present application, the compound (9b) is dissolved in a suitable solvent or mixture of solvents and photo-oxygenated, for example, by adding a photosensitizer (for example TPP Rose Bengal, methylene blue or a porphyrin, or polymer-supported versions thereof) and bubbling oxygen through the reaction mixture for several hours, while irradiating the mixture (e.g., with a lamp having a power output of about 10 W to about 5000 W, depending on the sensitizer, suitably having a power output of 500 W) to provide the endoperoxide (10b). Examples of solvents useful in this photo-oxygenation reaction include alcohols, for example MeOH, EtOH, isopropanol, butanol and 1-octanol, chloroform, DCM, NMP, acetonitrile, DMF, morpholine, HMPA, nitromethane, acetone, dioxane, 3-butanone, toluene, DMSO, naphthalene, dimethylbenzamide, ionic liquids, for example ethylammonium nitrate and BMIM salt, fluorous phase, or any aliphatic, heteroaliphatic, $C_{3-10}$heterocyclic, or $C_{3-10}$-carbocyclic solvents, or mixtures thereof. For example, a mixture of a chlorinated solvent, for example chloroform, DCM and an alcohol for example MeOH, EtOH, isopropanol, BuOH or 1-octanol is used; or, a mixture of DCM and MeOH is used. In an embodiment, the photo-oxygenation reaction is run at a temperature of about −40° C. to about 80° C., for example, about 5° C. to about 15° C. In another embodiment, the compound (9a) is dissolved in a suitable solvent or mixture of solvents and oxidized, for example, by adding peracids such as performic, peracetic and m-chloroperbenzoic acids or other oxidizing agents such as hydrogen peroxide or oxone to provide endoperoxide (10b).

In an embodiment, the endoperoxide (10b) is isolated by first precipitating the crude endoperoxide material by addition of a nonpolar solvent, such as diethylether or hexane. The precipitate is isolated by either filtration or centrifugation. The crude endoperoxide material is then dissolved in a solvent or mixture of solvents (e.g., water:isopropanol:formic acid) with or without the addition of acid in the presence of a suitable hydrogenation catalyst. Examples of suitable acids include HCl, HBr, HI, $H_2SO_4$ or any other mineral acid, or with any organic acids such as formic acid or acetic acid. Examples of a suitable hydrogenation catalyst include Pd, Pd(II), Pt, Rh and Ir, and derivatives thereof. The reaction mixture is treated with hydrogen (for example at 1 atm or at other pressures) at a temperature of about 0° C. to about 100° C. until complete consumption of the starting material has occurred. Examples of solvents useful in the hydrogenation reaction include alcohols, such as MeOH, EtOH, isopropanol, BuOH and 1-octanol, water, aqueous solutions of mineral acids and aqueous organic acids, such as formic acid, and acetic acid, or mixtures thereof. In an embodiment, the reaction mixture is then filtered through a filter agent, such as Celite or silica, and the filtrate is concentrated. In another embodiment, the product is purified by flash column chromatography or crystallization to provide MNTX compound (8) as a mixture containing ratios of R to S diastereomers anywhere from 1:3 to 18:1.

In an embodiment, the desired R-diastereomer is separated from the S-diastereomer by high performance liquid chromatography (HPLC) or variations such as simulated moving bed (SMB) chromatography.

A further embodiment of a process of the present application, will now be described with reference to Examples 12 and 14 and Scheme 11 hereinbelow. Suitable conditions for the demethylation of cyclopropylmethylene (9b) and cyclobutylmethylene (18) oripavine were developed. Initially a solution comprising an alkyl thiolate, such as dodecanethiolate, is prepared by reacting the corresponding alkylthiol with about 1 equivalent of a strong base, such as sodium ethoxide, in a suitable solvent, such as DMSO. The resulting mixture is stirred and heated to a temperature of about 80° C. to about 100° C., suitably about 90° C., for about 5 minutes to about 30 minutes, suitably about 10 minutes, prior to decreasing the temperature to about 70° C. to about 90° C., suitably about 80° C., for the addition of a solution of N-cyclopropylmethylene oripavine ammonium bromide (9b) or N-cyclobutylmethylene oripavine ammonium bromide (18) in the suitable solvent at room temperature, over about 5 minutes to about 20 minutes, suitably about 10 minutes. Either the R- or the S-isomers of (9b) and (18) or a mixture thereof can be used in this process. The reaction mixture is stirred until substantially complete consumption of the starting material is observed, for example by HPLC. Then the reaction mixture is cooled to room temperature and quenched, for example with water, and the pH of the aqueous mixture is adjusted to acidic pH (for example about pH=2) and washed with a non-polar solvent such as hexanes. The pH of the aqueous mixture is then adjusted to basic pH (for example pH=8) and the desired product is extracted into an organic solvent (for example EtOAc). This latter process of adjusting the aqueous fraction to basic pH followed by extraction with an organic solvent is optionally repeated. The organic layers are combined, optionally washed, for example with water and brine, optionally dried, and the desired product, N-cyclopropylmethylene nor-oripavine (17) or N-cyclobutylmethylene nor-oripavine (19) isolated by known methods.

The N-alkyl nor-oripavine compounds, for example (17) and (19), are useful intermediates for the preparation of morphinane and morphinone compounds. For example, as shown in Example 13 and in Scheme 11 hereinbelow, compounds (17) and (19) can be reacted with a peracid, for example peracetic acid, in a suitable solvent, for example aqueous acetic acid, at a temperature of about −5° C. to about 10° C., suitably about 5° C. The resulting intermediate compound is isolated or the reaction mixture is diluted with an alcoholic solvent, such as isopropanol and treated under hydrogenation conditions, for example using palladium on carbon in a hydrogen atmosphere at room temperature until hydrogenation is complete, for example about 5 hours to about 25 hours, or as determined, for example, by HPLC. The mixture is filtered through a pad of celite and washed with alcohol and the product isolated using known methods. The product of this reaction sequence is naltrexone [from (17)] or nalbuphone [from (19)]. Naltrexone and nalbuphone are converted to other morphinane and morphinone compounds, such as R-methyl-naltrexone and nalbuphine using known methods.

The N-alkyl nor-oripavine compounds, for example (17) and (19), are also converted to buprenorphine and analogs thereof using known methods as shown in Example 15 hereinbelow.

(iii) Compounds of the Application

The reaction of the compound of the formula R-(Ia) and S-(Ib) with a source of singlet oxygen results in the formation of novel intermediate endoperoxide compounds of the formulae R-(Va) and S-(Vb). Accordingly, in another embodiment of the application there is included a compound of the formula R-(Va) or S-(Vb), or a mixture thereof:

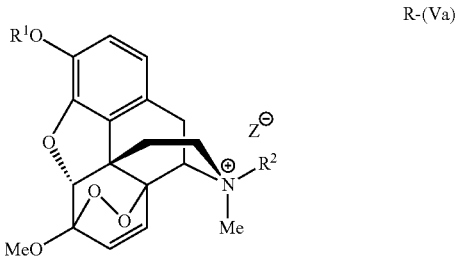

R-(Va)

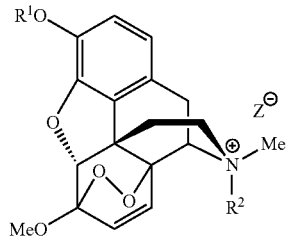

S-(Vb)

wherein
$R^1$ is selected from hydrogen, $C_{1-6}$alkyl, $C(O)C_{1-6}$alkyl and PG;
$R^2$ is selected from $R^3$, $C(O)R^3$, $S(O)R^3$ and $SO_2R^3$;
$R^3$ is selected from $C_{1-6}$alkyl, $C_{1-6}$alkylene$C_{3-8}$cycloalkyl, $C_{1-6}$alkylene$C_{6-10}$aryl, $C_{1-6}$alkylene$C_{1-8}$heterocyclyl and $C_{1-6}$alkylene$C_{1-10}$heteroaryl;
PG is a protecting group;
Z is a suitable counter anion; and
each alkyl, alkylene and aryl is optionally fluoro-substituted and/or deuterated.

In another embodiment of the present application, $R^1$ in the compound of formula R-(Va) or S-(Vb) is selected from hydrogen, methyl and —C(O)—$C_{1-4}$alkyl.

In another embodiment of the present application, $R^2$ in the compound of formula R-(Va) or S-(Vb) is $R^3$. In a further embodiment, $R^3$ is selected from $C_{1-4}$alkyl, $C_{1-4}$alkylene$C_{3-6}$ cycloalkyl, $C_{1-4}$alkylene$C_{6-10}$aryl, $C_{1-4}$-alkylene$C_{3-6}$heterocyclyl and $C_{1-6}$alkylene$C_{6-10}$heteroaryl. In a further embodiment, $R^3$ is $C_{1-4}$alkylene$C_{3-6}$cycloalkyl. In another embodiment, $R^3$ is $CH_2$cyclopropyl or $CH_2$cyclobutyl.

In a further embodiment of the present application, Z in the compound of formula R-(Va) or S-(Vb) is halogen, mesylate, tosylate or besylate and the like. In a further embodiment Z is chlorine or bromine. In another embodiment Z is bromine.

EXAMPLES

The following Examples are set forth to aid in the understanding of the application, and are not intended and should not be construed to limit in any way the application set forth in the claims which follow thereafter.

Materials and Methods

Liquid reagents were distilled prior to use, while other commercial solids were used as supplied. $^1$H-, and $^{13}$C-NMR spectra were recorded on a Bruker (300 MHz or 600 MHz) spectrometer. All chemical shifts are referenced to tetramethylsilane (TMS) or residual undeuterated solvent (CHCl$_3$, MeOH, H$_2$O) and coupling constants are quoted in Hz. Infrared analyses of liquid compounds were recorded as a thin film on NaCl plates and of solid compounds as KBr discs. Analytical thin-layer chromatography (TLC) was performed on Silicycle 60 Å 250 μm TLC plates with F-254 indicator. Flash column chromatography was performed using Natland 200-400 mesh silica gel. Melting points were recorded on a Hoover Unimelt apparatus and are uncorrected. Mass spectra were recorded on Kreatus/Msl Concept 1S mass spectrometer.

Examples 1-4 refer to the compounds shown in Scheme 9.

Example 1

N-cyclopropylmethylene-nororipavine methylchloride 9a

To a suspension of oripavine (4) (200 mg; 0.67 mmol) in NMP (3.5 mL) was added (chloromethyl)cyclopropane (0.93 mL; 10.09 mmol) and the reaction mixture was heated in a preheated oil bath at 120° C. for 28 hrs, before it was cooled down to room temperature. The black liquid was filtered through a plug of neutral alumina, and eluted with dichloromethane:MeOH (9:1) followed by elution with MeOH. The organic solvent was removed under reduced pressure. The brown residue was dissolved in MeOH and precipitated with diethylether to give the title compound 9a (148 mg, 55%) as a brown solid. $R_f$ 0.41 ($CH_2Cl_2$:MeOH 4:1); mp above 210° C. (MeOH:diethylether); isomeric ratio by HPLC(R:S) 7:1; IR (KBr) 3420, 3196, 3007, 1664, 1591, 1459, 1385, 1244 $cm^{-1}$; $^1$H NMR (600 MHz, $D_2O$)R-isomer=6.67 (d, J=8.4 Hz, 1 H), 6.62 (d, J=8.4 Hz, 1 H), 5.89 (d, J=6.6 Hz, 1 H), 5.41 (s, 1 H), 5.14 (d, J=6.6 Hz, 1 H), 4.54 (d, J=7.2 Hz, 1 H), 3.52-3.63 (m, 5 H), 3.04-3.35 (m, 7 H), 2.44-2.65 (m, 1 H), 1.81 (d, J=13.2 Hz, 1 H), 1.06-1.12 (m, 1 H), 0.71-0.79 (m, 2 H), 0.41-0.45 (m, 2 H) ppm; $^{13}$C NMR (600 MHz, $D_2O$)R-isomer=153.7, 142.5, 138.8, 131.8, 123.2, 122.8, 120.8, 120.2, 117.7, 96.3, 87.8, 68.4, 68.3, 55.3, 54.4, 46.1, 43.9, 30.9, 30.3, 4.4, 3.5, 3.4 ppm; MS ($FAB^+$) 739 [($C_{22}H_{26}NO_3)_2Cl]^+$; HRMS ($FAB^+$) calcd for $(C_{22}H_{26}NO_3)^+$ 352.1907, found 352.1821.

Initial reactions of oripavine and cyclopropylmethylbromide in chloroform in a sealed tube at 80° C. gave a mixture of quaternized oripavine salts in a ratio of 2.26 to 1 in favor of the (S)-isomer in nearly quantitative yield. A wide number of reaction conditions were screened and it was found that the use of NMP and cyclopropylmethylchloride at elevated temperatures significantly increased the ratio of the desired (R)-isomer, as shown in Table 1.

A detailed time study of the quaternization reaction of oripavine with 15 equivalents of cyclopropylmethylchloride in NMP at 120° C. revealed that the (S)-isomer of quaternized oripavine decomposed at a faster rate than the desired (R)-isomer (see FIG. 2). Therefore the (R)-isomer is isolated in a favorable ratio at prolonged reaction times. The maximum yield of the desired (R)-isomer of quaternized oripavine is around 50-55% yield after 10-15 hours of reaction time. However using a continuous addition of cyclopropylmethylchloride, the desired (R)-isomer was obtained in a ratio 18:1 over the (S)-isomer.

Example 2

N-cyclopropylmethylene-nororipavine methylbromide 9b

Compound 9a (150 mg, 0.39 mmol) dissolved in minimum amount of $H_2O$:MeOH, 3:1 was filtered through a column packed with Dowex®-1 resin (Sigma, strongly basic bromine loaded, 50-100 mesh) and eluted with dist. $H_2O$ (500 mL). The majority of the solvent was removed under reduced pressure. The residue was lyophilized to give the title compound 9b as a white solid (159 mg, 95%). $^1$H and $^{13}$C NMR spectra were identical to spectra of compound 9a. MS ($FAB^+$) 785 $[(C_{22}H_{26}NO_3)_2Br]^+$.

Having established efficient conditions for the preparation of the desired (R)-isomer of oripavine cyclopropylmethylchloride salt, the hydroxyl functionality at the C-14 of oripavine can be introduced. Numerous conditions, which have been reported to affect the conversion of thebaine to oxycodone as well as alternative oxidative conditions were screened [a) Freund, M.; Speyer, E. *J. Prakt. Chem.* 1916, 94, 135-178; b) Gates, M.; Boden, R. M.; Sundararaman P. *J. Org. Chem.* 1989, 54, 972-974; c) Hosztafi, S.; Simon, C.; Makleit, S. *Syn. Comm.* 1992, 22, 2527-2541; d) Hauser, F. M.; Chen, T.-K.; Carroll, F. I. *J. Med. Chem.* 1974, 17, 1117; e) Iijima, I.; Minamikawa, J.; Jacobson, A. E.; Brossi, A.; Rice, K. C.; Klee, W. A. *J. Med. Chem.* 1978, 21, 398-400; f) Zhang, A.; Csutoras, C.; Zong, R.; Neumeyer, J. L. *Org. Lett.* 2005, 7, 3239-3242]. Only small amounts of the desired α,β-unsaturated ketone derivatives were detected by HPLC under these conditions. The high polarity of the quaternary ammonium salts made the purification arduous and therefore alternative oxidative conditions were explored.

Example 3

General Procedure for the Photo-xygenation Reaction

To a solution of the quaternized morphine alkaloid (0.25-0.30 mmol) in dichloromethane-MeOH (4:1) (8 mL) in a double glass wall mini reactor was added tetraphenylporphyrin (20 mg). Oxygen was bubbled through the reaction mixture for 4 hours, while irradiated from a distance of 30 cm with a street lamp (500 W) at a reaction temperature of 5-15° C. The strongly coloured solution was transferred to an Erlenmeyer flask and the corresponding endoperoxide was precipitated by the addition of diethylether. The slightly purple solid was dissolved in MeOH and precipitated with diethylether to afford the corresponding endoperoxide opioid as slightly coloured solid. Because of the instability of the endoperoxide intermediates, only $^1$H NMR data was obtained.
(a) Endoperoxide Oripavine Cl-Salt 10a Following the general procedure for photo-oxygenation, compound 9a (110 mg, 0.28 mmol) yielded compound 10a as slightly brown solid (110 mg, 92%).

$^1$H NMR (300 MHz, $D_2O$)R-isomer=6.73 (d, J=7.9 Hz, 1 H), 6.62 (d, J=7.9 Hz, 1H); 6.38 (d, J=9.0 Hz, 1H); 6.24 (d, J=9.0 Hz, 1H); 4.81 (s, 1 H), 4.70-4.75 (m, 1H); 3.70-3.97 (m, 2H); 3.55 (s, 3H); 3.51 (s, 3H); 3.15-3.62 (m, 5 H), 2.60-2.78 (m, 1 H), 2.26-2.39 (m, 1 H), 1.00-1.24 (m, 1H), 0.67-0.90 (m, 2 H), 0.35-0.58 (m, 1 H) ppm.
(b) Endoperoxide Oripavine Br-Salt 10b Following the general procedure for photo-oxygenation, compound 9b (110 mg, 0.26 mmol) yielded compound 10b as slightly brown solid (110 mg, 93%). The obtained $^1$H NMR spectrum is identical to the spectra of compound 10a.

Example 4

General Procedure for the Reduction of Endoperoxide Intermediates

To a solution of the endoperoxide intermediate (0.20-0.30 mmol) dissolved in a mixture of $H_2O$:isopropanol:formic acid (1:1:1) (2.4 mL) was added Pd/C (10%) (10 weight %). The reaction mixture was flushed three times with hydrogen and then stirred at 1 atm of hydrogen for 24 h. The suspension was filtered through a short plug of Celite® and washed with MeOH. The filtrate was concentrated in vacuo and the residue was lyophilized. Flash column chromatography on silica using dichloromethane:MeOH (9:1) as eluent provided the corresponding product.
(a) Methylnaltrexone Chloride Salt 11

Following the general procedure for the reduction of endoperoxide intermediates, compound 10a (90 mg, 0.21 mmol) yielded methylnaltrexone chloride salt 11 as a slightly brown solid (60 mg, 71%).

$R_f$ 0.27 ($CH_2Cl_2$/MeOH 4:1); mp above 210° C.; isomeric ratio (R:S) 10:1; IR (KBr) 3167, 3022, 2930, 1736, 1635, 1619, 1496, 1450, 1306, 1261 $cm^{-1}$; $^1$ H NMR (600 MHz, $D_2O$)R-isomer=6.76 (d, J=8.2 Hz, 1 H); 6.72 (d, J=8.2 Hz, 1

H); 4.97 (s, 1 H), 4.03 (d, J=4.5 Hz, 1 H), 3.96 (dd, J=13.9, 3.9 Hz, 1 H), 3.65 (s, 3 H), 3.55-3.64 (m, 1 H), 3.23-3.30 (m, 1 H), 3.08-3.14 (m, 1H), 2.91-3.02 (m, 2H), 2.71-2.84 (m, 2H), 2.19-2.24 (m, 1 H), 2.03-2.09 (m, 1 H), 1.69-1.80 (m, 2 H), 1.11-1.21 (m, 1 H), 0.78-0.87 (m, 1 H), 0.69-0.76 (m, 1 H), 0.51-0.59 (m, 1 H), 0.32-0.39 (m, 1 H) ppm; $^{13}$C NMR (150 MHz, D$_2$O)R-isomer=212.1, 143.5, 139.3, 127.6, 121.3, 118.9, 89.4, 72.7, 72.5, 71.6, 57.3, 53.4, 49.2, 34.7, 32.5, 32.4, 27.7, 24.3, 5.9, 3.5, 2.4 ppm; MS (FAB$^+$) 747 [(C$_{21}$H$_{26}$NO$_4$)$_2$Cl ]$^+$; HRMS (FAB$^+$) calcd for (C$_{21}$H$_{26}$NO$_4$)$^+$ 356.1856, found 356.1872.

(b) Methylnaltrexone Bromide Salt 8

Compound 11 (50 mg, 0.13 mmol) dissolved in minimum amount of H$_2$O:MeOH, 3:1 was filtered through a column packed with Dowex®-1 resin (Sigma, strongly basic bromine loaded, 50-100 mesh) and eluted with dist. H$_2$O (400 mL). The majority of the solvent was removed under reduced pressure and the residue was lyophilized to give the title compound 8 as a white solid (54 mg, 98%). $^1$H and $^{13}$C NMR spectra were identical to spectra of compound 11. MS (FAB$^+$) 793 [(C$_{21}$H$_{26}$NO$_4$)$_2$Br]$^+$.

(c) Methylnaltrexone Bromide Salt 8 (from 10b)

Following the general procedure for the reduction of endoperoxide intermediates, compound 10b (100 mg, 0.22 mmol) yielded methylnaltrexone bromide salt 8 as a colorless solid (79 mg, 74%). $^1$H and $^{13}$C NMR spectra were identical to spectra of compound 11. MS (FAB$^+$) 793 [(C$_{21}$H$_{26}$NO$_4$)$_2$Br]$^+$.

Examples 5-9 refer to the compounds shown in Scheme 10.

Example 5

3-O-acetyl oripavine 12

To oripavine 4 (500 mg, 1.68 mmol) dissolved in dichloromethane (DCM) (10 mL) were added acetic anhydride (0.32 mL, 3.37 mmol) and triethylamine (0.94 mL, 6.73 mmol) at 0° C. The mixture was warmed to room temperature (rt) and stirred for 18 hours. Then the reaction mixture was diluted with DCM (10 mL) and extracted three times with aq. sat. Na$_2$CO$_3$. The organic layer was dried over anhydrous Na$_2$SO$_4$, filtered and the solvent was removed under reduced pressure. The crude residue was purified by flash column chromatography on silica (DCM:MeOH:NH$_4$OH, 100:0:0 to 100:3:1) to provide the title compound as a colorless solid (501 mg, 88%). R$_f$ 0.60 (DCM:MeOH:NH$_4$OH, 92:8:1); mp 171-173° C. (EtOH); $^1$H NMR (600 MHz, CDCl$_3$)=6.79 (d, J=6.8 Hz, 1H), 6.65 (d, J=6.8 Hz, 1H), 5.59 (d, J=6.5 Hz, 1H), 5.33 (s, 3 H), 5.07 (d, J=6.5 Hz, 1H), 3.66 (d, J=6.8 Hz, 1H), 3.63 (s, 3H), 3.35 (d, J=18.2 Hz, 1H), 2.83 (td, J=12.8, 4.9 Hz, 1H), 2.48 (s, 3H), 2.31 (s, 3H), 2.18-2.26 (m, 1H), 1.79 (dd, J=12.6, 2.2 Hz, 1H) ppm; $^{13}$C NMR (150 MHz, CDCl$_3$)= 168.9, 152.3, 147.6, 134.3, 133.1, 132.2, 131.9, 121.9, 119.3, 111.9, 96.3, 89.8, 60.6, 55.1, 45.9, 45.8, 45.5, 42.3, 36.7, 29.9, 21.0 ppm;

HRMS (EI) calcd for (C$_{20}$H$_{21}$NO$_4$) 339.1471, found 339.1475.

Example 6

N-cyclopropylmethylene-northebaine methylbromide 13

A solution of thebaine (3) (600 mg, 1.93 mmol) in chloroform (12 mL) and (bromomethyl)cyclopropane (1.82 mL, 19.28 mmol) was heated at reflux for 18 hrs. The solvent was evaporated and the residue was dried under reduced pressure to give the title compound as colourless solid (858 mg, quant.).

R$_f$ 0.51 (CH$_2$Cl$_2$/MeOH 4:1); isomeric ratio by HPLC(R:S) 2:5; $^1$H NMR (300 MHz, D$_2$O)S-isomer=6.90 (d, J=8.3 Hz, 1H), 6.81 (d, J=8.3 Hz, 1 H), 6.01 (d, J=6.8 Hz, 1 H), 5.55 (s, 1 H); 5.28 (d, J=6.6 Hz, 1 H), 4.67 (d, J=7.2 Hz, 1 H), 3.85-3.94 (m, 1 H); 3.84 (s, 3H), 3.63 (s, 3H), 3.38-3.58 (m, 4H), 3.13-3.37 (m, 4 H), 2.41-2.62 (m, 1H), 1.88-2.02 (m, 1H), 1.10-1.32 (m, 1H), 0.78-0.91 (m, 2H), 0.42-0.56 (m, 2H) ppm; $^{13}$C NMR (150 MHz, CDCl$_3$) S-isomer=154.7, 144.5, 143.8, 131.0, 122.7, 121.7, 121.2, 120.2, 114.3, 95.4, 87.6, 69.8, 63.5, 56.5, 53.4, 43.5, 40.1, 32.1, 31.0, 14.4, 5.4, 4.6, 4.5 ppm; $^1$H NMR (300 MHz, CDCl$_3$) R-isomer=6.74 (d, J=8.2 Hz, 1 H), 6.72 (d, J=8.2 Hz, 1 H), 6.24 (d, J=6.5 Hz, 1 H), 5.41 (s, 1 H); 5.10 (d, J=6.8 Hz, 1 H), 4.67 (d, J=7.2 Hz, 1 H), 3.90-4.05 (m, 2 H); 3.86 (s, 3H), 3.70-3.84 (m, 3H), 3.65 (s, 3H), 3.57 (s, 3H), 3.33-3.43 (m, 1H), 3.22-3.20 (m, 1H), 2.47-2.56 (m, 1 H), 1.30-1.40 (m, 1H), 0.86-0.94 (m, 2H), 0.65-0.79 (m, 2H) ppm; $^{13}$C NMR (150 MHz, CDCl$_3$) R-isomer=154.8, 144.5, 143.7, 131.0, 122.4, 121.5, 121.4, 120.3, 114.3, 95.4, 87.6, 69.2, 68.0, 56.5, 55.6, 54.6, 46.5, 44.0, 32.2, 30.8, 5.9, 4.8, 4.5 ppm; LC/MS (ESI$^+$) 366.3 (C$_{23}$H$_{28}$NO$_3$)$^+$.

Example 7

N-cyclopropylmethylene-3-O-acetyl oripavine methylbromide 14

A solution of 3-O-acetyl oripavine (12) (300 mg, 1.32 mmol) in chloroform (6 mL) and (bromomethyl)cyclopropane (1.24 mL, 13.16 mmol) was heated at reflux for 18 hrs. The solvent was evaporated and the residue was dried under reduced pressure to give the title compound as colourless solid (392 mg, quant.). R$_f$ 0.55 (CH$_2$Cl$_2$/MeOH 4:1); mp 213-215° C. (CHCl$_3$/Et$_2$O); isomeric ratio by HPLC(R:S) 1:2; $^1$H NMR (600 MHz, CDCl$_3$) S-isomer=6.89 (d, J=8.2 Hz, 1H), 6.78 (d, J=8.2 Hz, 1H), 6.16 (d, J=6.7 Hz, 1H), 5.50 (d, J=6.7 Hz, 1H) 5.42 (s, 1H), 5.15 (d, J=6.7 Hz, 1H), 3.94-4.02 (m, 1H), 3.81-3.93 (m, 3H), 3.67 (s, 3H), 3.66 (s, 3H), 3.31-3.45 (m, 2H), 2.37 (td, J=13.9, 4.7 Hz, 1H), 2.32 (s, 3H), 2.02-2.11 (m, 1H), 1.09-1.19 (m, 1H), 0.82-0.98 (m, 2H), 0.62-0.76 (m, 2H) ppm; $^{13}$C NMR (150 MHz, CDCl$_3$) S-isomer=168.5, 154.3, 147.6, 133.1, 132.1, 128.8, 123.7, 121.6, 121.4, 120.2, 95.7, 88.3, 69.5, 63.6, 55.6, 53.2, 49.0, 43.4, 32.0, 31.3, 20.8, 5.4, 4.5, 1.9 ppm; $^1$H NMR (600 MHz, CDCl$_3$) R-isomer=6.86 (d, J=8.2 Hz, 1H), 6.75 (d, J=8.2 Hz, 1H), 6.21 (d, J=6.7 Hz, 1H), 5.42 (s, 1H), 5.23 (d, J=6.9 Hz, 1H), 5.11 (d, J=6.7 Hz, 1H), 3.98-4.05 (m, 2H), 3.78-3.89 (m, 2H), 3.66 (s, 3H), 3.57 (s, 3H), 3.35 (td, J=13.3, 3.9 Hz, 1H), 3.25 (dd, J=19.7, 7.0 Hz, 1H), 2.49 (td, J=13.9, 4.9 Hz, 1H), 2.30 (s, 3H), 2.00-2.12 (m, 1H), 1.24-1.32 (m, 1H), 0.89-0.96 (m, 1H), 0.82-0.88 (m, 1H), 0.65-0.76 (m, 2H) ppm; $^{13}$C NMR (150 MHz, CDCl$_3$) R-isomer=168.5, 154.3, 147.6, 133.0, 132.2, 128.6, 123.6, 121.6, 121.5, 120.1, 95.7, 88.3, 68.8, 67.9, 55.6, 54.1, 46.1, 43.8, 32.0, 31.1, 20.8, 5.7, 4.6, 4.5 ppm; MS (FAB$^+$) 867 [(C$_{24}$H$_{28}$NO$_4$)$_2$Br]$^+$.

Example 8

O-methyl methylnaltrexone bromide salt 15

Following the general procedure for photo-oxygenation described in Example 3, compound 13 (500 mg, 1.12 mmol) yielded the endoperoxide intermediate as slightly brown solid (509 mg, 95%). $^1$H NMR (600 MHz, CDCl$_3$) mixture of S- and R-isomer=6.66-6.77 (m, 6H), 6.42 (d, J=9.1 Hz, 1H), 6.33 (d, J=9.1 Hz, 2H), 6.26 (d, J=9.1 Hz, 2H), 6.23 (d, J=9.1 Hz, 1H), 5.18 (d, J=6.1 Hz, 2H), 4.98 (d, J=6.0 Hz, 1H), 4.65 (s, 1H), 4.63 (s, 2H), 4.49 (dd, J=13.0, 5.9, 2H), 4.17-4.23 (m, 1H), 4.06-4.14 (m, 2H), 4.01 (d, J=20.8 Hz, 2H), 3.94 (d, J=20.4 Hz, 1H), 3.78-3.82 (m, 10H), 3.72-3.76 (m, 9H), 3.37-3.63 (m, 16H), 2.66-2.74 (m, 1H), 2.56-2.64 (m, 2H), 2.46 (bs, 8H), 2.21 (t, J=16.8 Hz, 3H), 1.34-1.41 (m, 1H), 1.16-1.26 (m, 2H), 0.75-0.95 (m, 7H), 0.56-0.66 (m, 5H); MS (FAB$^+$) 398 $C_{23}H_{28}NO_5^+$.

The endoperoxide intermediate was used in the next step without further purification. Following the general procedure for the reduction of endoperoxide intermediates described in Example 4, thebaine endoperoxide bromide salt (97 mg, 0.20 mmol) yielded 3-O-methyl methylnaltrexone bromide salt 15 as a colorless solid (82 mg, 90%). R$_f$ 0.47 (DCM:MeOH, 4:1); mp above 210° C.; IR (KBr) 3434, 3006, 2933, 2911, 2840, 1736, 1636, 1611, 1505, 1441, 1384, 1364, 1273 cm$^{-1}$; $^1$H NMR (600 MHz, MeOH-d$_4$) R-isomer=6.88-6.90 (m, 2H), 4.92 (s, 1H), 4.12 (d, J=3.6 Hz, 1H), 4.09 (d, J=3.6 Hz, 1H), 3.91 (s, 3H), 3.81 (s, 3H), 3.70 (d, J=20.4 Hz, 1H), 3.43 (d, J=3.4 Hz, 1H), 3.33 (s, 1H), 3.25 (d, J=3.4 Hz, 1H), 2.91-3.11 (m, 4H), 2.20 (d, J=3.4 Hz, 1H), 2.17 (d, J=3.4 Hz, 1H), 1.69-1.82 (m, 2H), 1.28-1.35 (m, 1H), 0.91-0.99 (m, 1H), 0.89-0.90 (m, 1H), 0.67-0.76 (m, 1H), 0.49-0.52 (m, 1H) ppm; $^1$H NMR (600 MHz, D$_2$O)S-isomer=6.89 (d, J=8.4 Hz, 1H), 6.81 (d, J=8.4 Hz, 1H), 4.96 (s, 1H), 4.90 (dd, J=4.2, 4.1 Hz, 1H), 4.19 (d, J=4.1 Hz, 1H), 3.78 (s, 3H), 3.60 (d, J=14.6 Hz, 1H), 3.55 (s, 1H), 3.37 (d, J=13.7 Hz, 1H), 3.15 (s, 2H), 3.02-3.15 (m, 3H), 2.80-2.93 (m, 2H), 2.69-2.77 (m, 1H), 2.18 (d, J=14.6 Hz, 1H), 2.05 (d, J=14.6 Hz, 1H), 1.57-1.76 (m, 2H), 1.09-1.17 (m, 1H), 0.75-0.82 (m, 1H), 0.65-0.71 (m, 1H), 0.43-0.51 (m, 1H), 0.26-0.37 (m, 1H) ppm; $^{13}$C NMR (150 MHz, MeOH-d$_4$) R-isomer=207.4, 145.1, 143.9, 127.9, 121.4, 120.6, 116.5, 89.3, 72.2, 72.1, 57.3, 56.2, 53.0, 48.9, 48.0, 47.9, 34.6, 32.5, 27.6, 24.5, 5.85, 4.75, 3.45 ppm; HRMS (FAB$^+$) calcd for $(C_{22}H_{28}NO_4)^+$370.2000, found 370.2024.

Example 9

3-O-acetyl methylnaltrexone bromide salt 16

Following the general procedure for photo-oxygenation described in Example 3, compound 14 (200 mg, 0.42 mmol) yielded endoperoxide intermediate as slightly brown solid (181 mg, 85%). $^1$H NMR (600 MHz, CDCl$_3$) mixture of S- and R-isomers=6.85-6.91 (m, 2H), 6.78-6.83 (m, 2H), 6.36-6.42 (m, 1H), 6.27-6.34 (m, 3H), 5.29 (d, J=6.0 Hz, 1H), 5.01 (d, J=6.0 Hz, 1H), 4.70 (s, 1H), 4.68 (s, 1H), 4.47-4.54 (m, 1H), 4.39-4.47 (m, 1H), 4.14-4.25 (m, 1H), 4.07-4.14 (m, 1H), 4.00-4.06 (m, 1H), 3.94-4.00 (m, 1H), 3.88-3.93 (m, 1H), 3.86 (s, 3H), 3.81 (s, 3H), 3.43-3.61 (m, 10H), 2.68-2.77 (m, 1H), 2.59-2.68 (m, 1H), 2.24-2.34 (m, 8H), 1.71-1.81 (m, 2H), 1.30-1.38 (m, 1H), 1.18-1.28 (m, 2H), 0.80-0.98 (m, 4H), 0.62-0.74 (m, 3H) ppm; MS (FAB$^+$) 426 [(C$_{24}$H$_{28}$NO$_6$)$_2$Br]$^+$.

The endoperoxide intermediate was used in the next step without further purification. Following the general procedure for the reduction of endoperoxide intermediates described in Example 4,3-O-acetyl oripavine endoperoxide bromide salt (100 mg, 0.20 mmol) yielded 3-O-acetyl methylnaltrexone bromide salt 16 as a colorless solid (61 mg, 65%). mp above 210° C. (CHCl$_3$/Et$_2$O); isomeric ratio by HPLC(R:S) 1:2; IR (KBr) 3411, 2972, 2917, 2849, 1759, 1724, 1626, 1492, 1447, 1370, 1341, 1218, 1193, 1154, 1077 cm$^{-1}$; $^1$H NMR (300 MHz, D$_2$O)S-isomer=6.98 (d, J=8.3 Hz, 1H), 6.90 (d, J=8.3 Hz, 1H), 5.04 (s, 1H), 4.96 (dd, J=10.9, 2.3 Hz, 1H), 4.26 (d, J=4.3 Hz, 1H), 3.60-3.76 (m, 2H), 3.37-3.50 (m, 1H), 2.74-3.26 (m, 8H), 2.29 (s, 3H), 2.17-2.28 (m, 1H), 2.05-2.16 (m, 1H), 1.70-1.84 (m, 2H), 1.09-1.27 (m, 1H), 0.67-0.90 (m, 2H), 0.46-0.60 (m, 1H), 0.30-0.43 (m, 1H) ppm; $^1$H NMR (600 MHz, D$_2$O)R-isomer=6.94 (d, J=8.3 Hz, 1H), 6.86 (d, J=8.3 Hz, 1H), 5.02 (s, 1H), 3.93 (dd, J=12.1, 3.8 Hz, 1H), 3.67 (d, J=20.4 Hz, 1H), 3.63 (s, 3H), 3.26-3.32 (m, 1H), 3.18 (dd, J=13.9, 2.9 Hz, 1H), 2.91-2.99 (m, 2H), 2.83 (td, J=13.9, 2.9 Hz, 1H), 2.72-2.78 (m, 1H), 2.26 (s, 3H), 2.18-2.23 (m, 1H), 2.00-2.06 (m, 1H), 1.71-1.79 (m, 2H), 1.08-1.14 (m, 1H), 0.78-0.86 (m, 1H), 0.66-0.74 (m, 1H), 0.48-0.55 (m, 1H), 0.27-0.36 (m, 1H) ppm; $^{13}$C NMR (150 MHz, D$_2$O)R-isomer=211.0, 172.2, 147.3, 132.6, 128.2, 124.2, 121.5, 90.0, 72.7, 72.3, 71.2, 57.0, 53.4, 48.9, 34.6, 32.2, 30.2, 27.9, 24.1, 20.0, 5.8, 3.4, 2.3 ppm; MS (FAB$^+$) 875 [(C$_{23}$H$_{28}$NO$_5$)$_2$Br]$^+$, HRMS (FAB$^+$) calcd for $(C_{23}H_{28}NO_5)^+$398.1967, found 398.1977.

Example 10

Partial Reduction of Endoperoxide Intermediate 10a

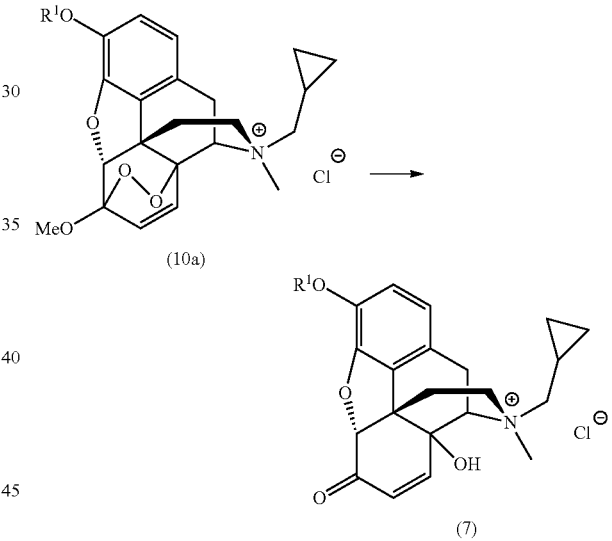

Scheme 11

To a solution of the endoperoxide intermediate 10a (1.02 g) dissolved in a mixture of H$_2$O:isopropanol:formic acid (1:1:1) (5 mL) was added thiourea (0.04 g) and Pd/C (0.05 g, 10 wt %). The reaction mixture was flushed three times with hydrogen and then stirred at 1 atm of hydrogen for 18 h. The suspension was filtered through a short plug of Celite® and washed with MeOH. The filtrate was concentrated in vacuo. Flash column chromatography (silicagel, eluent DCM+20% MeOH) provided the corresponding product 7; m.p. 213-215° C. (EtOH); [α]$^{20}_D$=−26.21 (c=0.5, MeOH); IR (KBr) v 3622, 3404, 3312, 2954, 1679, 1620, 1503, 1294, 1123, 1076, 944, 880 cm$^{-1}$; $^1$H NMR (600 MHz, MeOD) δ 7.07 (d, J=10.1 Hz, 1H), 6.74 (d, J=8.3 Hz, 1H), 6.72 (d, J=8.3 Hz, 1H), 6.11 (d, J=10.1 Hz, 1H), 4.85 (s, 1H), 4.22 (d, J=4.1 Hz, 1H) 3.99 (dd, J=13.7, 3.9 Hz, 1H), 3.75 (s, 3H), 3.70 (d, J=20.0 Hz, 1H), 3.48 (dd, J=13.3, 3.8 Hz, 1H), 3.16 (ddd, J=13.3, 13.3, 3.6 Hz, 1H), 3.06 (dd, J=20.0, 4.2 Hz, 1H), 2.99 (ddd, J=14.4, 14.4, 4.3 Hz, 1H), 2.93 (dd, J=13.7, 9.7 Hz, 1H), 1.98 (dd, J=14.6, 2.6 Hz, 1H), 1.30 (m, 1H), 0.98 (m, 1H), 0.88 (m, 1H), 0.69 (m, 1H), 0.49

(m, 1H); $^{13}$C (150 MHz, MeOD) δ 194.11, 146.47, 143.20, 140.91, 131.66, 129.19, 120.44, 119.61, 118.72, 85.72, 72.11, 70.57, 69.69, 57.78, 52.68, 46.71, 27.46, 23.67, 5.83, 3.63, 2.30; MS (FAB$^+$) m/z (%): 55 (36), 98 (14), 136 (6), 298 (5), 354 (100); HRMS calcd for $C_{21}H_{24}NO_4^+$ 354.1700, found 354.17363.

Example 11

Cyclopropylmethylene-oripavine (CPM-Oripavine) Ammonium Bromide Salt (Alternative Route)

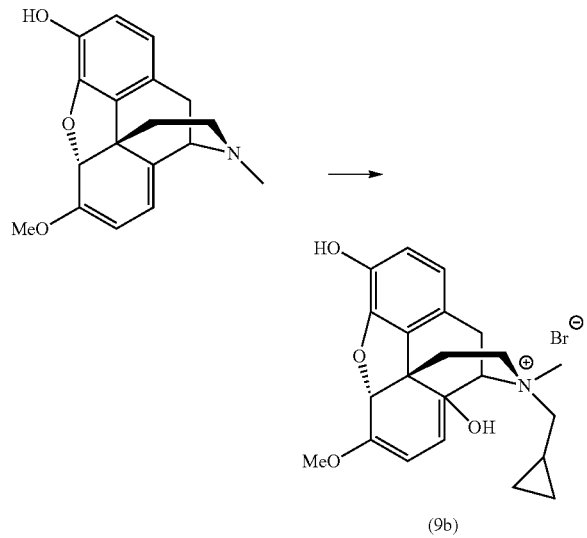

Scheme 12

(9b)

To a flame dried, argon purged round bottom flask with attached reflux condenser was charged a suspension of oripavine (1.84 g, 6.18 mmol) in anhydrous DMF (10 mL). (Bromomethyl)cyclopropane (1.8 mL, 18.5 mmol, 3.0 eq) was added to the vigorously stirred suspension of oripavine in one portion and at room temperature. The reaction mixture was immersed in a pre-heated oil-bath at 80° C. and allowed to stir under argon atmosphere for 12 hours. The reaction mixture was cooled and an aliquot was analyzed by HPLC (285 nm) and determined to contain approximately 3.6% (AUC) oripavine (as the HBr salt). Sodium bicarbonate (21 mg, 0.24 mmol, 4 mol %) was added to the reaction mixture and allowed to stir for 1 hour prior to the addition of (bromomethyl)cyclopropane (0.30 mL, 3.1 mmol, 0.5 eq) at room temperature. The reaction mixture was immersed in the pre-heated oil-bath at 80° C. for an additional 8 hours prior to analysis by HPLC (285 nm). It was observed that approximately 1% oripavine remained in the reaction mixture. The reaction mixture (fine beige slurry) was cooled to room temperature and filtered through a fine fritted funnel. The filtered solid was washed with MeOH (1.5 mL) and the product precipitated by slow, inverse addition of the reaction mixture to a vigorously stirred volume of toluene (~100 mL). The precipitate was filtered and washed with toluene (2×10 mL), solid collected, and dried under vacuum to provide a slightly off-white solid in greater than quantitative yield. This crude material was triturated in acetone (50 mL) at room temperature for 2 hours prior to a second filtration. The solid was collected and dried under vacuum to yield 2.60 g (94% yield) of N-cyclopropylmethylene oripavine ammonium bromide salt (9b) as a white, free-flowing solid; mp=194-200° C.; isomeric ratio determined by HPLC (S:R) 2.6:1; R-isomer: m.p. 219-221° C. (EtOH); R$_f$ 0.30 (DCM+20% methanol); $[α]^{20}_D$=−109.38 (c=1, MeOH); $^1$H NMR (600 MHz, DMSO) δ 9.37 (s, 1H), 6.62 (d, J=8.1 Hz, 1H), 6.55 (d, J=8.1 Hz, 1H), 6.01 (d, J=6.6 Hz, 1H), 5.42 (s, 1H), 5.29 (d, J=6.6 Hz, 1H), 4.67 (d, J=7.2, 1H) 3.71 (m, 1H), 3.70 (m, 1H), 3.61 (s, 3H), 3.45 (dd, J=13.5, 4.6 Hz, 1H), 3.39 (dd, J=13.7, 7.6 Hz, 1H), 3.29 (ddd, J=13.2, 13.2, 4.0, 1H) 3.19 (s, 3H), 3.06 (dd, J=19.4, 7.2 Hz, 1H), 2.59 (ddd, J=14.1, 14.1, 5.1, 1H), 1.86 (dd, J=14.2, 2.9 Hz, 1H), 1.21 (m, 1H), 0.75 (m, 2H), 0.51 (m, 1H), 0.44 (m, 1H); $^{13}$C (150 MHz, DMSO) δ 154.63, 143.48, 140.36, 132.58, 124.10, 122.50, 120.19, 119.81, 117.64, 96.05, 87.21, 68.08, 67.08, 55.58, 54.04, 46.08, 44.16, 31.48, 30.39, 5.05, 4.44, 4.15.

S-isomer: m.p. 195-197° C. (MeOH+i-PrOH); R$_f$ 0.28 (DCM+20% methanol); $[α]^{20}_D$=−43.73 (c=1, MeOH); $^1$H NMR (600 MHz, DMSO) δ 9.37 (s, 1H), 6.63 (d, J=8.0 Hz, 1H), 6.57 (d, J=8.0 Hz, 1H), 5.98 (d, J=6.6 Hz, 1H), 5.39 (s, 1H), 5.26 (d, J=6.6 Hz, 1H), 4.75 (d, J=6.9, 1H), 3.77 (d, J=19.6 Hz, 1H), 3.64 (dd, J=13.4, 6.1 Hz, 1H), 3.60 (s, 3H), 3.49 (dd, J=13.4, 3.2 Hz, 1H), 3.35 (m, 1H), 3.29 (s, 3H), 3.28 (m, 1H), 3.06 (dd, J=19.5, 7.0 Hz, 1H), 2.56 (ddd, J=14.0, 14.0, 4.5, 1H), 1.79 (d, J=11.9, 1H), 1.21 (m, 1H), 0.72 (m, 2H), 0.52 (m, 1H), 0.39 (m, 1H); $^{13}$C (150 MHz, DMSO) δ 154.63, 143.36, 140.36, 132.58, 124.11, 122.61, 120.20, 119.74, 117.62, 96.04, 87.25, 68.56, 63.92, 55.58, 53.99, 48.60, 43.65, 31.33, 30.64, 4.93, 4.55, 4.33; MS (FAB+) m/z (%): 55 (31), 98 (24), 112 (38), 239 (12), 352 (100); HRMS calcd for $C_{22}H_{26}NO_3^+$ 352.1907, found 352.18978.

The use of dimethylacetamide (DMAc) as solvent in the above quaternization provided a reaction mixture as a thick slurry and proceeded to product as a heterogeneous mixture. Isolation consisted of filtration and provided 94% of mass in 98.3% purity by HPLC (S/R ratio=1.5:1).

The use of N-methylpyrrolidone (NMP) and DMF as the solvent mixture (1:1) did not provide selectivity in terms of precipitation (wet cake) of the R-isomer of CPM-oripavine salt. Several operations were performed on the mother liquor (precipitation followed by trituration of resultant solid) and provided CPM-oripavine salt in 56% yield from mother liquor with a purity of 96.7% by HPLC (S/R ratio=7.1:1).

Example 12

Dealkylation of CPM-Oripavine (Preparation of CPM-Nororipavine) (17)

Scheme 13

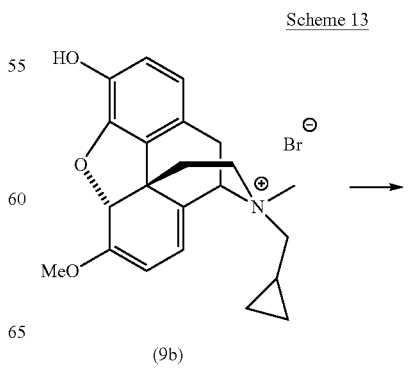

(9b)

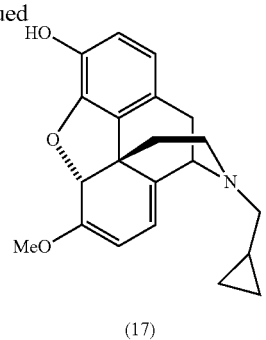

(17)

To a slurry of sodium ethoxide (0.94 g, 13.88 mmol) in freshly distilled DMSO (9 mL) was added dodecanethiol (2.80 g, 13.88 mmol, distilled) in one portion. The resulting mixture was vigorously stirred and immersed in a preheated oil bath at 90° C. for 10 minutes prior to decreasing the temperature to 80° C. A solution of N-cyclopropylmethylene oripavine ammonium bromide (9b) (Example 15, 2.0 g, 4.63 mmol) in DMSO (9 mL) at room temperature was added to the preformed mixture of dodecanethiolate at 80° C. over 10 minutes. A sharp colour change from a clear, slightly yellow solution to a black colored mixture occurred after the first several drops of the N-cyclopropylmethylene oripavine ammonium bromide solution. The reaction mixture was allowed to stir at 80° C. for 45 minutes following the addition and monitored by HPLC (285 nm). After the complete consumption of starting material the reaction mixture was allowed to cool to room temperature with stirring and poured into $H_2O$ (80 mL). The pH of the aqueous mixture was adjusted to pH=2 with HCl (6 M) and washed with hexanes (1×20 mL, 1×10 mL). The pH of the aqueous mixture (milky yellow suspension) was readjusted to pH=8 with NaOH (aq, 15%). A fine, white precipitate was observed upon pH adjustment and was cleared by extraction with EtOAc (1×20 mL, 1×15 mL). The pH of the aqueous phase was adjusted again to pH=8 (white precipitate observed) and extracted with EtOAc (3×10 mL). The organic layers were combined and washed with $H_2O$ (1×10 mL) and brine (1×10 mL). The organic layers were dried over $MgSO_4$, filtered, and concentrated to provide 1.75 g of crude material as a black residue. The material was chromatographed on silica gel (20% MeOH/EtOAc) and crystallized from acetone to afford 0.82 g (53% yield) of cyclopropylmethylene nororipavine (17) as a pale-yellow, crystalline solid; $R_f$ 0.25 (20% MeOH/EtOAc); m.p. 165-166° C. (DCM). m.p. 166-167° C. (methanol); $[\alpha]^{20}_D = -168.60$ (c=1, $CHCl_3$); IR (KBr) v 3445, 2908, 1630, 1458, 1234, 1046, 1016, 926, 868 cm$^{-1}$; $^1H$ NMR (600 MHz, $CDCl_3$) δ 6.65 (d, J=8.4 Hz, 1 H), 6.55 (d, J=8.4 Hz, 1 H), 5.59 (d, J=6.6 Hz, 1 H), 5.29 (s, 1 H), 5.07 (d, J=6.6 Hz, 1 H), 4.02 (d, J=6.6 Hz, 1 H), 3.61 (s, 3 H), 3.29 (d, J=18.0 Hz, 1 H), 3.00 (dd, J=12.6, 4.2 Hz, 1 H), 2.90 (m, 1 H), 2.76 (dd, J=18.0, 7.2 Hz, 1 H), 2.55 (m, 2 H), 2.24 (m, 1 H), 1.71 (d, J=11.4, 1 H), 0.97 (m, 1 H), 0.56 (d, J=8.4 Hz, 2 H), 0.19 (d, J=8.4 Hz, 2H); $^{13}C$ (150 MHz, $CDCl_3$) δ 152.21, 143.10, 138.83, 133.16, 132.55, 126.69, 119.74, 116.45, 112.05, 96.36, 89.39, 58.57, 58.55, 54.99, 46.84, 43.83, 36.21, 31.18, 9.17, 3.92 (2×$CH_2$); MS (+EI) m/z (%): 43 (100), 58(19), 84 (56), 227 (8), 282 (12), 337 (41); HRMS calcd for $C_{21}H_{23}NO_3$ 337.1678, found 337.16814.

The demethylation of the quaternary ammonium salt of oripavine was revisited and utilized tert-dodecanethiol (as thiolate) as the nucleophilic reagent and sodium tert-butoxide as the base. Table 2 summarizes these studies and conditions. In addition to the noticeable increase in yield on small scale experiments, the appearance and handling of the reaction mixture during workup has significantly improved. It is also noteworthy to mention that the R-isomer reacts at a faster rate than the S-isomer of CPM-oripavine salt.

Example 13

Synthesis of Naltrexone

Scheme 14

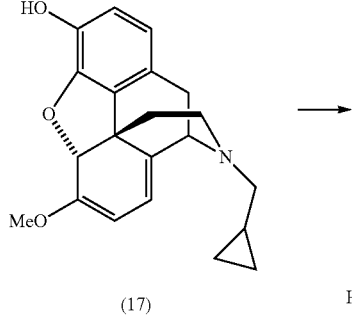

(17)

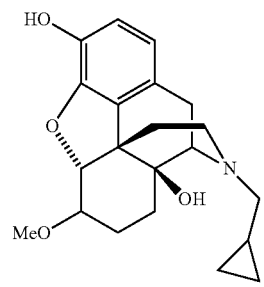

Naltrexone

A solution of N-methylcyclopropyl nororipavine (17) (Example 12, 515 mg, 1.52 mmol) in $H_2O$/HOAc (1:1 v/v) was chilled to 5° C. with stirring. A solution of peracetic acid (32 wt %) was added dropwise over 2 minutes. The mixture was allowed to stir at 5° C. for 10 minutes prior to warming to room temperature. The reaction was monitored by TLC (10% MeOH/EtOAc) and consumption of starting material was observed after 35 minutes post addition of peracetic acid. The reaction mixture at room temperature was diluted with isopropanol (2.5 mL), palladium on charcoal (51 mg, 10 wt %) was added, and the reaction mixture subjected to a hydrogen atmosphere (Parr shaker, 50 PSI) for 15 hours. The mixture was filtered through a pad of celite and washed with isopropanol. Acetic acid was removed as an azeotrope with toluene prior to concentration to dryness. 509 mg (95% yield) of naltrexone was obtained after further drying under vacuum; $R_f$=0.55 (92:8 $CHCl_3$/MeOH); mp=167-169° C. ($CHCl_3$); $[\alpha]^{20}_D$=-84.84 ($CHCl_3$); $^1H$ NMR ($CDCl_3$, 300 MHz) δ 6.73 (d, J=7.6, 1H), 6.59 (d, J=7.6, 1H), 5.66 (s, 2H), 4.76 (s, 1H), 3.22 (d, J=5.6, 1H), 3.12-3.03 (m, 2H), 2.73 (dd, J=4.1, 11.6, 1H), 2.58 (dd, J=5.8, 18.6, 1H), 2.52-2.30 (m, 4H), 2.16 (td, J=5.9, 3.0, 1H), 1.92 (d, J=12.0, 1H), 1.75-1.50 (m, 3H), 0.87 (m, 2H), 0.56 (d, J=7.4, 2H), 0.16 (d, J=4.4, 2H).

The following Example refers to the compounds shown in Scheme 15.

Example 14

Synthesis of Nalbuphone and Nalbuphine

As shown in Scheme 11 below, nalbuphone was prepared from oripavine using an analogous sequence of reactions as that described in Examples 11-13 for the preparation of naltrexone.

To a flame-dried, argon-purged round bottom flask with attached reflux condenser was charged a suspension of oripavine (2.0 g, 6.73 mmol) in anhydrous DMF (10 mL). (Bromomethyl)cyclobutane (3.01 g, 20.2 mmol, 3.0 eq) was added to the vigorously stirred suspension of oripavine as one portion and at room temperature. The reaction mixture was immersed in a pre-heated oil-bath at 85° C. and allowed to stir under argon atmosphere for 18 hours. The reaction mixture was removed from heat and an aliquot was analyzed by HPLC (285 nm) and determined to contain approximately 9.5% (AUC) oripavine (as the HBr salt). Potassium carbonate (88 mg, 0.68 mmol, 9.5 mol %) was added to the reaction mixture and allowed to stir for 1 hour prior to the addition of (bromomethyl)cyclobutane (0.5 g, 3.4 mmol, 0.5 eq) at room temperature. The reaction mixture was immersed in the preheated oil-bath at 85° C. for an additional 5 hours prior to analysis by HPLC (285 nm). It was observed that approximately 3% oripavine remained in the reaction mixture. The reaction mixture (fine beige slurry) was cooled to room temperature. The reaction mixture was poured to a vigorously stirred toluene (~100 mL). The precipitate was subjected to column chromatography (silicagel, eluent DCM+15% MeOH) which afforded 2.65 g (88%) of white solid (18), isomeric ratio determined by HPLC (S:R) 3.0:1. R-isomer: m.p. 230-233° C. (Methanol); $R_f$ 0.39 (DCM+20% MeOH); $[\alpha]^{20}_D$=−77.34 (c=0.5, MeOH:AcOH/1:1); IR (KBr) v 3004, 2953, 2920, 1590, 1496, 1460, 1300, 1240, 1116, 1012, 928 cm$^{-1}$; $^1$H NMR (600 MHz, DMSO) δ 9.37 (s, 1H), 6.62 (d, J=8.2 Hz, 1H), 6.55 (d, J=8.2 Hz, 1H), 6.00 (d, J=6.6 Hz, 1H), 5.41 (s, 1H), 5.28 (d, J=6.7 Hz, 1H), 4.52 (d, J=7.2, 1H), 3.75 (dd, J=13.7, 6.6 Hz, 1H), 3.69 (d, J=19.5, 1H), 3.60 (s, 3H), 3.55 (dd, J=13.8, 6.6 Hz, 1H), 3.40 (dd, J=13.2, 4.4 Hz, 1H), 3.29 (ddd, J=13.5, 13.5, 3.9, 1H), 3.05 (s, 3H), 3.00 (dd, J=19.6, 7.3 Hz, 1H), 2.93 (m, 1H), 2.54 (ddd, J=13.8, 5.1 Hz, 1H), 2.16 (m, 2H), 1.91 (m, 3H), 1.84 (dd, J=14.3, 3.0 Hz, 1H), 1.78 (m, 1H); $^{13}$C (150 MHz, DMSO) δ 154.62, 143.47, 140.36, 132.27, 123.99, 122.48, 120.19, 119.88, 117.64, 96.03, 87.17, 68.01, 67.50, 55.58, 54.40, 46.01, 44.00, 31.39, 30.34, 29.09, 28.02, 27.94, 19.07; MS (FAB+) m/z (%): 44 (50), 58 (23), 126 (55), 211 (7), 239 (18), 366 (100); HRMS calcd for $C_{23}H_{28}NO_3^+$ 366.2064, found 366.20156. S-isomer: m.p. 185-189° C. (Methanol); $R_f$ 0.32 (DCM+20% MeOH); $[\alpha]^{20}_D$=−35.03 (c=1, MeOH); $^1$H NMR (600 MHz, DMSO) δ 9.37 (s, 1H), 6.62 (d, J=8.0 Hz, 1H), 6.56 (d, J=8.0 Hz, 1H), 5.94 (d, J=6.6 Hz, 1H), 5.39 (s, 1H), 5.27 (d, J=6.6 Hz, 1H), 4.62 (d, J=7.0, 1H), 3.71 (d, J=19.6 Hz, 1H), 3.60 (m, 1H), 3.60 (s, 3H), 3.46 (dd, J=13.2, 7.2 Hz, 1H), 3.42 (m, 1H), 3.31 (ddd, J=13.5, 13.5, 3.6, 1H), 3.12 (s, 3H), 3.02 (m, 1H), 2.91 (m, 1H), 2.56 (ddd, J=14.0, 4.8 Hz, 1H), 2.11 (m, 2H), 1.91 (m, 2H), 1.84 (m, 1H), 1.76 (m, 2H); $^{13}$C (150 MHz, DMSO) δ 154.63, 143.35, 140.35, 132.51, 124.09, 122.56, 120.19, 119.71, 117.61, 96.04, 87.19, 68.71, 64.37, 55.57, 54.40, 48.43, 43.64, 31.34, 30.51, 29.26, 28.40, 27.70, 19.02; MS (FAB+) m/z (%): 44 (50), 58(23), 126 (55), 211 (7), 239 (18), 366 (100); HRMS calcd for $C_{23}H_{28}NO_3^+$ 366.2064, found 366.20692.

To a slurry of sodium ethoxide (0.46 g, 6.82 mmol) in freshly distilled DMSO (4.5 mL) was added dodecanethiol (1.38 g, 6.82 mmol, distilled) in one portion. The resulting mixture was vigorously stirred and immersed in a preheated oil bath at 90° C. for 10 minutes prior to decreasing the temperature to 80° C. A solution of N-cyclobutylmethylene oripavine ammonium bromide in DMSO (4.5 mL) at room temperature was added to the preformed mixture of dodecanethiolate at 80° C. over 10 minutes. A sharp color change from a clear, slightly yellow solution to a black colored mixture occurred after the first several drops of the N-cyclobutyllmethyl oripavine ammonium bromide solution. The reaction mixture was allowed to stir at 80° C. for 50 minutes post addition and monitored by HPLC (285 nm). After consumption of starting material was observed the reaction mixture was allowed to cool to room temperature with stirring and poured into $H_2O$ (40 mL). The pH of the aqueous mixture was adjusted to pH=2 with HCl (6 M) and washed with hexanes (2×15 mL). The pH of the aqueous mixture (milky yellow suspension) was readjusted to pH=8 with NaOH (aq, 15%). A fine, white precipitate was observed upon pH adjustment and was cleared by extraction with EtOAc (1×20 mL, 1×10 mL). The pH of the aqueous phase was adjusted again to pH=8 (white precipitate observed) and extracted with EtOAc (3×10 mL). The organic layers were combined and washed with $H_2O$ (1×10 mL) and brine (1×10 mL). The organic layers were dried over $MgSO_4$, filtered, and concentrated. The material was chromatographed on silica gel (20% MeOH/EtOAc) to afford 0.46 g (58% yield) of cyclobutylmethylene nororipavine (19) as a pale-yellow solid, m.p. 114-116° C. (Toluene); $R_f$ 0.44 (ethyl acetate+20% methanol); $[\alpha]^{20}_D$=−150.06 (c=1.0, $CHCl_3$); IR($CHCl_3$) v 3568, 2962, 2929, 1608, 1507, 1454, 1329, 1263, 1023, 868 cm$^{-1}$; $^1$H NMR (600 MHz, $CDCl_3$) δ 6.65 (d, J=8.0 Hz, 1H), 6.55 (d, J=8.0 Hz, 1H), 5.55 (d, J=6.4 Hz, 1H), 5.29 (s, 1H), 5.08 (d, J=6.4 Hz, 1H), 3.73 (d, J=7.0 Hz, 1H), 3.62 (s, 3H), 3.33 (d, J=18.0 Hz, 1H), 2.89 (t, J=11.7 Hz, 1H), 2.71 (m, 4H), 2.60 (hept, J=7.4, 1H), 2.23 (ddd, J=12.7, 12.7, 4.9 Hz, 1H), 2.10 (m, 2H), 1.91 (m, 1H), 1.81 (m, 1H), 1.74 (pent, J=8.7, 2H), 1.68 (dd, J=12.4, 1.8, 1H); $^{13}$C (150 MHz, $CDCl_3$) δ 152.16, 143.03, 138.69, 133.10, 132.80, 126.82, 119.77, 116.40, 111.89, 96.40, 89.42, 60.17, 59.02, 55.02, 46.75, 44.05, 36.25, 34.52, 31.23, 27.94, 27.86, 18.86; MS (FAB+) m/z (%): 41 (34), 69 (14), 112 (35), 211 (17), 241 (20), 351 (81), 352 (100); HRMS calcd for $C_{22}H_{26}NO_3^+$ 352.1907, found 352.18440.

A solution of N-methylcyclobutylene nororipavine (19) (0.09 g, 0.256 mmol) in 2 ml $H_2O$/HOAc (1:1 v/v) was chilled to 5° C. with stirring. A solution of peracetic acid (0.066 g, 32 wt %) was added dropwise over 1 minutes. The mixture was allowed to stir at 5° C. for 2 hours. The reaction was monitored by TLC (EtOAc+20% MeOH). The reaction mixture at room temperature was diluted with isopropanol (2.0 mL), palladium on charcoal (11 mg, 10 wt %) was added, and the reaction mixture subjected to a hydrogen atmosphere (Parr shaker, 50 Psi) for 15 hours. The mixture was filtered through a pad of celite and washed with isopropanol. Acetic acid was removed as an azeotrope with toluene prior to concentration to dryness. The material was chromatographed on silica gel (EtOAc+20% MeOH) to afford 0.075 g (82% yield) of nalbuphone as a white solid; m.p. 168-169° C. ($C_y$clohexane), m.p. 170-172° C. (Acetone); $R_f$ 0.64 (ethyl acetate+20% methanol); $[\alpha]^{20}_D$=−180.44 (c=1.0, MeOH); IR($CHCl_3$) v 3561, 3454, 2966, 2931, 2830, 1720, 1616, 1457, 1318, 1142, 1057, 944 cm$^{-1}$; $^1$H NMR (600 MHz, $CDCl_3$) δ 6.74 (d, J=8.0 Hz, 1H), 6.61 (d, J=8.0 Hz, 1H), 5.64 (bs, 1H, OH), 4.72 (s, 1H), 3.11 (d, J=18.4 Hz, 1H), 3.04 (ddd, J=14.4, 14.4, 3.6 Hz, 1H), 2.92 (d, J=4.9 Hz, 1H), 2.57 (m, 5H), 2.42 (ddd, J=12.4, 12.4, 4.4 Hz, 1H), 2.33 (d, J=14.4 Hz, 1H), 2.20 (ddd, J=12.0, 12.0, 2.2 Hz, 1H), 2.11 (m, 2H), 1.95 (m, 1H), 1.90 (m, 2H), 1.87 (m, 2H), 1.66 (ddd, J=13.6, 13.6, 2.2 Hz, 1H), 1.56 (d, J=12.6 Hz, 1H); $^{13}$C (150 MHz, $CDCl_3$) δ 209.68, 143.45, 138.69, 129.02, 124.34, 119.87, 117.71, 90.58, 70.31, 62.74, 60.48, 50.93, 43.74, 36.18, 33.73, 31.32, 30.69, 27.00, 26.79, 22.96, 18.76; MS (FAB+) m/z (%): 41 (27), 69 (9), 98 (5), 300 (88), 355 (38), 356 (100); HRMS calcd for $C_{21}H_{26}NO_4^+$ 356.1856, found 356.18552.

The mixture of nalbuphone (0.085 g, 0.239 mmol), Adams catalyst (0.0014 g, 0.006 mmol) in 1.2 mL of solvent system (1-PrOH:water/1:2, pH set up to 12.7) was subjected to hydrogenation in Parr shaker (50 Psi) for 4 h. Then the mixture was diluted with water and pH was set up to 9. Product was extracted with EtOAc (4×5 mL). Combined organic layers were washed with brine and dried over MgSO$_4$. The material was chromatographed on silica gel (EtOAc+20% MeOH) to afford 0.058 g (86% yield) of a white solid which was analyzed by HPLC (285 nm) and determined to contain approximately 94% (AUC) nalbuphine; m.p. >230° C. (EtOH); R$_f$ 0.64 (ethyl acetate+20% methanol); $^1$H NMR (600 MHz, DMSO) δ 8.81 (bs, 1H), 6.55 (d, J=8.0 Hz, 1H), 6.42 (d, J=8.0 Hz, 1H), 4.75 (bs, 1H, OH), 4.43 (d, J=5.6 Hz, 1H), 4.38 (d, J=4.5 Hz, 1H), 4.01 (m, 1H), 2.96 (d, J=18.4 Hz, 1H), 2.72 (d, J=6.5 Hz, 1H), 2.53 (dd, J=18.4, 6.6 Hz, 1H), 2.50 (m, 1H), 2.45 (m, 1H), 2.39 (m, 1H), 2.11 (m, 2H), 2.00 (m, 2H), 1.85 (m, 2H), 1.81 (m, 1H), 1.63 (m, 2H), 1.45 (m, 2H), 1.31 (m, 2H), 0.97 (m, 1H); $^{13}$C (150 MHz, DMSO) δ 146.53, 138.47, 131.43, 124.86, 118.38, 117.56, 90.68, 69.90, 65.81, 62.61, 60.51, 47.04, 43.47, 33.93, 33.63, 29.27, 26.94, 26.65, 23.45, 23.05, 18.77; MS (FAB+) m/z (%): 41 (17), 154 (5), 302 (41), 340 (18), 358 (100); HRMS calcd for C$_{21}$H$_{28}$NO$_4$$^+$ 358.2013, found 358.19737.

SCHEME 15

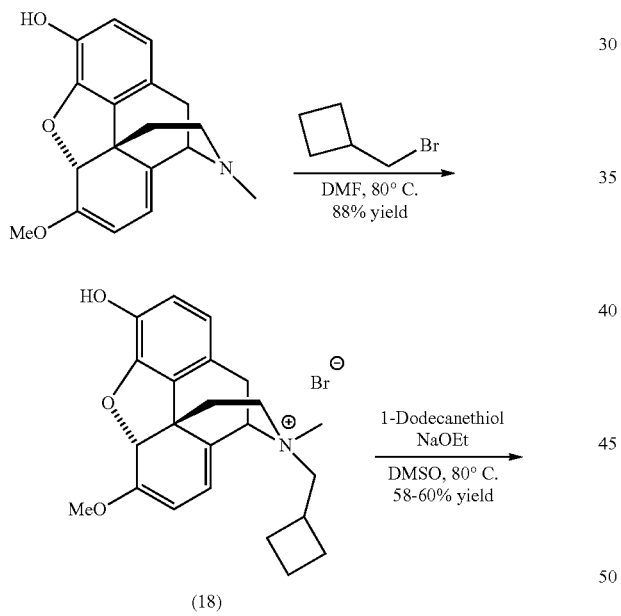

(18)

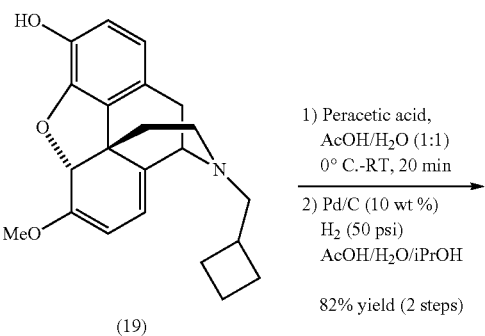

(19)

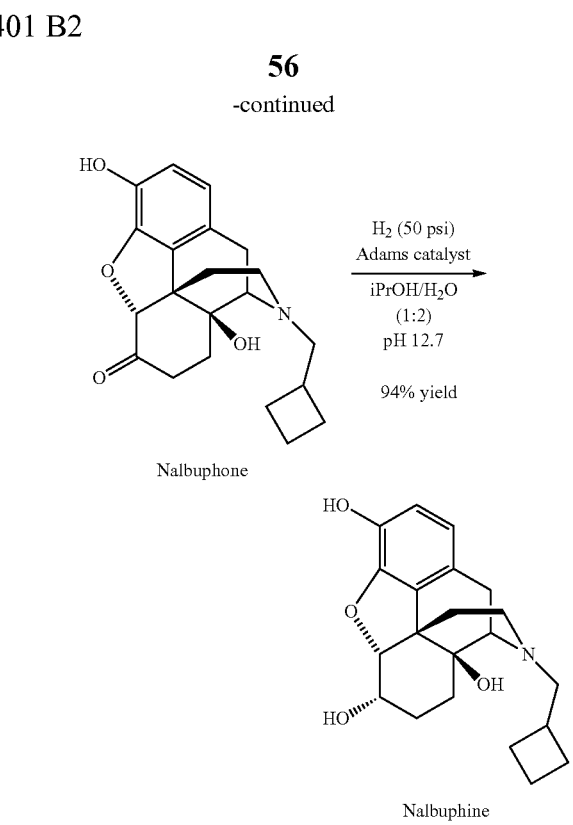

Example 15

Synthesis of Buprenorphine

Two complementary routes for buprenorphine process are compared below as shown in Schemes 16-23. Route B starting from carbonate protected CPM (27 proved to be not as advantageous as approach A, which incorporates a later stage protection (before Grignard reaction). Generally, lower yields were observed and crystallizations were problematic with (27) and (28). Approach A was improved by using toluene instead of water as a solvent of choice, which provided much better α/β selectivity. The Grignard reaction was studied from the point of view of the amount of Grignard reagents and results are shown in scheme 15. The Major side reaction was the amount of addition of t-butylmagnesium chloride to carbonate moiety but it does not represent a problem since the pivaloyl ester can be further hydrolyzed.

SCHEME 16

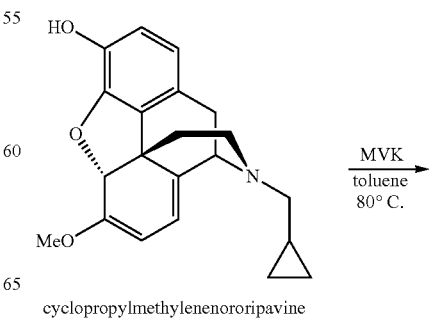

cyclopropylmethylenenororipavine

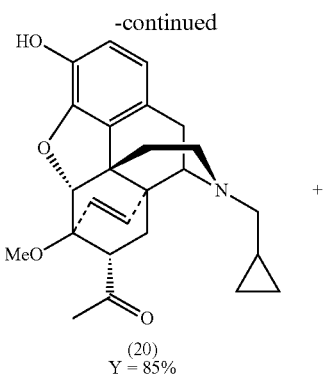

(20)
Y = 85%

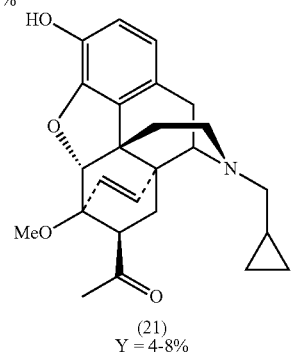

(21)
Y = 4-8%

Cyclopropylmethylenenororipavine (157 mg; 0.53 mmol) was dissolved in toluene (2.4 mL) and MVK (0.8 mL) was added. Reaction mixture was stirred with a magnetic stirbar and heated to 80° C. After 12 h TLC (ethyl acetate) analysis indicated no starting material ($R_f$=0.05), (20) ($R_f$=0.5) and MVK adduct ($R_f$=0.4). The reaction mixture was then concentrated under vacuo and the resulting light brown solid was crystallized from hot EtOH (0.4 mL) yielding white solid (20) (182 mg, 85%).

(20) (α): m.p.=211-214° C. (EtOH); $R_f$=0.5 (ethyl acetate); $[α]_D^{20}$=−236.47° (c=1, CHCl$_3$); IR (KBr, cm$^{-1}$) v 3587, 3072, 3051, 3027, 3000, 2970, 2935, 2920, 2891, 2839, 2814, 2788, 1702, 1637, 1607, 1500, 1467, 1427, 1381, 1352, 1317, 1242, 1217, 1163, 1124, 1096, 1084, 1028, 932, 822, 786, 735; $^1$H NMR (CDCl$_3$, 600 Mhz) δ 6.62 (d, 1H, J=7.8 Hz), 6.49 (d, 1H, J=7.8 Hz), 5.87 (d, 1H, J=9.0 Hz), 5.59 (d, 1H, J=9.0 Hz), 4.62 (s, 1 H), 3.60-3.57 (m, 4H), 3.11 (d, 1 H, J=18.6 Hz), 3.03 (dd, 1H, J=10.2, 12.6 Hz), 2.95 (dd, 1H, J=9.0, 9.0 Hz), 2.73 (dd, 1H, J=4.8, 12.0 Hz), 2.45-2.38 (m, 3H), 2.35 (dd, 1H, J=6.6, 12.6 Hz), 2.16 (s, 3H), 1.98 (ddd, 1 H, J=5.4, 13.2, 13.2 Hz), 1.86 (dd, 1H, J=2.4, 12.6 Hz), 1.36 (dd, 1H, J=6.6, 12.6 Hz), 0.85-0.83 (m, 1H), 0.56-0.49 (m, 2H), 0.17-0.12 (m, 2H); $^{13}$C NMR (CDCl$_3$, 125 Mhz) δ 209.31, 146.55, 137.43, 136.35, 134.05, 127.83, 125.67, 119.94, 116.33, 95.20, 81.31, 59.78, 57.06, 53.18, 50.66, 48.49, 44.01, 43.25, 33.53, 30.26, 30.04, 23.29, 9.46, 4.15, 3.46; MS (FAB+) m/z (%) 408(18), 407(13), 243(22), 242 (100), 184(11), 142(19); HRMS (FAB+) calcd for $C_{25}H_{29}N_1O_4$: 407.20966. Found 407.20175.

(21) Beta Isomer (Contains 10% of α and Unknown Impurity from MVK)

Isolated from the mother liquor after crystallization and 2 chromatographies (hexane/ethyl acetate 4:1 and toluene/ethyl acetate 3:1. Signals of MVK adduct impurity $^1$H NMR 4.40-4.20 (m, 2H), 2.87 (t, 1H, J=6.6 Hz), 2.16 (s, 3H) $^{13}$C NMR 206.77, 65.22, 43.16, 29.94.

Colourless oil. $R_f$=0.5 (ethyl acetate); $[α]_D^{20}$=−183.61° (c=1, CHCl$_3$); IR (KBr, cm$^{-1}$) v 3484, 3421, 3406, 3075, 2997, 2924, 2835, 2813, 2777, 1712, 1629, 1600, 1497, 1444, 1384, 1357, 1250, 1205, 1170, 1103, 1054, 937, 796, 587; $^1$H NMR (CDCl$_3$, 300 Mhz) δ 6.64(d, 1H, J=8.1 Hz), 6.51 (d, 1H, J=8.1 Hz), 5.90 (d, 1H, J=9.0 Hz), 5.60 (d, 1H, J=9.0 Hz), 4.57 (s, 1 H), 3.61 (s, 3H), 3.58 (dd, 1H, J=6.3, 11.7 Hz), 3.11 (d, 1 H, J=18.3 Hz), 3.08-2.90 (m, 2H), 2.72 (dd, 1H, J=4.5, 11.7 Hz), 2.48-2.28 (m, 4H), 2.22 (s, 3H), 1.98 (ddd, 1 H, J=5.1, 12.0, 12.0 Hz), 1.85 (dd, 1H, J=2.7, 12.9 Hz), 1.37 (dd, 1H, J=5.7, 12.0 Hz), 0.91-0.77 (m, 1H), 0.57-0.47 (m, 2H), 0.19-0.09 (m, 2H); $^{13}$C NMR (CDCl$_3$, 75 Mhz) δ 209.29, 148.55, 140.37, 136.36, 134.64, 129.15, 125.61, 119.56, 116.26, 95.60, 81.35, 59.77, 56.98, 53.56, 50.80, 48.11, 43.95, 43.37, 33.58, 30.60, 30.55, 23.29, 9.46, 4.14, 3.40; MS (FAB+) m/z (%) 408 (26), 407 (16), 326 (14), 246 (28); HRMS (FAB+) calcd for $C_{25}H_{30}N_1O_4$: 408.21748. Found 408.21428.

Signals of MVK adduct impurity $^1$H NMR 4.40-4.20 (m, 2H), 2.87 (t, 1H, J=6.6 Hz), 2.16 (s, 3H) $^{13}$C NMR 206.77, 65.22, 43.16, 29.94

Scheme 17

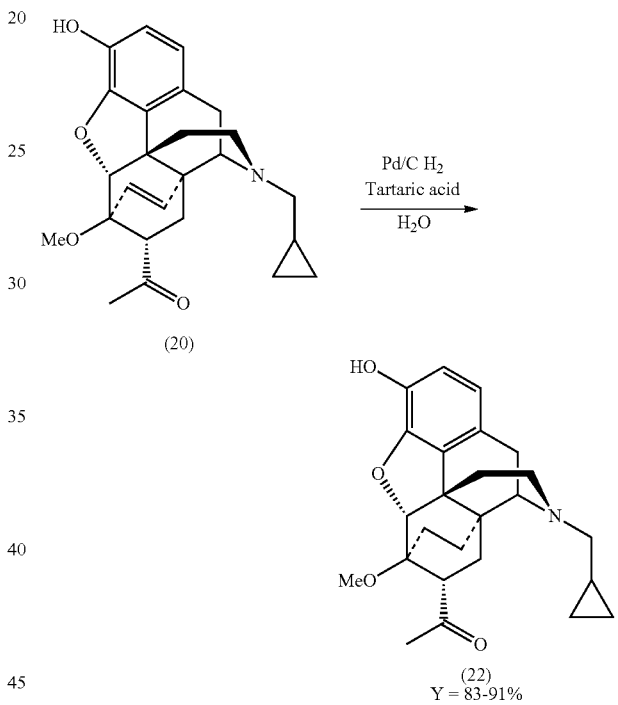

(20) (1.64 g; 4.01 mmol), tartaric acid (642 mg; 4.01 mmol) and Pd/C (450 mg; 10 wt %) were suspended in deionized water (15 mL). The flask was then evacuated/refilled with H$_2$ gas (four cycles) and subjected to H$_2$ atm (1 atm.). The reaction mixture was then stirred at 80° C. for 16 h. TLC (ethyl acetate) analysis showed only traces of starting material ($R_f$=0.5) and majority of (22) ($R_f$=0.4). TLC sample was prepared by extraction of few drops of reaction mixture between ethyl acetate (0.5 mL) and sat. solution of NaHCO$_3$ (0.5 mL). The hot reaction mixture was then filtered through 0.7 cm pad of celite, which was then washed with hot deionized water (70° C., 2×2 mL). After cooling to room temperature. the pH of the filtrate was adjusted to 6.60-6.70 (40% KOH; 930 µl) upon vigorous stirring. The resulting white precipitate was then filtered off and dried overnight under vacuum at 50° C. to yield a porous white solid (1.52 g). $^1$H NMR showed that this material contains ~3% of starting (20) and ~3% of corresponding β isomer. Chromatography (10 mL silica, hexane/ethyl acetate 1:1) of 150 mg of this material afforded 135 mg of pure (22). To this end, it was determined that the bulk material contained ~10% of water and inorganic impurities. Estimated yield of (22)=1.37 g (83%).

(22) (α): m.p.=170-172° C. (EtOH), 166-168° C. (crude evaporated from ethyl acetate); $R_f$=0.4 (ethyl acetate); $[α]_D^{20}$=−109.93° (c=1, CHCl$_3$); IR (KBr, cm$^{-1}$) ν 3463, 3075, 2956, 2924, 2874, 2853, 2813, 2777, 1709, 1647, 1610, 1502, 1458, 1384, 1356, 1331, 1283, 1160, 1095, 1030, 958, 820, 702, 636, 590; $^1$H NMR (CDCl$_3$, 300 Mhz) δ 6.70 (d, 1H, J=8.1 Hz), 6.53 (d, 1H, J=8.1 Hz), 4.51 (d, 1 H, J=1.8 Hz), 3.43 (s, 3H), 3.10-3.04 (m, 2H), 2.97 (d, 1 H, J=18.3 Hz), 2.76 (ddd, 1H, J=3.9, 11.4, 13.5 Hz), 2.65 (dd, 1H, J=5.1, 12.0 Hz), 2.37-2.23 (m, 7H), 2.05 (ddd, 1H, J=5.7, 12.6, 12.6 Hz), 1.74 (dd, 1 H, J=6.3, 13.2 Hz), 1.69-1.40 (m, 3H), 1.30 (ddd, 1H, J=8.7, 12.3, 12.3 Hz), 0.83-0.64 (m, 2H), 0.54-0.40 (m, 2H), 0.15-0.05 (m, 2H); $^{13}$C NMR (CDCl$_3$, 75 Mhz) δ 210.94, 145.26, 137.37, 132.37, 128.21, 119.66, 116.54, 94.76, 77.81, 59.81, 58.38, 52.08, 49.52, 46.70, 43.76, 35.54, 35.18, 33.63, 30.46, 28.58, 22.84, 17.58, 9.42, 4.08, 3.37; MS (+EI) m/z (%) 409(6), 368(5), 155(2), 149(4), 129(5), 123(4), 113 (7), 112(9), 111(6); HRMS (+EI) calcd for $C_{25}H_{31}N_1O_4$: 409.22531. Found 409.22610; Anal. Calcd for $C_{25}H_{31}N_1O_4$: C, 73.32; H, 7.63. Found C, 73.22; H, 7.59.

under vacuo. $^1$H NMR of the crude product showed essentially pure (23) and traces of toluene. The crude product (520 mg) was then dissolved in EtOH (2.5 mL) at 55° C. and crystallized overnight in freezer giving 320 mg (~61%) of white crystals with slight yellow tinge. If chromatography (30 mL silica, hexane/ethyl acetate 4:1) was used for purification, the yield was 498 mg (95%).

(23): m.p.=105-107° C. (MeOH); $R_f$=0.3-0.4 (ethyl acetate/hexane 1:1); $[α]_D^{20}$=−148.51° (c=1, CHCl$_3$); IR (KBr, cm$^{-1}$) ν 3077, 2965, 2930, 2837, 2812, 2778, 2745, 2255, 1764, 1711, 1614, 1492, 1451, 1384, 1369, 1356, 1259, 1243, 1200, 1163, 1130, 1095, 1063, 1024, 993, 958, 878, 781, 731, 639, 568; $^1$H NMR (CDCl$_3$, 300 Mhz) δ 6.88 (d, 1H, J=8.1 Hz), 6.62 (d, 1H, J=8.1 Hz), 4.51 (d, 1 H, J=1.5 Hz), 4.28 (q, 2H, J=7.2 Hz) 3.38 (s, 3H), 3.09-2.98 (m, 3H), 2.74 (ddd, 1H, J=3.9, 9.6, 13.5 Hz), 2.65 (dd, 1 H, J=5.1, 12.0 Hz), 2.37-2.23 (m, 7H), 2.05 (ddd, 1H, J=5.4, 12.6, 12.6 Hz), 1.78-1.61 (m, 3H), 1.53 (dddd, 1H, J=~1, ~1, 12.9, 12.9 Hz), 1.36 (t, 3H, J=7.2 Hz), 1.29 (dd, 1H, J=6.0, 12.0 Hz), 0.80-0.73 (m, 1H), 0.69-0.65 (m, 1H), 0.54-0.43 (m, 2H), 0.13-0.05 (m, 2H); $^{13}$C NMR (CDCl$_3$, 75 Mhz) δ 210.95, 153.16, 149.49, 134.60, 133.77, 131.93, 121.76, 119.30, 96.69, 77.55, 64.92, 59.80, 58.25, 52.40, 50.02, 46.06, 43.58, 35.43, 34.87, 33.93, 30.26, 28.64, 23.25, 16.56, 14.18, 9.43, 4.08, 3.37; MS (FAB+) m/z (%) 482(100), 481(78), 480(2), 450 (21), 440(25), HRMS (FAB+) calcd for $C_{28}H_{36}N_1O_6$: 482.25426.

Found 482.25078. Anal. Calcd for $C_{28}H_{35}N_1O_6$: C, 69.83; H, 7.33. Found C, 69.53; H, 7.30.

Scheme 18

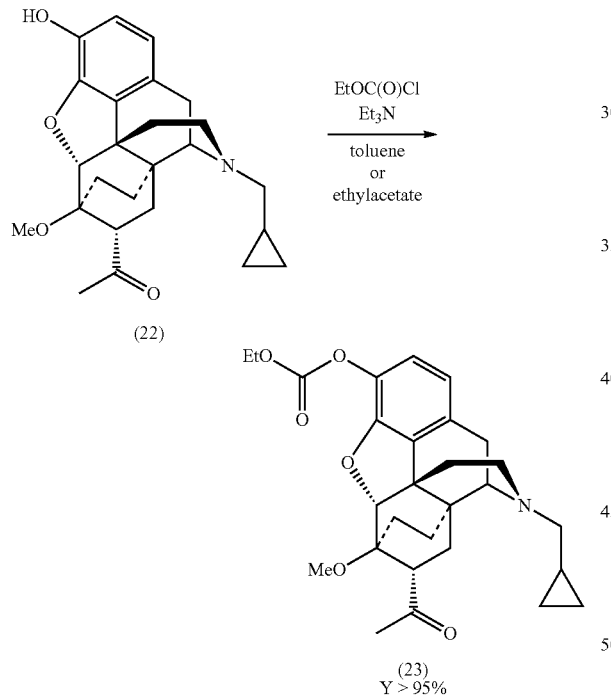

To a suspension of (22) (0.5 g, ~1.21 mmol; ~90% purity;) in warm toluene (10 mL, 40° C.) was added ethylchloroformate (171 mg, 1.58 mmol) and triethylamine (271 μl, 1.94 mmol). Upon addition of triethylamine most of (22) was dissolved and the reaction mixture turned a slight-yellow colour followed by red. TLC (ethyl acetate/hexane 1:1) analysis after 10 min. showed disappearance of starting material and a major spot of (23) ($R_f$=0.3-0.4) accompanied by very minor spots of two impurities ($R_f$=0.4, 0.45). After stirring for an additional 30 min. stirring at room temperature. the reaction mixture was filtered through a short pad of celite and triethylaminehydrochloride and other inorganic material from previous step were filtered off. Filtration bed was then washed with toluene (2×2.5 mL) and the filtrate concentrated Scheme 19

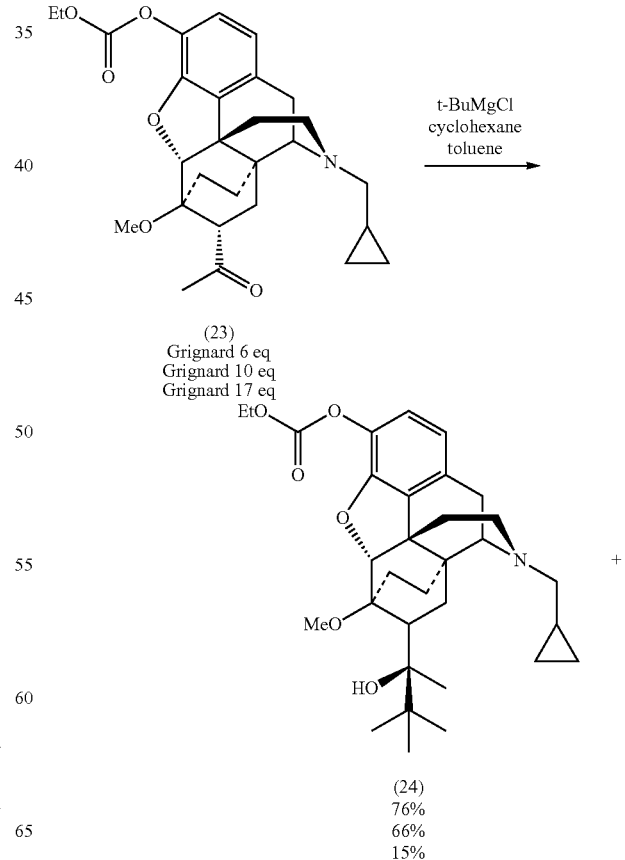

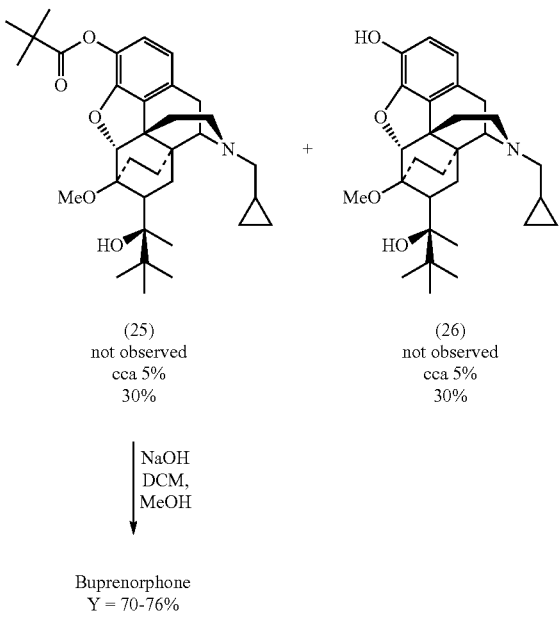

(25)
not observed
cca 5%
30%

(26)
not observed
cca 5%
30%

| NaOH
DCM,
MeOH

Buprenorphone
Y = 70-76%

A solution of (23) (109 mg, 2.265 mmol) in toluene (1 mL) was added dropwise to a vigorously stirred suspension of t-butylmagnesiumchloride in hexane (2.3 mL; 1M suspension) at room temperature. After 35 min. of stirring TLC (hexane/ethyl acetate 1:1) analysis showed disappearance of all starting material and a major spot of (24) ($R_f$=0.8), traces of buprenorphine (26) ($R_f$=0.6), and a by-product (25) ($R_f$=0.1). (TLC sample was prepared by extraction of few drops of reaction mixture between ethyl acetate (0.5 mL) and sat. NaHCO$_3$ (0.5 mL). Reaction was then quenched by careful addition of water (2 mL) to reaction mixture at room temperature which led to a release of isobutane and heat (~45° C.). The reaction mixture was then diluted with ethyl acetate (30 mL) and extracted with sat. NH$_4$Cl (4 mL). The aqueous layer (pH 7-8, paper) was then reextracted with ethyl acetate (2×10 mL). The combined organic layer was dried with MgSO$_4$, filtered and concentrated under vacuo. Content of (24) in crude $^1$H NMR was estimated to be 84%. The crude mixture was then dissolved in MeOH (3 mL) and dichloromethane (2 mL) and 5% NaOH (0.91 mL, 5 eq) was added dropwise. Immediately after addition of hydroxide reaction turned a brown-red colour. After 10 min TLC (hexane/ethyl acetate 1:1) analysis showed complete hydrolysis of starting material and major spot of buprenorphine $R_f$=0.6 accompanied by two minor spots $R_f$=0.65, 0.2. Reaction mixture was then diluted with dichloromethane (50 mL) and washed with sat. solution NH$_4$Cl (5 mL). Aqueous layer (pH 7-8, paper) was reextracted with dichloromethane (10 mL). Combined organic layer was dried with MgSO$_4$ and concentrated under vacuo. Chromatography (8 mL silica; hexane/ethyl acetate 4:1→2:1) afforded buprenorphine (26) as slight yellowish crystals (80 mg; 76%).

t-butylmagnesiumchloride was prepared from 2 g of Mg turnings, 6.94 mL THF, 9.8 g t-BuCl, 24.5 mL cyclohexane. An aliquot of Grignard reagent (~1 mL) was dissolved in solution of 1,10-phenatroline monohydrate (1-2 mg) in 4 mL THF and titrated with 1M solution of menthol in THF until loss of purple color of magnesium-phenantroline complex. Grignard reagent was used as a slurry.

(24) (α): m.p.=125-128° C. (MeOH); $R_f$=0.8 (ethyl acetate/hexane 1:1); $[\alpha]_D^{20}$=−138.56° (c=1, CHCl$_3$); IR (KBr, cm$^{-1}$) v 3443, 3077, 2979, 2954, 2928, 2878, 2846, 2812, 2777, 1763, 1614, 1491, 1451, 1402, 1384, 1370, 1338, 1303, 1247, 1201, 1164, 1134, 1077, 1021, 979, 877, 781, 731, 586; $^1$H NMR (CDCl$_3$, 300 Mhz) δ 6.88 (d, 1H, J=8.1 Hz), 6.61 (d, 1H, J=8.1 Hz), 5.93 (s, 1H) 4.47 (d, 1 H, J=1.5 Hz), 4.27 (q, 2H, J=7.2 Hz) 3.51 (s, 3H), 3.05 (d, 1H, J=10.8 Hz) 3.01 (s, 1H), 2.90 (ddd, 1 H, J=3.6, 9.9, 13.5 Hz), 2.63 (dd, 1H, J=5.1, 11.7 Hz), 2.40-2.17 (m, 4H), 2.14 (dd, 1H, J=9.9, 9.9 Hz) 1.99 (ddd, 1H, J=5.7, 12.9, 12.9 Hz), 1.93-1.77 (m, 2H), 1.73 (dd, 1H, J=2.4, 12.6 Hz), 1.40-1.28 (m, 7H), 1.17-0.97 (m, 10H), 0.85-0.77 (m, 1H), 0.73-0.64 (m, 1H), 0.56-0.45 (m, 2H), 0.17-0.08 (m, 2H); $^{13}$C NMR (CDCl$_3$, 75 Mhz) δ 153.24, 149.63, 134.76, 134.01, 131.85, 121.71, 119.29, 98.26, 80.67, 79.27, 64.91, 59.51, 58.10, 52.59, 46.29, 44.30, 43.53, 40.35, 35.97, 35.37, 33.35, 29.77, 26.42, 23.32, 19.94, 17.51, 14.19, 9.48, 4.18, 3.25; MS (FAB+) m/z (%) 538(69), 522(57), 482(37), 450(49), 438(17); HRMS (FAB+) calcd for $C_{32}H_{45}N_1O_6$: 539.32469. Found 539.32634.

(25):

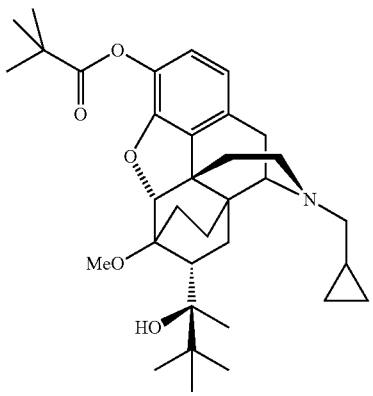

m.p.=142-144° C. (MeOH); $R_f$=0.9 (ethyl acetate/hexane 2:1); $[\alpha]_D^{23}$=−151.478° (c=1, CHCl$_3$); IR (KBr, cm$^{-1}$) v 3433, 3066, 2977, 2955, 2936, 2913, 2876, 2822, 2775, 1754, 1614, 1480, 1449, 1406, 1384, 1280, 1244, 1206, 1117, 1075, 1021, 960, 885, 783, 598; $^1$H NMR (CDCl$_3$, 300 Mhz) δ 6.77 (d, 1H, J=8.1 Hz), 6.60 (d, 1H, J=8.1 Hz), 5.94 (s, 1H) 4.43 (d, 1 H, J=1.5 Hz), 3.47 (s, 3H), 3.04 (d, 1H, J=12.3 Hz) 3.00 (s, 1H), 2.90 (ddd, 1 H, J=3.6, 10.8, 13.8 Hz), 2.63 (dd, 1H, J=4.8, 11.7 Hz), 2.40-2.23 (m, 4H), 2.12 (dd, 1H, J=9.9, 9.9 Hz) 1.98 (ddd, 1H, J=5.4, 12.6, 12.6 Hz), 1.94 (m, 1H), 1.82 (m, 1H), 1.72 (dd, 1 H, J=2.4, 12.9 Hz), 1.36 (s, 3H), 1.33 (s, 9H), 0.99 (s, 9H), 0.85-0.77 (m, 1H), 0.69 (dddd, 1H, J=3.6, 3.6, 12.6, 12.6 Hz), 0.56-0.45 (m, 2H), 0.17-0.09 (m, 2H); $^{13}$C NMR (CDCl$_3$, 75 Mhz) δ 176.44, 149.93, 134.31, 133.66, 131.78, 121.99, 119.26, 98.15, 80.71, 79.24, 59.52, 58.15, 52.54, 46.32, 44.52, 43.57, 40.33, 38.93, 36.01, 35.39, 33.39, 29.78, 27.18, 26.43, 23.31, 19.88, 17.37, 9.49, 4.17, 3.25; MS (FAB+) m/z (%) 552(39), 551(37), 550(75), 534(65), 494 (45); HRMS (FAB+) calcd for $C_{34}H_{50}N_1O_5$: 552.36890. Found 552.36661; Anal. Calcd for $C_{34}H_{49}N_1O_5$: C, 74.01; H, 8.95.

Found C, 74.24; H, 9.15.

Alternative Route

Scheme 20

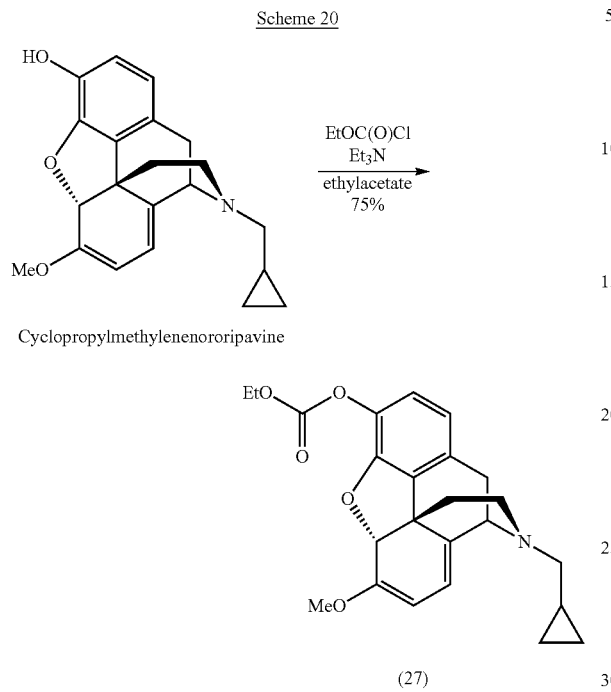

Cyclopropylmethylenenororipavine (CPMNO) (400 mg, 1.19 mmol) was suspended in ethyl acetate (4 mL) at room temperature and ethyl chloroformate (124 μl, 1.30 mmol) was added to suspension in one portion followed by Et₃N (215 μl, 1.54 mmol). Reaction mixture was stirred at room temperature. for 5 h then diluted with ethyl acetate (50 ml) and washed with saturated solution of NaHCO₃ (10 mL). Aqueous layer was re-extracted with ethyl acetate (10 mL), combined organic layers dried with MgSO₄ and concentrated under vacuum. Crystallization of crude product from acetone (3 mL) afforded white crystals of (27) (316 mg, 65%). Mother liquor was concentrated an re-crystallized from mixture acetone/cyclohexane (0.5 ml, 1:1) giving additional 15 mg (10%) of (27).

m.p. 157-158° C. (EtOH); $R_f$ 0.33 (ethyl acetate/methanol 4:1); $[\alpha]^{20}_D = -97.80$ (c=1, CHCl₃); IR(CHCl₃) ν 2997, 2933, 2837, 1761, 1608, 1446, 1370, 1261, 1023, 866 cm⁻¹; ¹H NMR (600 MHz, CDCl₃) δ 6.86 (d, J=8.1 Hz, 1H), 6.63 (d, J=8.1 Hz, 1H), 5.59 (d, J=6.4 Hz, 1H), 5.34 (s, 1H), 5.07 (d, J=6.4 Hz, 1H), 4.33 (dq, J=7.2, 0.9 Hz, 2H) 3.96 (d, J=6.8 Hz, 1H), 3.62 (s, 3H), 3.28 (d, J=18.1 Hz, 1H), 2.92 (dd, J=13.0, 4.5 Hz, 1H), 2.81 (ddd, J=12.7, 12.7, 3.0, 1H), 2.74 (dd, J=18.1, 6.9 Hz, 1H), 2.50 (d, J=6.4 Hz, 2H), 2.22 (ddd, J=12.6, 12.6, 5.1, 1H), 1.77 (dd, J=12.6, 1.7, 1H), 1.38 (t, J=7.2 Hz, 3H), 0.93 (m, 1H), 0.57 (m, 2H), 0.17 (dd, J=9.7, 4.8, 2H); ¹³C (150 MHz, CDCl₃) δ 153.23, 152.26, 147.51, 134.82, 133.50, 132.75, 132.27, 121.46, 119.29, 112.01, 96.34, 90.03, 64.90, 59.07, 58.36, 55.07, 46.50, 44.12, 36.60, 30.92, 14.16, 9.46, 3.95, 3.81; MS (+EI) m/z (%): 42 (23), 55(45), 253 (25), 277 (41), 308 (23), 363 (100), 409 (14); HRMS calcd for C₂₄H₂₇NO₅ 409.1889, found 409.18892.

Scheme 21

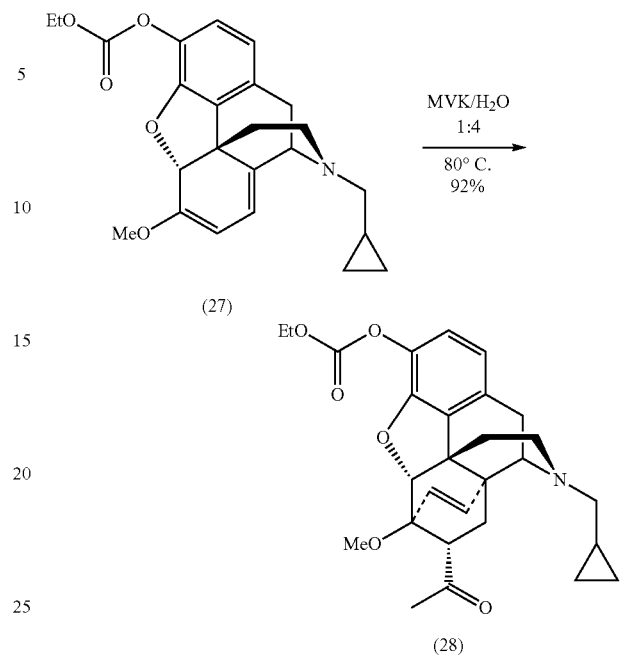

(27) (243 mg, 0.59 mmol) was suspended in distilled water (1.5 mL) at room temperature and methylvinyl ketone (MVK) (0.4 mL) was added. For better stirring seasand (0.5 g) was added to the reaction vessel and mixture was stirred by magnetic stir-bar at 80° C. for 12 h. The mixture was then diluted with EtOH (10 mL) and was filtered off and filtrate concentrated under vacuo. Chromatography (11.5 mL silica, hexane/ethyl acetate 5:1-4:1) afforded 261 mg (92%) (28) as white oil.

Scheme 22

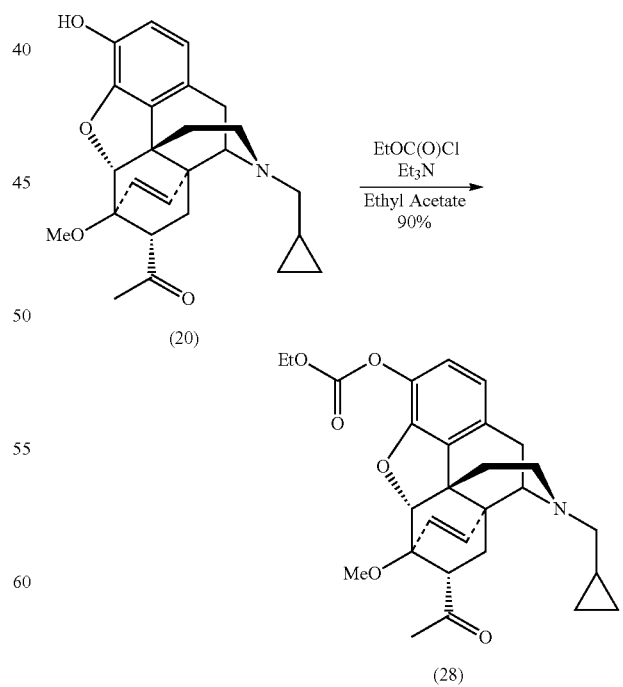

(20) (127 mg, 0.31 mmol) was suspended in ethyl acetate (2 mL) at room temperature and ethyl chloroformate (39 μl, 0.41 mmol) was added to suspension in one portion followed by Et$_3$N (70 μl, 0.50 mmol). Reaction mixture was stirred at room temperature. 3 h then diluted with ethyl acetate (40 ml) and washed with saturated solution of NaHCO$_3$ (8 mL). Aqueous layer was re-extracted with ethyl acetate (8 mL), combined organic layers dried with MgSO$_4$ and concentrated under vacuum. Chromatography (8 mL silica, hexane/ethyl acetate 2:1) afforded (28) (135 mg, 90%) as a white oil.

(28): $R_f$=0.25 (hexane/ethyl acetate 3:1); $[\alpha]_D^{20}$=−200.85° (c=1, CHCl$_3$); IR (KBr, cm$^{-1}$) ν 3448, 3431, 3076, 2995, 2933, 2834, 2813, 2777, 1765, 1704, 1614, 1492, 1451, 1384, 1370, 1358, 1241, 1201, 1167, 1099, 1062, 1023, 977, 780; $^1$H NMR (CDCl$_3$, 300 Mhz) δ 6.79 (d, 1H, J=8.1 Hz), 6.56 (d, 1H, J=8.1 Hz), 5.94 (d, 1H, J=8.7 Hz), 5.60 (d, 1H, J=9.0 Hz), 4.62 (s, 1 H), 4.28 (q, 2H, J=7.2 Hz), 3.59-3.57 (m, 4H), 3.14 (d, 1 H, J=18.6 Hz), 3.00 (dd, 1H, J=9.6, 11.7 Hz), 2.91 (dd, 1H, J=9.3, 6.3 Hz), 2.73 (dd, 1H, J=4.5, 12.0 Hz), 2.50-2.30 (m, 4H), 2.16 (s, 3H), 1.97 (ddd, 1 H, J=5.4, 12.6, 12.6 Hz), 1.90 (dd, 1H, J=2.7, 12.9 Hz), 1.36 (t, 3H, J=7.2 Hz), 0.83 (m, 1H), 0.54-0.50 (m, 2H), 0.17-0.11 (m, 2H); $^{13}$C NMR (CDCl$_3$, 75 Mhz) δ 209.16, 153.09, 150.79, 136.23, 135.52, 133.99, 131.90, 125.45, 121.40, 119.57, 97.06, 81.31, 77.47, 64.88, 59.76, 56.90, 53.93, 50.89, 48.24, 43.82, 43.15, 33.25, 30.77, 29.81, 23.68, 14.18, 9.45, 4.14, 3.41; MS (FAB+) m/z (%) 480 (100), 436 (21), 328 (14), 246(31); HRMS (FAB+) calcd for C$_{28}$H$_{34}$N$_1$O$_6$: 480.23861. Found 408.23383.

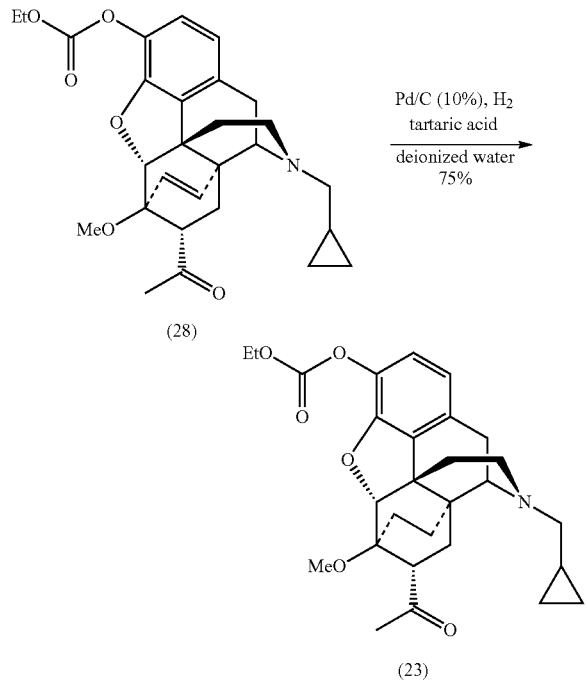

Scheme 23

(28) (135 mg; 0.28 mmol), tartaric acid (42 mg; 0.28 mmol) and Pd/C (25 mg; 10 wt %) were suspended in deionized water (2 mL). The flask was then four times evacuated/refilled with H$_2$ gas and subjected to H$_2$ atm (1 atm.). The reaction mixture was then stirred at 80° C. for 16 h. The hot reaction mixture was then filtered through 0.5 cm pad of celite, which was then washed with hot deionized water (70° C., 2×1 mL). After cooling to room temperature. the filtrate was partitioned between ethyl acetate (15 mL) and NaHCO$_3$ solution (5 mL). The organic layer was dried with MgSO$_4$ and concentrated under vacuo. Chromatography (8 mL silica, hexane/ethyl acetate 2:1) afforded (23) (113 mg, 75%) as a white solid.

Example 16

HPLC Method for the Resolution of (R)- and (S)-Isomers of Methylnaltrexone

All analyses were performed on an Agilent 1100 Series HPLC comprised of 1100 Series Autosampler, Quaternary Pump, and Variable Wavelength Detector. All solvents were of HPLC grade unless otherwise noted.

Column: Phenomenex Primesphere 5 C18 HC (4.6×150 mm, 5.0 μm)
Column Temperature: 50° C.
Mobile Phase A: 95:5 (v/v) H$_2$O/Methanol (0.1% TFA)
Mobile Phase B: 35:65 (v/v) H$_2$O/Methanol (0.1% TFA)
Flow Rate: 0.7 mL/min
Detection: 280 nm
Sample Diluent: 70% 5 mM KH$_2$PO$_4$(aq) (0.1% Triethylamine, pH=2.8)
30% Methanol

| Time (min) | % Mobile Phase A | % Mobile Phase B |
|---|---|---|
| 00:00 | 100 | 00 |
| 50:00 | 40 | 60 |
| 51:00 | 100 | 00 |
| 60:00 | 100 | 00 |

A sample chromatogram is shown in FIG. 1.

Example 17

HPLC Method for the Resolution of (R)- and (S)-Isomers of Quaternized Oripavine, Cyclopropylmethylene Nororipaine and Naltrexone Column: Phenomenex Primesphere 5 C18 HC (4.6×150 mm, 5.0 μm)
Column Temperature: 50° C.
Mobile Phase A: MeOH
Mobile Phase B: 5 mM KH$_2$PO$_4$(aq) (0.1% Triethylamine, pH=2.8)
Flow Rate: 1.3 mL/min
Detection: 280 nm
Sample Diluent: 70% B, 30% A

| Time (min) | % Mobile Phase A | % Mobile Phase B |
|---|---|---|
| 00:00 | 5 | 95 |
| 55:00 | 30 | 70 |
| 56:00 | 5 | 95 |
| 65:00 | 55 | 95 |

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Quaternization of Oripavine

| Entry | Conditions | Conversion[a] | Yield[a] | Ratio (S:R)[a] |
|---|---|---|---|---|
| 1 | $CHCl_3$, 80° C., sealed tube, 18 hrs, 10 equiv. CPM-Br | 98% | 94% | 2.26:1 |
| 2 | $CHCl_3$, 80° C., sealed tube, 18 hrs, 10 equiv. CPM-I | 96% | 86% | 2.58:1 |
| 3 | NMP, 80° C., 18 hrs, 15 equiv. CPM-Br | 97% | 88% | 1.36:1 |
| 4 | NMP, 80° C., 18 hrs, 15 equiv. CPM-CI | 60% | 57% | 1.89:1 |
| 5 | NMP, 80° C., 18 hrs, 15 equiv. CPM-I | 97% | 77% | 1.96:1 |
| 6 | NMP, 110° C., 21 hrs, 15 equiv. CPM-CI | 89% | 73% | 1:1.45 |
| 7 | NMP, 120° C., 18 hrs, 15 equiv. CPM-CI | 95% | 67% | 1:3.56 |
| 8 | NMP, 120° C., 28 hrs, 15 equiv. CPM-CI | 95% | 58% | 1:7 |
| 9 | NMP, microwave, 3 min, 10 equiv. CPM-Br | 91% | 84% | 1.5:1 |

[a] determined by HPLC (see Example 16)

TABLE 2

Demethylation of cyclopropylmethylene oripavine salt with t-dodecanethiolate

| Entry | Substrate | Solvent | Scale | Conditions | Yield |
|---|---|---|---|---|---|
| 1 | (R)-oripavine salt | DMSO | 200 mg | 80° C., 45 min. chromatography crystallization | 71% |
| 2 | (R)-oripavine salt | DMSO | 200 mg | 100° C., 10 min. chromatography crystallization | 77% |
| 3 | (S)-oripavine salt | DMSO | 220 mg | 80° C., 55 min. chromatography | 63% |

What is claimed is:

1. A process for preparing intermediates useful in the synthesis of morphinane and morphinone compounds comprising:

(a) reacting a compound of the formula (II) with a compound of the formula (III) under conditions to form compounds of the formulae R-(Ia) and S-(Ib):

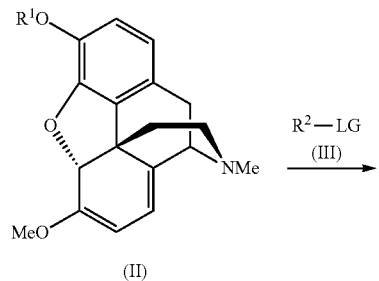

(II)

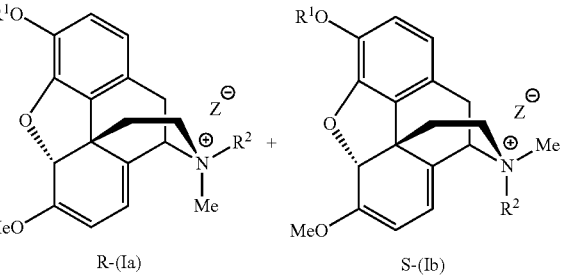

R-(Ia)     S-(Ib)

wherein
$R^1$ is selected from hydrogen, $C_{1-6}$alkyl, $C(O)C_{1-6}$alkyl and PG;
$R^2$ is selected from $R^3$, $C(O)R^3$, $S(O)R^3$ and $SO_2R^3$;
$R^3$ is selected from $C_{2-6}$alkyl, $C_{1-6}$alkyleneC$_{3-8}$cycloalkyl, $C_{1-6}$alkyleneC$_{6-10}$aryl, $C_{1-6}$alkyleneC$_{1-8}$heterocyclyl and $C_{1-6}$alkyleneC$_{1-10}$heteroaryl;
LG is a leaving group;
PG is a protecting group;
Z is a suitable counter anion; and
each alkyl, alkylene and aryl is optionally fluoro-substituted and/or deuterated; and (b) isolating the compound of the formula R-(Ia); and (c) treating the remaining side products, including the compound of the formula S-(Ib) and a mixture of the compounds of the formulae R-(Ia) and S-(Ib) under N-demethylation conditions to form a compound of the formula (IV):

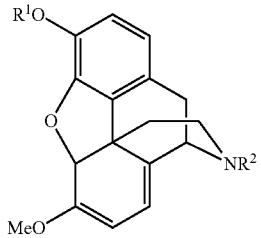

(IV)

wherein
$R^1$ is selected from hydrogen, $C_{1-6}$alkyl, $C(O)C_{1-6}$alkyl and PG;
$R^2$ is selected from $R^3$, $C(O)R^3$, $S(O)R^3$ and $SO_2R^3$;
$R^3$ is selected from $C_{2-6}$alkyl, $C_{1-6}$alkyleneC$_{3-8}$cycloalkyl, $C_{1-6}$alkyleneC$_{6-10}$aryl, $C_{1-6}$alkyleneC$_{1-8}$heterocyclyl and $C_{1-6}$alkyleneC$_{1-10}$heteroaryl;
PG is a protecting group;
and
each alkyl, alkylene and aryl is optionally fluoro-substituted and/or deuterated.

2. The process of claim 1, wherein the conditions to form the compounds of the formulae R-(Ia) and S-(Ib) comprise treating the compound of formula (II) in a suitable solvent at a temperature of about 40° C. to about 200° C., with addition of excess amounts of the compound of formula (III).

3. The process of claim 1, wherein the conditions to form the compounds of the formulae R-(Ia) and S-(Ib) comprise reacting the compound of formula (II) with excess amounts of the compound of formula (III) in suitable solvent at a temperature of about 40 ° C. to about 200° C., the reaction mixture is then cooled and treated with a suitable base, followed by treatment with further amount of the compound of formula (III) and heating to a temperature of about 40° C. to about 200° C. to provide a final reaction mixture.

4. The process of claim 3, wherein the final reaction mixture is cooled and is filtered to provide a product that comprises R-(Ia) the major isomer and a filtrate.

5. The process of claim 4, wherein the filtrate is treated to precipitate, a further product which comprises the S-isomer (Ib) as the major isomer.

6. The process of claim 2, wherein the suitable solvent for reacting the compound of the formula (II) with the compound of the formula (III) is selected from chloroform, dichloromethane (DCM), N-methylpyrrolidone (NMP), acetonitrile, dimethylformamide (DMF), dimethylpropylidene urea (DMPU), dimethylacetamide, morpholine, hexamethylphosphoramide (HMPA), alcohols (for e.g., methanol, ethanol, 1-octanol), nitromethane, acetone, dioxane, 3-butanone, toluene, dimethyl sulfoxide (DMSO), naphthalene, dimethylbenzamide, ionic liquids (for e.g., ethylammonium nitrate, 1-butyl-3-methylimidazolium (BMIM) salt), fluorous phase and any aliphatic, heteroaliphatic, heterocyclic (ring size 3-10 atoms), and carbocyclic (ring size 3-10 atoms) solvent, and mixtures thereof.

7. The process of claim 6, wherein the suitable solvent for reacting the compound of the formula (II) with the compound of the formula (III) is selected from chloroform, N-methyl saturated heterocycles and DMF.

8. The process of claim 1, wherein the reaction of the compound of the formula (II) with the compound of the formula (III) is performed at a temperature of about 40° C. to about 200° C. for about 1 minute to about 48 hours.

9. The process of claim 1, wherein the compound of the formula (III) is added continuously or in several portions to the compound of the formula (II).

10. The process of claim 1, wherein the compound of the formula R-(Ia) isomer is isolated using recrystallization, chromatography, differential precipitation and/or derivatization with another chiral molecule.

11. The process of claim 1, wherein the N-demethylation conditions to form the compound of formula (IV) comprise treating the compound of the formula S-(Ib) or the mixture of the compound of the formula R-(Ia) and S-(Ib) with a suitable nucleophile under conditions to form the compound of the formula (IV).

12. The process of claim 11, wherein the suitable nucleophile is a salt of a halide, $RS^-$, $RSe^-$, $R_2N^-$, $R_2P^-$, $RC(O)O^-$ or $RC(O)S^-$ or is $R_3N$, wherein R is any suitable aliphatic, heteroaliphatic, cycloaliphatic, heterocyclic, aryl or heteroaryl group, or inorganic sulfur, selenium, phosphorous or nitrogen salts.

13. The process of claim 12, wherein the suitable nucleophile is a thiolate nucleophile.

14. The process of claim 13, wherein the thiolate nucleophile is a salt of $C_{1-20}$alkylS$^-$ or $C_{6-18}$arylS$^-$, or an inorganic thiolate salt.

15. The process of claim 11, herein the N-demethylation conditions to form the compound of formula (IV) further comprise a suitable solvent at a temperature of about 40° C. to about 150° C.

16. The process of claim 1, wherein $R^1$ in the compounds of formulae R-(Ia), S-(Ib), (II) and (IV) is selected from hydrogen, methyl and —C(O)—$C_{1-4}$alkyl.

17. The process of claim 1, wherein $R^2$ in the compounds of formulae R-(Ia), S-(Ib), (III) and (IV) is $R^3$ and $R^3$ is selected from $C_{2-4}$alkyl, $C_{1-4}$alkylene$C_{3-6}$cycloalkyl, $C_{1-4}$alkylene $C_{6-10}$aryl, $C_{1-4}$alkylene$C_{3-6}$heterocyclyl and $C_{1-6}$alkylene $C_{6-10}$heteroaryl.

18. The process of claim 17, wherein $R^3$ is $C_{1-4}$alkylene $C_{3-6}$cycloalkyl.

19. The process of claim 18, wherein $R^3$ is $CH_2$cyclopropyl or $CH_2$cyclobutyl.

20. The process of claim 1, wherein Z in the compounds of formulae R-(Ia) and S-(Ib) is halogen, mesylate, tosylate or brosylate.

21. The process of claim 20, wherein Z is bromine.

22. The process of claim 1, wherein the compound of the formula R-(Ia) is used for preparing R-methylnaltrexone, or analogs thereof of the formula R-(VIa), by:
(a) reacting a compound of the formula R-(Ia) with a source of singlet oxygen under conditions to form a compound of the formula R-(Va); and
(b) reducing the compound of the formula R-(Va) under conditions to form the compound of the formula R-(VIa) or reducing the compound of the formula R-(Va) under conditions to form the compound of the formula R-(VIIa) followed by reducing the compound of the formula R-(VIIa) under conditions to form the compound of the formula R-(VIa):

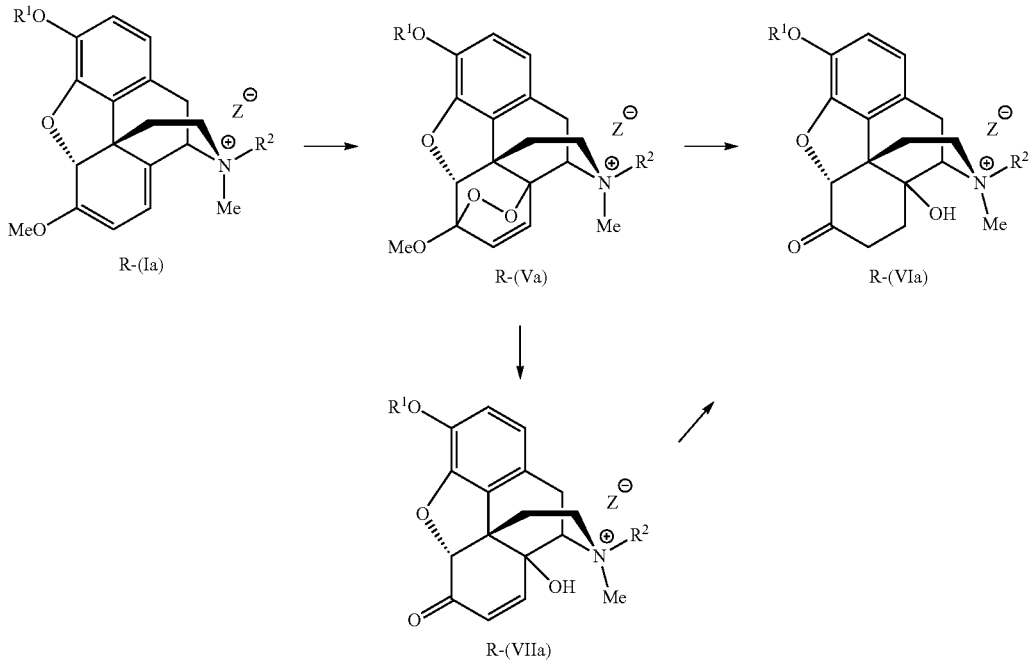

wherein

R[1] is selected from hydrogen, $C_{1-6}$alkyl, $C(O)C_{1-6}$alkyl and PG; R[2] is selected from R[3], $C(O)R^3$, $S(O)R^3$ and $SO_2R^3$; R[3] is selected from $C_{2-6}$alkyl, $C_{1-6}$alkylene $C_{3-8}$cycloalkyl, $C_{1-6}$alkylene$C_{6-10}$aryl, $C_{1-6}$alkylene $C_{1-8}$heterocyclyl and $C_{1-6}$alkyleneC$_{1-10}$heteroaryl;

PG is a protecting group;

Z is a suitable counter anion; and each alkyl, alkylene and aryl is optionally fluoro-substituted and/or deuterated.

23. The process of claim 1, wherein the compound of the formula (IV) is used for the synthesis of compounds of formula (VIII) comprising reacting the compounds of formula (IV) with a source of singlet oxygen or a peracid under conditions to form compounds of the formula (IX), which are reduced under conditions to form the compounds of the formula (VIII):

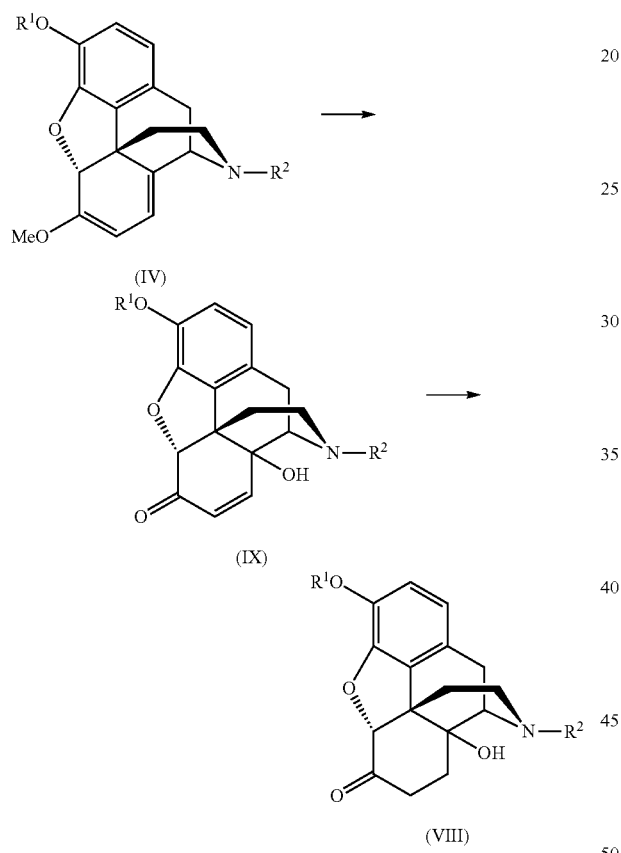

wherein

R[1] is selected from hydrogen, $C_{1-6}$alkyl, $C(O)C_{1-6}$alkyl and PG;

R[2] is selected from R[3], $C(O)R^3$, $S(O)R^3$ and $SO_2R^3$;

R[3] is selected from $C_{2-6}$alk, $C_{1-6}$alkylene$C_{3-8}$cycloalkyl, $C_{1-6}$alkyleneC$_{6-10}$aryl, $C_{1-6}$alkyleneC$_{1-8}$heterocyclyl and $C_{1-6}$alkyleneC$_{1-10}$heteroaryl;

PG is a protecting group; and each alkyl, alkylene and aryl is optionally fluoro-substituted and/or deuterated.

24. The process of claim 23, wherein the conditions for the formation of the compound of formula (IX) from the compound of the formula (IV) comprise dissolving the compound of the formula (IV) in a suitable solvent or mixture of solvents and adding a peracid or hydrogen peroxide in the presence of an acid.

25. The process of claim 24, wherein the conditions for the formation of the compound of formula (IX) from the compound of the formula (IV) further comprises at a temperature of about −20 °C. to about 50 °C. and a time of about 10 minutes to about 10 hours.

26. The process of claim 23, wherein the peracids is selected from performic acid, peracetic acid, m-chloroperbenzoic acid, hydrogen peroxide and potassium peroxymonosulfate.

27. The process of claim 1, wherein the compound of the formula (IV) is used for preparing a compound of the formula (X) by reacting a compound of the formula (IV) with methyl vinyl ketone under cycloaddition reaction conditions, followed by reduction under conditions to form a compound of the formula (XI) which is then reacted with a reagent of the formula (XII) under conditions to form the compound of the formula (X):

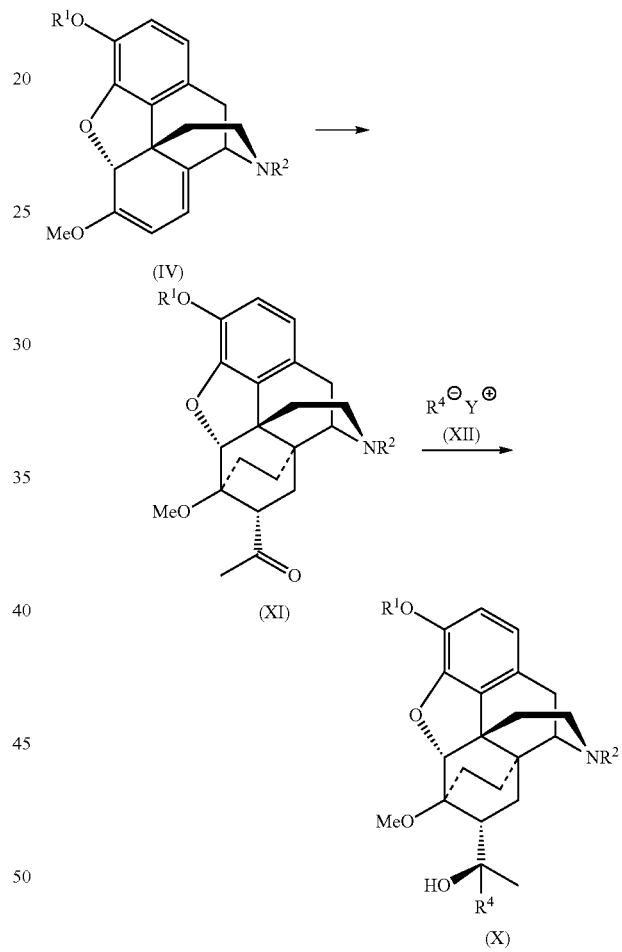

R[1] is selected from hydrogen, $C_{1-6}$alkyl and $C(O)C_{1-6}$alkyl and PG;

R[2] is selected from R[3], $C(O)R^3$, $S(O)R^3$ and $SO_2R^3$;

R[3] is selected from $C_{2-6}$alkyl, $C_{1-6}$alkylene$C_{3-8}$cycloalkyl, $C_{1-6}$alkyleneC$_{6-10}$aryl, $C_{1-6}$alkyleneC$_{1-8}$heterocyclyl and $C_{1-6}$alkyleneC$_{1-10}$heteroaryl;

R[4] is selected from $C_{1-6}$alkyl, $C_{3-8}$cycloalkyl and $C_{6-10}$aryl;

Y is a suitable counter cation; and each alkyl, alkylene and aryl is optionally fluoro-substituted and/or deuterated.

* * * * *